United States Patent
Shiraishi et al.

(10) Patent No.: US 7,288,654 B2
(45) Date of Patent: Oct. 30, 2007

(54) FUSED-RING PYRIDINE DERIVATIVE, PROCESS FOR PRODUCING THE SAME, AND USE

(75) Inventors: Mitsuru Shiraishi, Osaka (JP); Katsuji Aikawa, Osaka (JP); Naoyuki Kanzaki, Osaka (JP); Masanori Baba, Kagoshima (JP)

(73) Assignee: Takeda Pharmaceutical Company Ltd (JP)

( * ) Notice: Subject to any disclaimer, the term of this patent is extended or adjusted under 35 U.S.C. 154(b) by 38 days.

(21) Appl. No.: 10/544,435

(22) PCT Filed: Feb. 5, 2004

(86) PCT No.: PCT/JP2004/001169

§ 371 (c)(1),
(2), (4) Date: Sep. 1, 2005

(87) PCT Pub. No.: WO2004/069833

PCT Pub. Date: Aug. 19, 2004

(65) Prior Publication Data

US 2006/0100197 A1   May 11, 2006

(30) Foreign Application Priority Data

Feb. 7, 2003 (JP) .............................. 2003-031036

(51) Int. Cl.
    *C07D 471/02*  (2006.01)
(52) U.S. Cl. ...................................................... 546/113
(58) Field of Classification Search ................. 546/113
    See application file for complete search history.

(56) References Cited

U.S. PATENT DOCUMENTS

| 5,716,944 A | 2/1998 | Sohda et al. |
| 6,096,780 A | 8/2000 | Shiraishi et al. |
| 6,166,006 A | 12/2000 | Shiraishi et al. |
| 6,235,771 B1 | 5/2001 | Shiraishi et al. |
| 6,627,651 B1 | 9/2003 | Shiraishi et al. |
| 6,936,602 B1 | 8/2005 | Shiraishi et al. |

FOREIGN PATENT DOCUMENTS

| EP | 0 892 805 | 1/1999 |
| EP | 1 236 476 | 9/2002 |
| JP | 2003119191 | 4/2003 |
| JP | 2003335776 | 11/2003 |
| JP | 2004002402 | 1/2004 |
| JP | 2004043432 | 2/2004 |
| WO | WO 99/32100 | * 7/1999 |

* cited by examiner

Primary Examiner—D. Margaret Seaman
Assistant Examiner—Nizal S. Chandrakumar
(74) Attorney, Agent, or Firm—David G. Conlin; Edwards Angell Palmer & Dodge LLP

(57) ABSTRACT

The present invention provides a compound represented by the formula:

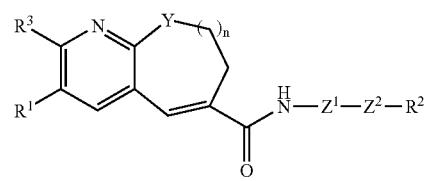

wherein $R^1$ is a 5- or 6-membered ring which may be substituted;
$R^3$ is a hydrogen atom, a lower alkyl group or a lower alkoxy group;
$Z^1$ is a 5- or 6-membered aromatic ring;
$Z^2$ is a group represented by $-Z^{2a}-W^2-Z^{2b}$ wherein $Z^{2a}$ and $Z^{2b}$ are each O, $S(O)_m$ (wherein m is 0, 1 or 2), an imino group, or a bond; and $W^2$ is an alkylene chain which may be substituted;
n is an integer of 0 to 4;
Y is O, $S(O)_p$ (wherein p is 0, 1 or 2), $CH_2$ or $NR^4$ (wherein $R^4$ is a hydrogen atom, a hydrocarbon group, a heterocyclic group, or an acyl group); and
$R^2$ is (1) an amino group, in which the nitrogen atom is converted to quaternary ammonium or oxide, (2) a nitrogen-containing heterocyclic group which may contain a sulfur atom or an oxygen atom as a ring-constituting atom, in which the nitrogen atom may be converted to a quaternary ammonium or an oxide, and the like, or a salt thereof.

The compound has excellent CCR5 antagonist activity and is useful as a prophylactic and/or therapeutic medicine for HIV infection in human peripheral mononuclear blood cells, especially AIDS.

19 Claims, No Drawings

FUSED-RING PYRIDINE DERIVATIVE, PROCESS FOR PRODUCING THE SAME, AND USE

This application is the National Phase filing of International Patent Application No. PCT/JP2004/001169, filed Feb. 5, 2004.

TECHNICAL FIELD

The present invention relates to a new cyclic compound having CCR antagonist activity, especially CCR5 antagonist activity, and to use thereof.

BACKGROUND ART

Recently, HIV (human immunodeficiency virus) protease inhibitors have been developed for the treatment of AIDS (acquired immune deficiency syndrome). With combined use of the protease inhibitors with two HIV reverse transcriptase inhibitors which have been commonly used, treatment of AIDS has made remarkable progress. However, the treatment of AIDS is still not efficient enough for the eradication of AIDS, and development of a new anti-AIDS medicine based on a different mechanism of action is desired.

As a receptor upon invasion of HIV into a target cell, CD4 has already been known. Recently, CCR5 as a second receptor of macrophage directed HIV and CXCR4 as a second receptor of T cell directed HIV, which are G-protein coupled chemokine receptors having a seven-transmembrane protein structure, have been found, and these chemokine receptors are considered to play an essential role for infection and transmission of HIV. As a matter of fact, it has been reported that a human having resistance to HIV infection even after repeated exposures to the virus had a mutation in which CCR5 gene was deleted homozygously. Thus, the CCR5 antagonists have been expected to become a new anti-HIV medicine, and examples of synthesis of new anilide derivatives having CCR5 antagonist activity have been reported in, for example, the below-mentioned patent applications such as Patent Document 1, Patent Document 2, and Patent Document 3, while there has been no report of a CCR5 antagonist which has been commercialized as a therapeutic medicine for AIDS. Further, a compound having CCR5 antagonist activity is described to be useful as a prophylactic and/or therapeutic medicine for AIDS in the below-mentioned Patent Document 4, but the compound has a different structure from the compound of the present invention.

Patent Document 1: WO99/32100
Patent Document 2: Japanese Patent Application No. 10-234388
Patent Document 3: Japanese Patent Application No. 10-363404
Patent Document 4: JP-A No. 2001-026586

DISCLOSURE OF THE INVENTION

The present invention is to provide a new bicyclic compound that is useful as a prophylactic and/or therapeutic medicine for HIV infection, especially AIDS, due to its CCR antagonist activity, especially CCR5 antagonist activity.

The present inventors have intensively studied compounds having CCR5 antagonist activity and found a compound of the following formula (I) or a salt thereof (hereinafter, sometimes, referred to as compound (I)), has a clinically favorable pharmaceutical effect including CCR antagonist activity, especially excellent CCR5 antagonist activity, and completed the present invention.

Thus, the present invention provides:

[1] A compound represented by the formula:

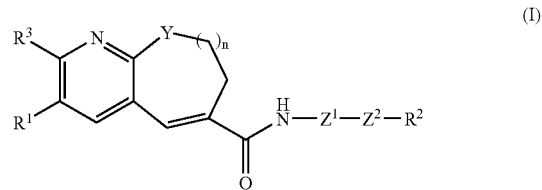

wherein $R^1$ is a 5- or 6-membered ring which may be substituted;

$R^3$ is a hydrogen atom, a lower alkyl group which may be substituted or a lower alkoxy group which may be substituted;

$Z^1$ is a 5- or 6-membered aromatic ring which may be further substituted;

$Z^2$ is a group represented by $-Z^{2a}-W^1-Z^{2b}$- wherein $Z^{2a}$ and $Z^{2b}$ are each O, $S(O)_m$ (wherein m is 0, 1 or 2), an imino group which may be substituted, or a bond; and $W^1$ is an alkylene chain which may be substituted, an alkenylene chain which may be substituted, or a bond;

n is an integer of 0 to 4;

Y is O, $S(O)_p$ (wherein p is 0, 1 or 2), $CH_2$ or $NR^4$ (wherein $R^4$ is a hydrogen atom, a hydrocarbon group which may be substituted, a heterocyclic group which may be substituted, or an acyl group which may be substituted); and $R^2$ is (1) an amino group which may be substituted, in which the nitrogen atom may be converted to a quaternary ammonium or an oxide, (2) a nitrogen-containing heterocyclic group which may be substituted and may contain a sulfur atom or an oxygen atom as a ring-constituting atom, in which the nitrogen atom may be converted to a quaternary ammonium or an oxide, (3) a group represented by the formula:

wherein k is 0 or 1; when k is 0, the phosphorus atom may form a phosphonium salt; $R^5$ and $R^6$ are each a hydrocarbon group which may be substituted, a hydroxy group which may be substituted or an amino group which may be substituted; or $R^5$ and $R^6$ may be bonded to each other to form a ring with the adjacent phosphorus atom, (4) an amidino group which may be substituted, or (5) a guanidino group which may be substituted, or a salt thereof;

[2] A prodrug of the compound according to the above [1];

[3] The compound according to the above [1], wherein $R^1$ is a benzene, a furan, a thiophene, a pyridine, a cyclopentane, a cyclohexane, a pyrrolidine, a piperidine, a piperazine, a morpholine, a thiomorpholine or a tetrahydropyran, each of which may be substituted;

[4] The compound according to the above [1], wherein $R^1$ is a benzene which may be substituted;

[5] The compound according to the above [1], wherein n is 2;

[6] The compound according to the above [1], wherein $Z^1$ is a benzene which may be substituted with a substituent selected from (1) a halogen atom, (2) a $C_{1-4}$ alkyl group which may be substituted with a halogen atom, and (3) a $C_{1-4}$ alkoxy group which may be substituted with a halogen atom;

[7] The compound according to the above [1], wherein $Z^1$ is a benzene which may be substituted with a methyl group or a trifluoromethyl group;

[8] The compound according to the above [1], wherein $Z^2$ is a group represented by -$Z^{2a}$-$W^2$-$Z^{2b}$- wherein $Z^{2a}$ and $Z^{2b}$ are each O, $S(O)_m$ (wherein m is 0, 1 or 2), an imino group which may be substituted, or a bond; and $W^2$ is an alkylene chain which may be substituted;

[9] The compound according to the above [1], wherein $Z^2$ is —$CH_2$—, —CH(OH)—, or —$S(O)_m$—$CH_2$— (wherein m is 0, 1 or 2);

[10] The compound according to the above [1], wherein $Z^2$ is a group represented by —$S(O)_m$—$CH_2$— (wherein m is 0, 1 or 2);

[11] The compound according to the above [1], wherein $R^2$ is (1) an amino group which may be substituted, in which the nitrogen atom may be converted to a quaternary ammonium or an oxide, (2) a nitrogen-containing heterocyclic group which may be substituted and may contain a sulfur atom or an oxygen atom as a ring-constituting atom, in which the nitrogen atom may be converted to a quaternary ammonium or an oxide, (3) an amidino group which may be substituted, or (4) a guanidino group which may be substituted;

[12] The compound according to the above [1], wherein $R^2$ is an amino group which may be substituted, or a nitrogen-containing heterocyclic group which may be substituted and may contain a sulfur atom or an oxygen atom as a ring-constituting atom;

[13] The compound according to the above [1], wherein $R^2$ is represented by the formula —NRR' (wherein R and R' are each an aliphatic hydrocarbon group which may be substituted, or an alicyclic heterocyclic group which may be substituted);

[14] The compound according to the above [1], wherein $R^2$ is a nitrogen-containing aromatic heterocyclic group which may be substituted;

[15] The compound according to the above [1], wherein $R^2$ is an imidazolyl group which may be substituted or a triazolyl group which may be substituted;

[16] The compound according to the above [1], wherein $R^1$ is a benzene, a furan, a thiophene, a pyridine, a cyclopentane, a cyclohexane, a pyrrolidine, a piperidine, a piperazine, a morpholine, a thiomorpholine or a tetrahydropyran, each of which may be substituted with a halogen, a nitro, a cyano, a $C_{1-6}$ alkyl, a $C_{1-6}$ alkoxy, a $C_{1-6}$ alkoxy-$C_{1-6}$ alkyl or a $C_{1-6}$ alkoxy-$C_{1-6}$ alkoxy, a Y-containing ring is a 7- to 10-membered ring which may contain an oxygen atom, a nitrogen atom or a sulfur atom which may be oxidized, as a ring-constituting atom, and may have, as a substituent, an alkyl which may be substituted, an alkenyl which may be substituted, an aryl which may be substituted, a heterocyclic group which may be substituted or formyl, $Z^1$ is a benzene which may be substituted with substituent(s) selected from (1) a halogen atom, (2) a $C_{1-4}$ alkyl group which may be substituted with halogen atom(s) and (3) a $C_{1-4}$ alkoxy group which may be substituted with halogen atom(s), $Z^2$ is -$Z^{2a}$-$W^1$-$Z^{2b}$- wherein $Z^{2a}$ and $Z^{2b}$ are each I, $S(O)_m$ (wherein m is 0, 1 or 2), an imino group which may be substituted with a $C_{1-4}$ alkyl group or a bond, and $W^1$ is a bond, or a $C_{1-4}$ alkylene chain or a $C_{2-4}$ alkenylene chain, each of which may have, as a substituent, a $C_{1-6}$ alkyl, a hydroxy group, a hydroxyimino or a $C_{1-6}$ alkoxyimino, and $R^2$ is an amino group which may be substituted with a $C_{1-4}$ alkyl group, or a nitrogen-containing heterocyclic group which may contain a sulfur atom or an oxygen atom as a ring-constituting atom and may be substituted with a $C_{1-4}$ alkyl group;

[17] A compound represented by the formula:

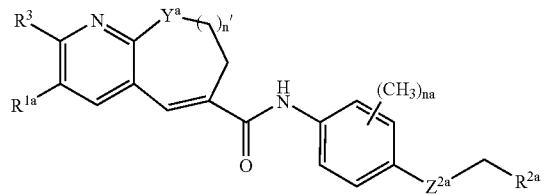

(Ia)

wherein $R^{1a}$ is a ($C_{1-6}$ alkoxy-$C_{1-6}$ alkoxy)phenyl;

$R^{2a}$ is (1) an N—$C_{1-6}$ alkyl-N-tetrahydropyranylamino, (2) an imidazolyl which may be substituted with a $C_{1-6}$ alkyl which may be substituted, or (3) a triazolyl which may be substituted with a $C_{1-6}$ alkyl which may be substituted;

$R^3$ is a hydrogen atom, a lower alkyl group which may be substituted or a lower alkoxy group which may be substituted;

$Y^a$ is (1) an oxygen atom, (2) $S(O)_p$ (wherein p is 0, 1 or 2), (3) $CH_2$ or (4) an imino group which may have, as a substituent, a formyl, a $C_{1-6}$ alkyl which may be substituted, a $C_{2-6}$ alkenyl which may be substituted, an aryl which may be substituted, a heterocyclic group which may be substituted, an arylmethyl which may be substituted or a heterocyclic methyl which may be substituted;

N' is 1, 2 or 3;

na is 0 or 1;

$Z^{2a}$ is a bond, S, SO or $SO_2$; and the other symbols have the same meanings as defined above, or a salt thereof;

[18] The compound according to the above [17], wherein $Z^{2a}$ is SO;

[19] The compound according to the above [18], wherein $Z^{2a}$ is SO having a configuration of (S);

[20] The compound according to the above, wherein $y^a$ is an imino group which may have, as a substituent, a formyl, a $C_{1-6}$ alkyl which may be substituted, a $C_{2-6}$ alkenyl which may be substituted, an aryl which may be substituted, a heterocyclic group which may be substituted, an arylmethyl which may be substituted or a heterocyclic methyl which may be substituted;

[21] (S)-3-[4-(2-butoxyethoxy)phenyl]-10-isobutyl-N-[4-[[(1-propyl-1H-imidazol-5-yl)methyl]sulfinyl]phenyl]-7,8,9,10-tetrahydropyrido[2,3-b]azocine-6-carboxamide;

[22] (S)-3-[4-(2-butoxyethoxy)phenyl]-10-propyl-N-[4-[[(1-propyl-1H-imidazol-5-yl)methyl]sulfinyl]phenyl]-7,8,9,10-tetrahydropyrido[2,3-b]azocine-6-carboxamide;

[23] A process for producing a compound represented by the formula:

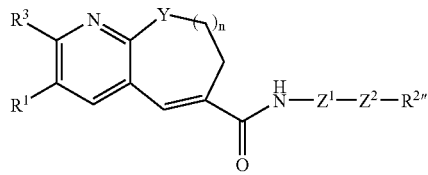

wherein $R^{2''}$ is (1) an amino group which may be substituted, in which the nitrogen atom may be converted to a quaternary ammonium, (2) a nitrogen-containing heterocyclic group which may be substituted and may contain a sulfur atom or an oxygen atom as a ring-constituting atom, in which the nitrogen atom may be converted to a quaternary ammonium, or (3) a group represented by the formula (a); and the other symbols have the same meanings as defined above, or a salt thereof, which comprises subjecting a compound represented by the formula:

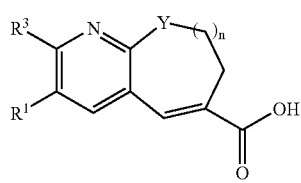

wherein each symbol has the same meaning as defined above, or a salt thereof or a reactive derivative thereof, and a compound represented by the formula:

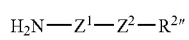

wherein each symbol has the same meaning as defined above, or salt thereof, to a condensation reaction, and then optionally to a deprotection reaction, an oxidation/reduction reaction and/or a quaternization reaction;

[24] A pharmaceutical composition comprising a compound represented by the formula (I), a salt thereof or a prodrug thereof;

[25] The pharmaceutical composition according to the above [24], which is a CCR antagonist;

[26] The pharmaceutical composition according to the above [25], wherein CCR is CCR5 and/or CCR2;

[27] The pharmaceutical composition according to the above [25], wherein CCR is CCR5;

[28] The pharmaceutical composition according to the above, which is a prophylactic and/or therapeutic agent for HIV infection, chronic rheumatoid arthritis, autommune diseases, allergic diseases, ischemic brain cell disorder, cardiac infarction, nephritis/nephropathy, arteriosclerosis or graft-versus-host diseases;

[29] The pharmaceutical composition according to the above [24], which is a prophylactic and/or therapeutic agent for HIV infection;

[30] The pharmaceutical composition according to the above [24], which is a prophylactic and/or therapeutic agent for AIDS;

[31] The pharmaceutical composition according to the above [24], which is a suppressive agent for disease progression of AIDS;

[32] A process for preventing or treating HIV infection, chronic rheumatoid arthritis, autoimmune diseases, allergic diseases, ischemic brain cell disorder, cardiac infarction, nephritis/nephropathy, arteriosclerosis or graft-versus-host diseases, which comprises administering an effective amount of the compound according to the above [I], a salt thereof or a prodrug thereof, to a subject in need thereof; and

[33] Use of the compound according to the above [I], a salt thereof or a prodrug thereof, for manufacturing a prophylactic and/or therapeutic agent for HIV infection, chronic rheumatoid arthritis, autoimmune diseases, allergic diseases, ischemic brain cell disorder, cardiac infarction, nephritis/nephropathy, arteriosclerosis or graft-versus-host diseases.

BEST MODE FOR CARRYING OUT THE INVENTION

In the above-described formula (I), the "5- or 6-membered ring" in the "5- or 6-membered ring which may be substituted" represented by $R^1$ may be exemplified by a group which is formed by eliminating one hydrogen atom from 6-membered aromatic hydrocarbon such as benzene, etc.; 5- or 6-membered aliphatic hydrocarbon such as cyclopentane, cyclohexane, cyclopentene, cyclohexene, cyclopentadiene, cyclohexadiene, etc.; a 5- or 6-membered aromatic heterocyclic ring containing 1 to 4 heteroatoms of one or two kinds selected from a nitrogen atom, a sulfur atom and an oxygen atom, such as furan, thiophene, pyrrole, imidazole, pyrazole, thiazole, oxazole, isothiazole, isoxazole, tetrazole, pyridine, pyrazine, pyrimidine, pyridazine, triazole, etc.; a 5- or 6-membered non-aromatic heterocyclic ring containing 1 to 4 heteroatoms of one or two kinds selected from a nitrogen atom, a sulfur atom and an oxygen atom, such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, tetrahydrothiopyran, etc.; and the like. Among them, the "5- or 6-membered ring" is preferably benzene, furan, thiophene, pyridine, cyclopentane, cyclohexane, pyrrolidine, piperidine, piperazine, morpholine, thiomorpholine, tetrahydropyran (preferably a 6-membered ring), and the like, it being particularly preferably benzene.

The "substituent" which may be carried by the "5- or 6-membered ring" of the "5- or 6-membered ring which may be substituted" represented by $R^1$ may be exemplified by halogen atom, nitro, cyano, alkyl which may be substituted, cycloalkyl which may be substituted, hydroxy group which may be substituted, thiol group which may be substituted (wherein the sulfur atom may be oxidized, or may form sulfmyl which may be substituted or sulfonyl which may be substituted), amino group which may be substituted, acyl which may be substituted, carboxyl group which may be esterified, an aromatic group which may be substituted, and the like.

Examples of the "halogen" as the substituent of $R^1$ include fluorine, chlorine, bromine, iodine and the like, it being particularly preferably fluorine and chlorine.

The "alkyl" of the "alkyl which may be substituted" as the substituent of $R^1$ may be exemplified by linear or branched alkyl having 1 to 10 carbon atoms, for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., and preferably lower ($C_{1-6}$) alkyl. Examples of the substituent of the "alkyl which may be substituted" include halogen (for example, fluorine, chlorine, bromine, iodine, etc.), nitro, cyano, hydroxy group, thiol group which may be substituted (for example, thiol, $C_{1-4}$ alkylthio, etc.), amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc.), carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc.), $C_{1-4}$ alkoxy which may be halogenated (for example, methoxy, ethoxy, propoxy, butoxy, trifluoromethoxy, trifluoroethoxy, etc.), $C_{1-4}$ alkoxy-$C_{1-4}$ alkoxy which may halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like, and the number of the substituents is preferably 1 to 3.

Examples of the cycloalkyl of the "cycloalkyl which may be substituted" as the substituent of $R^1$ include $C_{3-7}$ cycloalkyl such as cyclopropyl, cyclobutyl, cyclopentyl, cyclohexyl, cycloheptyl, etc. Examples of the "substituent" in the "cycloalkyl which may be substituted" include halogen (for example, fluorine, chlorine, bromine, iodine, etc.), nitro, cyano, hydroxy group, thiol group which may be substituted (for example, thiol, $C_{1-4}$ alkylthio, etc.), amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc., and the like), carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc.), $C_{1-4}$ alkoxy which may be halogenated (for example, methoxy, ethoxy, propoxy, butoxy, trifluoromethoxy, trifluoroethoxy, etc.), $C_{1-4}$ alkoxy-$C_{1-4}$ alkoxy which may be halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like, and the number of the substituents is preferably 1 to 3.

The substituent of the "hydroxy group which may be substituted" as the substituent of $R^1$ may be exemplified by (1) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl; and the like);

(2) cycloalkyl which may be substituted and may contain heteroatom(s) (for example, $C_{3-7}$ cycloalkyl such as cyclopropyl, cyclobutyl, cyclopentyl, cyclohexyl, cycloheptyl, etc.; 5- or 6-membered saturated heterocyclic group containing 1 or 2 heteroatoms, such as tetrahydrofuranyl, tetrahydrothienyl, pyrrolidinyl, pyrazolidinyl, piperidyl, piperazinyl, morpholinyl, thiomorpholinyl, tetrahydropyranyl, tetrahydrothiopyranyl, etc., and preferably tetrahydropyranyl, etc.; and the like);

(3) alkenyl which may be substituted (for example, alkenyl having 2 to 10 carbon atoms, such as allyl, crotyl, 2-pentenyl, 3-hexenyl, etc., preferably lower ($C_{2-6}$) alkenyl; and the like);

(4) cycloalkenyl which may be substituted (for example, cycloalkenyl having 3 to 7 carbon atoms, such as 2-cyclopentenyl, 2-cyclohexenyl, 2-cyclopentenylmethyl, 2-cyclohexenylmethyl, etc.; and the like);

(5) aralkyl which may be substituted (for example, phenyl-$C_{1-4}$ alkyl such as benzyl, phenethyl, etc.; and the like);

(6) formyl, or acyl which may be substituted (for example, alkanoyl having 2 to 4 carbon atoms, such as acetyl, propionyl, butyryl, isobutyryl, etc., alkylsulfonyl having 1 to 4 carbon atoms (for example, methanesulfonyl, ethanesulfonyl, etc.), and the like);

(7) aryl which may be substituted (for example, phenyl, naphthyl, etc.); and the like.

The substituent which may be carried by the above-described (1) alkyl which may be substituted, (2) cycloalkyl which may be substituted, (3) alkenyl which may be substituted, (4) cycloalkenyl which may be substituted, (5) aralkyl which may be substituted, (6) acyl which may be substituted, and (7) aryl which may be substituted, may be exemplified by halogen (for example, fluorine, chlorine, bromine, iodine, etc.), nitro, cyano, hydroxy group, thiol group which may be substituted (for example, thiol, $C_{1-4}$ alkylthio, etc.), amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc., and the like), carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc.), $C_{1-4}$ alkyl which may be halogenated (for example, trifluoromethyl, methyl, ethyl, etc.), $C_{1-6}$ alkoxy which may be halogenated (for example, methoxy, ethoxy, propoxy, butoxy, trifluoromethoxy, trifluoroethoxy, etc.; preferably $C_{1-4}$ alkoxy which may be halogenated), formyl, $C_{2-4}$ alkanoyl (for example, acetyl, propionyl, etc.), $C_{1-4}$ alkylsulfonyl (for example, methanesulfonyl, ethanesulfonyl, etc.), a 5- or 6-membered aromatic heterocyclic ring which may be substituted [for example, a 5- or 6-membered aromatic heterocyclic ring containing 1 to 4 heteroatoms of one or two kinds selected from a nitrogen atom, a sulfur atom and an oxygen atom, such as furan, thiophene, pyrrole, imidazole, pyrazole, thiazole, oxazole, isothiazole, isoxazole, tetrazole, pyridine, pyrazine, pyrimidine, pyridazine, triazole, etc.; examples of the substituent which may be carried by the heterocyclic ring include halogen (for example, fluorine, chlorine, bromine, iodine, etc.), nitro, cyano, hydroxy group, thiol group, amino group, carboxyl group, $C_{1-4}$ alkyl which may be halogenated (for example, trifluoromethyl, methyl, ethyl, etc.), $C_{1-4}$ alkoxy which may be halogenated (for example, methoxy, ethoxy, propoxy, butoxy, trifluoromethoxy, trifluoroethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like; and the number of the substituents is preferably 1 to 3], and the like; and the number of the substituents is preferably 1 to 3.

The substituent of the "thiol group which may be substituted" as the substituent of $R^1$ may be exemplified by the same one as the "substituent of hydroxy group which may be substituted as the substituent of $R^1$," and preferred among them are:

(1) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl; and the like);

(2) cycloalkyl which may be substituted (for example, $C_{3-7}$ cycloalkyl such as cyclopropyl, cyclobutyl, cyclopentyl, cyclohexyl, cycloheptyl, etc.);

(3) aralkyl which may be substituted (for example, phenyl-$C_{1-4}$ alkyl such as benzyl, phenethyl, etc.);

(4) aryl which may be substituted (for example, phenyl, naphthyl, etc.); and the like.

The substituent which may be carried by the above-described (1) alkyl which may be substituted, (2) cycloalkyl which may be substituted, (3) aralkyl which may be substituted and (4) aryl which may be substituted may be exemplified by halogen (for example, fluorine, chlorine, bromine, iodine, etc.), nitro, cyano, hydroxy group, thiol group which may be substituted (for example, thiol, $C_{1-4}$ alkylthio, etc.), amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc.), carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc.), $C_{1-4}$ alkoxy which may be halogenated (for example, methoxy, ethoxy, propoxy, butoxy, trifluoromethoxy, trifluoroethoxy, etc.), $C_{1-4}$ alkoxy-$C_{1-4}$ alkoxy which may be halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like, and the number of the substituents is preferably 1 to 3.

The substituent of the "amino group which may be substituted" as the substituent of $R^1$ may be exemplified by the same one as the "substituent of hydroxy group which may be substituted as the substituent of $R^1$," and the number of substituents on the amino group may be 1 or 2. Among them, the substituent is preferably:

(1) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, and the like);

(2) cycloalkyl which may be substituted (for example, $C_{3-7}$ cycloalkyl group such as cyclopropyl, cyclobutyl, cyclopentyl, cyclohexyl, cycloheptyl, etc., and the like);

(3) alkenyl which may be substituted (for example, alkenyl having 2 to 10 carbon atoms, such as allyl, crotyl, 2-pentenyl, 3-hexenyl, etc., preferably lower ($C_{2-6}$) alkenyl and the like);

(4) cycloalkenyl which may be substituted (for example, cycloalkenyl having 3 to 7 carbon atoms, such as 2-cyclopentenyl, 2-cyclohexenyl, 2-cyclopentenylmethyl, 2-cyclohexenylmethyl, etc.; and the like);

(5) formyl, or acyl which may be substituted (for example, alkanoyl having 2 to 4 carbon atoms (for example, acetyl, propionyl, butyryl, isobutyryl, etc.), alkylsulfonyl having 1 to 4 carbon atoms (for example, methanesulfonyl, ethanesulfonyl, etc.) and the like);

(6) aryl which may be substituted (for example, phenyl, naphthyl, etc.); and the like.

Examples of the substituent which may be carried by the above-described (1) alkyl which may be substituted, (2) cycloalkyl which may be substituted, (3) alkenyl which may be substituted, (4) cycloalkenyl which may be substituted, (5) acyl which may be substituted, and (6) aryl which may be substituted, include halogen (for example, fluorine, chlorine, bromine, iodine, etc.), nitro, cyano, hydroxy group, thiol group which may be substituted (for example, thiol, $C_{1-4}$ alkylthio, etc.), amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc.), carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc.), $C_{1-4}$ alkoxy which may be halogenated (for example, methoxy, ethoxy, propoxy, butoxy, trifluoromethoxy, trifluoroethoxy, etc.), $C_{1-4}$ alkoxy-$C_{1-4}$ alkoxy which may be halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like, and the number of the substituents is preferably 1 to 3.

Further, the substituents of the "amino which may be substituted" as the substituent of $R^1$ may be bonded to each other to form a cyclic amino group (for example, a group which is formed by eliminating one hydrogen atom from the ring-constituting nitrogen atom of a 5- or 6-membered ring such as tetrahydropyrrole, piperazine, piperidine, morpholine, thiomorpholine, pyrrole, imidazole, etc. so that a bond is made available on the nitrogen atom, and the like). This cyclic amino group may be substituted, and examples of the substituent include halogen (for example, fluorine, chlorine, bromine, iodine, etc.), nitro, cyano, hydroxy group, thiol group which may be substituted (for example, thiol, $C_{1-4}$ alkylthio, etc.), amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc.), carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc.), $C_{1-4}$ alkoxy which may be halogenated (for example, methoxy, ethoxy, propoxy, butoxy, trifluoromethoxy, trifluoroethoxy, etc.), $C_{1-4}$ alkoxy-$C_{1-4}$ alkoxy which may halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl), and the like, while the number of the substituents is preferably 1 to 3.

The "acyl which may be substituted" as the substituent of $R^1$ may be exemplified by a group in which (1) hydrogen;

(2) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl and the like);

(3) cycloalkyl which may be substituted (for example, $C_{3-7}$ cycloalkyl such as cyclopropyl, cyclobutyl, cyclopentyl, cyclohexyl, cycloheptyl, etc., and the like);

(4) alkenyl which may be substituted (for example, alkenyl having 2 to 10 carbon atoms such as allyl, crotyl, 2-pentenyl, 3-hexenyl, etc., preferably lower ($C_{2-6}$) alkenyl and the like);

(5) cycloalkenyl which may be substituted (for example, cycloalkenyl having 3 to 7 carbon atoms, such as 2-cyclopentenyl, 2-cyclohexenyl, 2-cyclopentenylmethyl, 2-cyclohexenylmethyl, etc., and the like);

(6) 5- or 6-membered monocyclic aromatic group which may be substituted (for example, phenyl, pyridyl, etc.) or the like is bonded to a carbonyl group or a sulfonyl group (for example, formyl, acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, methanesulfonyl, ethanesulfonyl, etc.). Examples of the substituent which may be carried by the above-described (2) alkyl which may be substituted, (3) cycloalkyl which may be substituted, (4) alkenyl which may be substituted, (5) cycloalkenyl which may be substituted, and (6) 5- or 6-membered monocyclic aromatic group which may be substituted, include halogen (for example, fluorine, chlorine, bromine, iodine, etc.), nitro, cyano, hydroxy group, thiol group which may be substituted (for example, thiol, $C_{1-4}$ alkylthio, etc.), amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc.), carboxyl group which may be esterified or amidated (for example, carboxyl, $C_{14}$ alkoxycarbonyl, carbamoyl, mono-$C_{1-4}$ alkylcarbamoyl, di-$C_{1-4}$ alkyl-carbamoyl, etc.), $C_{1-4}$ alkoxy which may be halogenated (for example, methoxy, ethoxy, propoxy, butoxy, trifluoromethoxy, trifluoroethoxy, etc.); $C_{1-4}$ alkoxy-$C_{1-4}$ alkoxy which may be halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like, and the number of the substituents is preferably 1 to 3.

The "carboxyl which may be esterified" as the substituent of $R^1$ may be exemplified by a group in which (1) hydrogen;

(2) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl and the like);

(3) cycloalkyl which may be substituted (for example, $C_{3-7}$ cycloalkyl such as cyclopropyl, cyclobutyl, cyclopentyl, cyclohexyl, cycloheptyl, etc., and the like);

(4) alkenyl which may be substituted (for example, alkenyl having 2 to 10 carbon atoms, such as allyl, crotyl, 2-pentenyl, 3-hexenyl, etc., preferably lower ($C_{2-6}$) alkenyl and the like);

(5) cycloalkenyl which may be substituted (for example, cycloalkenyl having 3 to 7 carbon atoms, such as 2-cyclopentenyl, 2-cyclohexenyl, 2-cyclopentenylmethyl, 2-cyclohexenylmethyl, etc., and the like);

(6) aryl which may be substituted (for example, phenyl, naphthyl, etc.) or the like is bonded to a carbonyloxy group, and preferably carboxyl, lower ($C_{1-6}$) alkoxycarbonyl, aryloxycarbonyl (for example, methoxycarbonyl, ethoxycarbonyl, propoxycarbonyl, phenoxycarbonyl, naphthoxycarbonyl, etc.), and the like. Examples of the substituent which may be carried by the above-described (2) alkyl which may be substituted, (3) cycloalkyl which may be substituted, (4) alkenyl which may be substituted, (5) cycloalkenyl which may be substituted, and (6) aryl which may be substituted, include halogen (for example, fluorine, chlorine, bromine, iodine, etc.), nitro, cyano, hydroxy group, thiol group which may be substituted (for example, thiol, $C_{1-4}$ alkylthio, etc.), amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc., and the like), carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc.), $C_{1-4}$ alkoxy which may be halogenated (for example, methoxy, ethoxy, propoxy, butoxy, trifluoromethoxy, trifluoroethoxy, etc.), $C_{1-4}$ alkoxy-$C_{1-4}$ alkoxy which may halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like, and the number of the substituents is preferably 1 to 3.

The "aromatic group" of the "aromatic group which may be substituted" as the substituent of $R^1$ may be exemplified by a 5- or 6-membered homocyclic or heterocyclic aromatic group such as phenyl, pyridyl, furyl, thienyl, pyrrolyl, imidazolyl, pyrazolyl, thiazolyl, oxazolyl, isothiazolyl, isoxazolyl, tetrazolyl, pyrazinyl, pyrimidinyl, pyridazinyl, triazolyl, etc.; a fused heterocyclic aromatic group such as benzofuran, indole, benzothiophene, benzoxazole, benzothiazole, indazole, benzimidazole, quinoline, isoquinoline, quinoxaline, phthalazine, quinazoline, cinnoline, imidazopyridine, etc.; and the like. Examples of the substituent of these aromatic groups include halogen (for example, fluorine, chlorine, bromine, iodine, etc.), nitro, cyano, hydroxy group, thiol group which may be substituted (for example, thiol, $C_{1-4}$ alkylthio, etc.), amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc., and the like), carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc.); $C_{1-4}$ alkyl which may be halogenated (for example, trifluoromethyl, methyl, ethyl, etc.); $C_{1-4}$ alkoxy which may be halogenated (for example, methoxy, ethoxy, propoxy, butoxy, trifluoromethoxy, trifluoroethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like, and the number of the substituents is preferably 1 to 3.

The number of the above substituents of $R^1$ may be 1 to 4, preferably 1 to 2, and the substituents which may be identical or different from each other may be present at any positions of the ring. When the "5- or 6-membered ring" of the "5- to 6-membered ring which may be substituted" represented by $R^1$ has two or more substituents, two of the substituents may be bonded to each other to form, for example, lower($C_{1-6}$) alkylene (for example, trimethylene, tetramethylene, etc.), lower ($C_{1-6}$) alkyleneoxy (for example, —CH$_2$—O—CH$_2$—, —O—CH$_2$—CH$_2$—, —O—CH$_2$—CH$_2$—CH$_2$—, —O—CH$_2$—CH$_2$—CH$_2$—CH$_2$—, —O—C(CH$_3$)(CH$_3$)—CH$_2$—CH$_2$—, etc.), lower ($C_{1-6}$) alkylenethio (for example, —CH$_2$—S—CH$_2$—, —S—CH$_2$—CH$_2$—, —S—CH$_2$—CH$_2$—CH$_2$—, —S—CH$_2$—CH$_2$—CH$_2$—CH$_2$—, —S—C(CH$_3$)(CH$_3$)—CH$_2$—CH$_2$—, etc.), lower ($C_{1-6}$) alkylenedioxy (for example, —O—CH$_2$—O—, —O—CH$_2$—CH$_2$—O—, —O—CH$_2$—CH$_2$—CH$_2$—O—, etc.), lower ($C_{1-6}$) alkylenedithio (for example, —S—CH$_2$—S—, —S—CH$_2$—CH$_2$—S—, —S—CH$_2$—CH$_2$—CH$_2$—S—, etc.), oxy-lower ($C_{1-6}$) alkyleneamino (for example, —O—CH$_2$—NH—, —O—CH$_2$—CH$_2$—NH—, etc.), oxy-lower ($C_{1-6}$) alkylenethio (for example, —O—CH$_2$—S—, —O—CH$_2$—CH$_2$—S—, etc.), lower ($C_{1-6}$) alkyleneamino (for example, —NH—CH$_2$—CH$_2$—, —NH—CH$_2$—CH$_2$—CH$_2$—, etc.), lower (C$_{1-6}$) alkylenediamino (for example, —NH—CH$_2$—NH—, —NH—CH$_2$—CH$_2$—NH—, etc.), thiolower (C$_{1-6}$) alkyleneamino (for example, —S—CH$_2$—NH—, —S—CH$_2$—CH$_2$—NH—, etc.), lower (C$_{2-6}$) alkenylene (for example, —CH$_2$-CH=CH—, —CH$_2$—CH$_2$—CH=CH—, —CH$_2$—CH=CH—CH$_2$—, etc.), lower (C$_{4-6}$) alkadienylene (for example, —CH=CH—CH=CH—, etc.), and the like.

Further, the divalent group formed by bonding of two substituents of R$^1$ may contain 1 to 3 substituents which are the same as the "substituents" which may be carried by the "5- or 6-membered ring" of the "5- or 6-membered ring which may be substituted" represented by R$^1$ (halogen atom, nitro, cyano, alkyl which may be substituted, cycloalkyl which may be substituted, hydroxy group which may be substituted, thiol group which may be substituted (wherein the sulfur atom may be oxidized, or may form sulfinyl group which may be substituted or sulfonyl group which may be substituted), amino group which may be substituted, acyl which may be substituted, carboxyl group which may be esterified or amidated, an aromatic group which may be substituted, and the like).

The "substituent" which may be carried by the "5- or 6-membered ring" of the "5- or 6-membered ring which may be substituted" represented by R$^1$ may be exemplified by, in particular, lower (C$_{1-4}$) alkyl which may be halogenated or lower (C$_{1-4}$) alkoxylated (for example, methyl, ethyl, t-butyl, trifluoromethyl, methoxymethyl, ethoxymethyl, propoxymethyl, butoxymethyl, methoxyethyl, ethoxyethyl, propoxyethyl, butoxyethyl, etc.), lower (C$_{1-4}$) alkoxy which may be halogenated or lower (C$_{1-4}$) alkoxylated (for example, methoxy, ethoxy, propoxy, butoxy, t-butoxy, trifluoromethoxy, methoxymethoxy, ethoxymethoxy, propoxymethoxy, butoxymethoxy, methoxyethoxy, ethoxyethoxy, propoxyethoxy, butoxyethoxy, methoxypropoxy, ethoxypropoxy, propoxypropoxy, butoxypropoxy, etc.), halogen (for example, fluorine, chlorine, etc.), nitro, cyano, amino which may be substituted with one or two of lower (C$_{1-4}$) alkyl, formyl or lower (C$_{2-4}$) alkanoyl (for example, amino, methylamino, dimethylamino, formylamino, acetylamino, etc.), a 5- or 6-membered cyclic amino group (for example, 1-pyrrolidinyl, 1-piperazinyl, 1-piperidinyl, 4-morpholino, 4-thiomorpholino, 1-imidazolyl, 4-tetrahydropyranyl, etc.), and the like.

Examples of the lower alkyl group of the "lower alkyl group which may be substituted" represented by R$^3$ above include C$_{1-6}$ alkyl such as methyl, ethyl, propyl, isopropyl, butyl, isobutyl, sec-butyl, tert-butyl, pentyl, isopentyl, neopentyl, hexyl, etc., and the like.

Examples of the lower alkoxy group of the "lower alkoxy group which may be substituted" represented by R$^3$ above include C$_{1-6}$ alkoxy such as methoxy, ethoxy, propoxy, butoxy, etc., and the like.

Examples of the substituent which may be carried by the "lower alkyl group which may be substituted" and "lower alkoxy group which may be substituted" include halogen (for example, fluorine, chlorine, bromine, iodine), hydroxy group, amino, mono(lower alkyl)amino, di(lower alkyl)amino, lower alkanoyl and the like.

The lower alkyl carried by the mono(lower alkyl)amino and di(lower alkyl)amino may be exemplified by the same lower alkyl group of the "lower alkyl group which may be substituted" represented by R$^3$ above.

The lower alkanoyl may be exemplified by C$_{2-6}$ alkanoyl such as acetyl, propionyl, butyryl, isobutyryl, etc.

Among them, as for R$^3$, the lower C$_{1-6}$ alkyl group which may be substituted is preferred, and particularly a methyl group which may be substituted is preferred.

With respect to a group of the above-described NR$^4$ represented by Y, the "hydrocarbon group" of the "hydrocarbon group which may be substituted" represented by R$^4$ may be exemplified by:

(1) alkyl (for example, C$_{1-0}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower (C$_{1-6}$) alkyl, more preferably lower (C$_{1-4}$) alkyl and the like);

(2) cycloalkyl (for example, C$_{3-7}$ cycloalkyl such as cyclopropyl, cyclobutyl, cyclopentyl, cyclohexyl, cycloheptyl, etc., and the like);

(3) alkenyl (for example, alkenyl having 2 to 10 carbon atoms, such as allyl, crotyl, 2-pentenyl, 3-hexenyl, etc., preferably lower (C$_{2-6}$) alkenyl and the like);

(4) cycloalkenyl (for example, cycloalkenyl having 3 to 7 carbon atoms, such as 2-cyclopentenyl, 2-cyclohexenyl, 2-cyclopentenylmethyl, 2-cyclohexenylmethyl, etc., and the like);

(5) alkynyl (for example, alkynyl having 2 to 10 carbon atoms, such as ethynyl, 1-propynyl, 2-propynyl, 1-butynyl, 2-pentynyl, 3-hexynyl, etc., preferably lower (C$_{2-6}$) alkynyl and the like);

(6) aralkyl (for example, phenyl-C$_{1-4}$ alkyl (for example, benzyl, phenethyl, etc.) and the like);

(7) aryl (for example, phenyl, naphthyl, etc.);

(8) cycloalkyl-alkyl (for example, C$_{3-7}$ cycloalkyl-C$_{1-4}$ alkyl such as cyclopropylmethyl, cyclobutylmethyl, cyclopentylmethyl, cyclohexylmethyl, cycloheptylmethyl, etc.); and the like.

Examples of the substituent which may be carried by the above-described (1) alkyl, (2) cycloalkyl, (3) alkenyl, (4) cycloalkenyl, (5) alkynyl, (6) aralkyl, (7) aryl and (8) cycloalkyl-alkyl, include halogen (for example, fluorine, chlorine, bromine, iodine, etc.), nitro, cyano, hydroxy group, thiol group which may be substituted (for example, thiol, C$_{1-4}$ alkylthio, etc.), amino group which may be substituted (for example, amino, mono-C$_{1-4}$ alkylamino, di-C$_{1-4}$ alkylamino, 5- or 6-membered cyclic amino such as tetrahydropyrrole, piperazine, piperidine, morpholine, thiomorpholine, pyrrole, imidazole, etc.), carboxyl group which may be esterified or amidated (for example, carboxyl, C$_{1-4}$ alkoxycarbonyl, carbamoyl, mono-C$_{1-4}$ alkylcarbamoyl, di-C$_{1-4}$ alkylcarbamoyl, etc.), C$_{1-4}$ alkyl which may be halogenated (for example, trifluoromethyl, methyl, ethyl, etc.), C$_{1-4}$ alkoxy which may be halogenated (for example, methoxy, ethoxy, propoxy, butoxy, trifluoromethoxy, trifluoroethoxy, etc.), C$_{1-4}$ alkylenedioxy (for example, —O—CH$_2$—O—, —O—CH$_2$—CH$_2$—O—, etc.), sulfonamide which may be substituted [for example, a group formed by bonding of amino group which may be substituted (for example, amino, mono-C$_{1-4}$ alkylamino, di-C$_{1-4}$ alkylamino, 5- or 6-membered cyclic amino such as tetrahydropyrrole, piperazine, piperidine, morpholine, thiomorpholine, pyrrole, imidazole, etc.) with —SO$_2$—, etc.], formyl, C$_{2-4}$ alkanoyl (for example, acetyl, propionyl, etc.), C$_{1-4}$ alkylsulfonyl (for example, methanesulfonyl, ethanesulfonyl, etc.), a heterocyclic group which may be substituted, and the like, and the number of the substituents is preferably 1 to 3.

The "heterocyclic group" of the "heterocyclic group which may be substituted" and the "heterocyclic group which may be substituted" represented by R$^4$, may be exemplified by a group formed by eliminating one hydrogen atom from an aromatic heterocyclic ring or a non-aromatic heterocyclic ring, and the like. Examples of such aromatic heterocyclic ring include a 5- or 6-membered aromatic heterocyclic ring containing 1 to 4 heteroatoms of one or two kinds selected from a nitrogen atom, a sulfur atom and an oxygen atom, such as furan, thiophene, pyrrole, imidazole, pyrazole, thiazole, oxazole, isothiazole, isoxazole, tetrazole, pyridine, pyrazine, pyrimidine, pyridazine, triazole, oxadiazole, thiadiazole or the like, while examples of such non-aromatic heterocyclic ring include a 5- or 6-membered non-aromatic heterocyclic ring containing 1 to 4 heteroatoms of one or two kinds selected from a nitrogen atom, a sulfur atom and an oxygen atom, such as tetrahydrofuran, tetrahydrothiophene, dioxolane, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, etc., a non-aromatic heterocyclic ring in which all or part of the bonds in the above-mentioned aromatic heterocyclic ring are saturated bonds (preferably, an aromatic heterocyclic ring such as pyrazole, thiazole, oxazole, tetrazole, etc.), and the like.

The substituent of the "heterocyclic group" of the "heterocyclic group which may be substituted" represented by $R^4$, may be exemplified by the same substituent of the "hydrocarbon group" of the "hydrocarbon group which may be substituted" represented by $R^4$.

The hydrocarbon group which may be substituted is preferably $C_{1-6}$ alkyl which may be halogenated or hydroxylated and $C_{2-6}$ alkenyl which may be halogenated or hydroxylated.

The "acyl group which may be substituted" represented by $R^4$ may be exemplified by the same one as the "acyl group which may be substituted" as the substituent which may be carried by the "5- or 6-membered ring" of the "5- or 6-membered ring which may be substituted" represented by $R^1$, and among these, $C_{1-4}$ alkylsulfonyl which may be halogenated or hydroxylated, formyl, $C_{2-5}$ alkanoyl which may be halogenated or hydroxylated, and the like are more preferred.

As for $R^4$, $C_{1-4}$ alkyl which may be halogenated or hydroxylated, formyl, $C_{2-5}$ alkanoyl which may be halogenated or hydroxylated, and the like are more preferred, and propyl, isobutyl, isobutenyl or 3-hydroxy-2-methylpropyl are particularly preferred. Another preferred embodiment of $R^4$ may be exemplified by a group represented by the formula —$(CH_2)_s$—$R^x$ wherein s is 0 or 1 and $R^x$ is a 5- or 6-membered ring which may be substituted (for example, the same one as the "5- or 6-membered ring which may be substituted" represented by $R^1$, etc.; preferably phenyl, pyridyl, pyrazolyl, thiazolyl, oxazolyl, tetrazolyl, etc., each of which may be substituted with halogen, $C_{1-4}$ alkyl which may be halogenated or hydroxylated, $C_{1-4}$ alkoxy which may be halogenated or hydroxylated, etc.), and the like.

Among these, $R^4$ is preferably 1) $C_{1-6}$ alkyl, 2) $C_{2-6}$ alkenyl, 3) $C_{6-10}$ aryl, 4) $C_{6-10}$ arylmethyl, 5) heterocyclic group and 6) heterocyclic methyl (wherein the above 1) and 2) may be substituted with halogen or hydroxy group; and the above 3), 4), 5) and 6) may be substituted with halogen, $C_{1-6}$ alkyl which may be substituted with halogen or hydroxy group, or $C_{1-6}$ alkoxy which may be substituted with halogen or hydroxy group).

n is preferably 1 or 2, and particularly preferably 2.

In formula (I) above, the "5- or 6-membered aromatic ring which may be substituted" represented by $Z^1$ may be exemplified by a 6-membered aromatic hydrocarbon such as benzene; a 5- to 6-membered aromatic heterocyclic ring containing 1 to 4 heteroatoms of one or two kinds selected from a nitrogen atom, a sulfur atom and an oxygen atom, such as furan, thiophene, pyrrole, imidazole, pyrazole, thiazole, oxazole, isothiazole, isoxazole, tetrazole, pyridine, pyrazine, pyrimidine, pyridazine, triazole, etc.; a fused aromatic heterocyclic ring such as benzofuran, indole, benzothiophene, benzoxazole, benzothiazole, indazole, benzimidazole, quinoline, isoquinoline, quinoxaline, phthalazine, quinazoline, cinnoline, imidazopyridine, etc.; and the like. Among them, preferred are benzene, furan, thiophene, pyridine, pyridazine, pyrimidine, benzimidazole and the like, and particularly preferably used are benzene, pyridine, pyridazine and benzimidazole (preferably benzene).

The "5- or 6-membered aromatic ring which may be substituted" represented by $Z^1$ may have the same substituent as the "substituent" which may be carried by the "5- or 6-membered ring" of the "5- or 6-membered ring which may be substituted" represented by $R^1$, and among the substituents, a halogen atom (for example, fluorine, chlorine, bromine, etc.), a $C_{1-4}$ alkyl group which may be substituted with halogen atom(s) (for example, methyl, ethyl, trifluoromethyl, trifluoroethyl, etc.), a $C_{1-4}$ alkoxy group which may be substituted with halogen atom(s) (for example, methoxy, ethoxy, propoxy, trifluoromethoxy, trifluoroethoxy, etc.) and the like are preferred. However, it is preferred that there is no other substituent than $X^2$ and $Z^2$, and it is preferred that when $Z^1$ is a 6-membered ring (preferably benzene), the site of substitution of $Z^2$ is para to $X^2$. Further, as for the substituent of $Z^1$, benzene which may be substituted with 1) a halogen atom, 2) a $C_{1-4}$ alkyl group which may be substituted with halogen atom(s) or 3) $C_{1-4}$ alkoxy group which may be substituted with halogen atom(s) is preferred, and in particular, benzene which may be substituted with a methyl group or a trifluoromethyl group is preferred.

In formula (I) above, with respect to the formulas -$Z^{2a}$-$W^1$-$Z^{2b}$- and -$Z^{2a}$-$W^2$-$Z^{2b}$- represented by $Z^2$, the substituent ($R^a$) of the "imino group which may be substituted" represented by each of $Z^{2a}$ and $Z^{2b}$ may be exemplified by hydrogen atom, lower ($C_{1-6}$) alkyl which may be substituted [for example, methyl, ethyl, propyl, isopropyl, butyl, isobutyl, sec-butyl, tert-butyl, pentyl, isopentyl, neopentyl, hexyl, hydroxy-$C_{1-6}$ alkyl (for example, hydroxyethyl, hydroxypropyl, hydroxybutyl, etc.), halogenated $C_{1-6}$ alkyl (for example, trifluoromethyl, trifluoroethyl, etc.), cyanated $C_{1-6}$ alkyl (for example, cyanoethyl, cyanopropyl, etc.), carboxyl-$C_{1-6}$ alkyl which may be esterified or amidated, etc.], formyl, lower ($C_{2-5}$) alkanoyl (for example, acetyl, propionyl, butyryl, etc.), lower ($C_{1-5}$) alkylsulfonyl (methylsulfonyl, ethylsulfonyl, etc.), and the like.

The alkylene chain and alkenylene chain represented by the $W^1$ and $W^2$ may be substituted at any arbitrary position (preferably on a carbon atom), and such substituent may be any substituent capable of bonding to the alkylene chain or alkenylene chain which constitutes the straight chain moiety. Examples thereof include lower ($C_{1-6}$) alkyl (for example, methyl, ethyl, propyl, isopropyl, butyl, isobutyl, sec-butyl, tert-butyl, pentyl, isopentyl, neopentyl, hexyl, etc.), lower ($C_{3-7}$) cycloalkyl (for example, cyclopropyl, cyclobutyl, cyclopentyl, cyclohexyl, cycloheptyl, etc.), formyl, lower ($C_{2-7}$) alkanoyl, (for example, acetyl, propionyl, butyryl, etc.), phosphono which may be esterified, carboxyl group which may be esterified or amidated, hydroxy group, oxo, hydroxyimino group, lower ($C_{1-6}$) alkoxyimino group which may be substituted and the like, and preferably lower alkyl having 1 to 6 carbon atoms (preferably, $C_{1-3}$ alkyl), hydroxy group, oxo, hydroxyimino group, lower ($C_{1-6}$) alkoxyimino group (which may be substituted with a polar group such as hydroxy group, cyano group, carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc.), etc.) and the like.

The alkylene chain of the "alkylene chain which may be substituted" represented by $W^1$ and $W^2$ may be exemplified by the alkylene chain represented by $-(CH_2)_{k1}-$ (wherein k1 is an integer of 1 to 4) or the like. The alkenylene chain of the "alkenylene chain which may be substituted" represented by $W^1$ may be exemplified by the alkenylene chain represented by $-(CH_2)_{k2}-(CH=CH)-(CH_2)_{k3}-$ (wherein k2 and k3 are identical or different, and represent 0, 1 or 2, respectively, provided that the sum of k2 and k3 is 2 or less) and the like.

The phosphono group which may be esterified may be exemplified by a group represented by $P(O)(OR^7)(OR^8)$ wherein $R^7$ and $R^8$ are each hydrogen, an alkyl group having 1 to 6 carbon atoms, or a cycloalkyl group having 3 to 7 carbon atoms, or $R^7$ and $R^8$ may be bonded to each other to form a 5- to 7-membered ring.

In the above-described formula, the alkyl group having 1 to 6 carbon atoms represented by $R^7$ and $R^8$ may be exemplified by methyl, ethyl, propyl, isopropyl, butyl, isobutyl, sec-butyl, tert-butyl, pentyl, isopentyl, neopentyl, hexyl and the like, and the cycloalkyl group having 3 to 7 carbon atoms may be exemplified by cyclopropyl, cyclobutyl, cyclopentyl, cyclohexyl, cycloheptyl and the like. Preferred is a chained lower alkyl having 1 to 6 carbon atoms, and more preferred is lower alkyl having 1 to 3 carbon atoms. $R^7$ and $R^8$ may be identical or different from each other, preferably identical. Further, when $R^7$ and $R^8$ are bonded to each other to form a 5- to 7-membered ring, $R^7$ and $R^8$ are bonded to each other to form a linear $C_{2-4}$ alkylene side chain represented by $-(CH_2)_2-$, $-(CH_2)_3-$ or $-(CH_2)_4-$. This side chain may be substituted, and examples of such substituent include hydroxy group, halogen and the like.

The ester derivative of the above-described carboxyl group which may be esterified may be exemplified by a derivative in which a carboxyl group is bonded to an alkyl group having 1 to 6 carbon atoms or a cycloalkyl group having 3 to 7 carbon atoms, for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, cyclopentyloxycarbonyl, cyclohexyloxycarbonyl and the like.

The amide derivative of the above-described carboxyl group which may be amidated may be exemplified by a derivative in which a carboxyl group is bonded to an alkylamino group having 1 to 6 carbon atoms, a cycloalkylamino group having 3 to 7 carbon atoms or 5- to 8-membered cyclic amine (for example, pyrrolidine, piperidine, morpholine, etc.), for example, carbamoyl, mono-$C_{1-6}$ alkylcarbamoyl, di-$C_{1-6}$ alkylcarbamoyl, cyclopentylaminocarbonyl, cyclohexylaminocarbonyl, pyrrolidinocarbonyl, piperidinocarbonyl, morpholinocarbonyl, thiomorpholinocarbonyl and the like.

For $Z^2$, preferably, one of $Z^{2a}$ and $Z^{2b}$ is O, $S(O)_m$ (wherein m is 0, 1 or 2), or $-N(R^a)-$ (wherein $R^a$ is a hydrogen atom or a lower $C_{1-4}$ alkyl group which may be substituted), the other being a bond, and W is $-(CH_2)_p-$ (wherein p is an integer of 1 to 3), or $Z^2$ is a divalent group of the formula $-CH(OH)-$. More preferably, one of $Z^{2a}$ and $Z^{2b}$ is O or $S(O)_m$ (wherein m is 0, 1 or 2), the other being a bond, and W is $-(CH_2)_p-$ (wherein p is an integer of 1 to 3), or $Z^2$ is a divalent group of the formula $-CH(OH)-$. Even more preferably, $Z^2$ is $-CH_2-$, $-CH(OH)-$, $-S(O)_m-CH_2-$ (wherein m is 0, 1 or 2), with $-S(O)_m-CH_2-$ (wherein m is 0, 1 or 2) being particularly preferred. In particular, when $Z^{2a}$ is bonded to $Z^1$, $Z^2$ is preferably $-SOCH_2-$.

$Z^{2a}$ represents a bond, S, SO or $SO_2$, and among them, SO is preferred. In this case, the configuration of SO is preferably (S).

The bonding position of $Z^2$ with respect to $Z^1$ is such that when $Z^1$ is a benzene ring for example, any position may be selected, but the para position is preferred.

In the above formula (I), the "amino group which may be substituted, in which the nitrogen atom may be converted to a quaternary ammonium or an oxide" represented by $R^2$ may be exemplified by an amino group which may have 1 or 2 substituents, an amino group which has three substituents, in which the nitrogen atom is converted to quaternary ammonium, and the like. When the amino group has two or more substituents on its nitrogen atom, the substituents may be identical or different; and when the nitrogen atom has 3 substituents, the amino group may be of any type among the following formulas, $-N^+R^pR^pR^p$, $-N^+R^pR^pR^q$, and $-N+R^pR^qR^r$, wherein $R^p$, $R^q$, and $R^r$ are different from each other, each being hydrogen or a substituent. Examples of the counter anion of the amino group, in which the nitrogen atom is converted to quaternary ammonium include, in addition to anions of halogen (for example, Cl⁻, Br⁻, I⁻, etc.), anions derived from inorganic acids such as hydrochloric acid, hydrobromic acid, nitric acid, sulfuric acid, phosphoric acid, etc.; anions derived from organic acids such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.; and anions derived from acidic amino acids such as aspartic acid, glutamic acid, etc., and among them, $Cl^1$, Br⁻, I⁻ and the like are preferred.

Examples of the substituent of the amino group include:

(1) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, and the like); and (2) cycloalkyl which may be substituted (for example, $C_{3-8}$ cycloalkyl such as cyclopropyl, cyclobutyl, cyclopentyl, cyclohexyl, cycloheptyl, cyclooctyl, etc., and the like);

(2-1) the cycloalkyl may contain one heteroatom selected from a sulfur atom, an oxygen atom and a nitrogen atom, forming oxirane, thiolane, aziridine, tetrahydrofuran, tetrahydrothiophene, pyrrolidine, tetrahydropyran, tetrahydrothiopyran, tetrahydrothiopyran-1-oxide, piperidme, etc. (preferably, a 6-membered ring such as tetrahydropyran, tetrahydrothiopyran, piperidine, etc.), and the bond with the amino group may be preferably present at the 3- or 4-position (preferably at the 4-position);

(2-2) also, the cycloalkyl may be fused to a benzene ring, forming indane (for example, indan-1-yl, indan-2-yl, etc.), tetrahydronaphthalene (for example, tetrahydronaphthalen-5-yl, tetrahydronaphthalen-6-yl, etc.), or the like (preferably, indane, etc.);

(2-3) further, the cycloalkyl may be bridged via a straight atomic chain having 1 or 2 carbon atoms, forming a bridged cyclic hydrocarbon residue such as bicyclo[2.2.1]heptyl, bicyclo[2.2.2]octyl, bicyclo[3.2.1]octyl, bicyclo[3.2.2]nonyl, etc. (preferably, cyclohexyl bridged via a straight atomic chain having 1 to 2 carbon atoms, and more preferably, bicyclo[2.2.1]heptyl, etc.);

(3) alkenyl which may be substituted (for example, alkenyl having 2 to 10 carbon atoms such as allyl, crotyl, 2-pentenyl, 3-hexenyl, etc., preferably lower ($C_{2-6}$) alkenyl, and the like);

(4) cycloalkenyl which may be substituted (for example, cycloalkenyl having 3 to 7 carbon atoms such as 2-cyclopentenyl, 2-cyclohexenyl, 2-cyclopentenylmethyl, 2-cylcohexenylmethyl, etc.);

(5) aralkyl which may be substituted (for example, phenyl-$C_{1-4}$ alkyl (for example, benzyl, phenethyl, etc.), and the like);

(6) formyl, or acyl which may be substituted (for example, alkanoyl having 2 to 4 carbon atoms (for example, acetyl, propionyl, butyryl, isobutyryl, etc.), alkylsulfonyl having 1 to 4 carbon atoms (for example, methanesulfonyl, ethanesulfonyl, etc.), alkoxycarbonyl having 1 to 4 carbon atoms (for example, methoxycarbonyl, ethoxycarbonyl, tert-butoxycarbonyl, etc.), aralkyloxycarbonyl having 7 to 10 carbon atoms (for example, benzyloxycarbonyl, etc.), and the like);

(7) aryl which may be substituted (for example, phenyl, naphthyl, etc.);

(8) a heterocyclic group which may be substituted (for example, a group formed by eliminating one hydrogen atom from a 5- or 6-membered aromatic heterocyclic ring containing 1 to 4 heteroatoms of one or two kinds selected from a nitrogen atom, a sulfur atom and an oxygen atom, such as furan, thiophene, pyrrole, imidazole, pyrazole, thiazole, oxazole, isothiazole, isoxazole, tetrazole, pyridine, pyrazine, pyrimidine, pyridazine, triazole, oxadiazole, thiadiazole, etc., or from a fused heterocyclic aromatic group such as benzofuran, indole, benzothiophene, benzoxazole, benzothiazole, indazole, benzimidazole, quinoline, isoquinoline, quinoxaline, phthalazine, quinazoline, cinnoline, imidazopyridine, etc.; a group formed by eliminating one hydrogen atom from a 5- or 6-membered non-aromatic heterocyclic ring containing 1 to 4 heteroatoms of one or two kinds selected from a nitrogen atom, a sulfur atom and an oxygen atom, such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, etc.; and the like; preferably, a group formed by eliminating a hydrogen atom from the 5- or 6-membered non-aromatic heterocyclic ring and the like; more preferably, a group formed by eliminating one hydrogen atom from a 5- or 6-membered non-aromatic heterocyclic ring containing one heteroatom, such as tetrahydrofuran, piperidine, tetrahydropyran, tetrahydrothiopyran, etc.); and the like. The substituents on the amino group may be bonded to each other to form 5- to 7-membered cyclic amino such as piperidine, piperazine, morpholine, thiomorpholine, etc.

Examples of the substituent which may be carried by the above-described (1) alkyl which may be substituted, (2) cycloalkyl which may be substituted, (3) alkenyl which may be substituted, (4) cycloalkenyl which may be substituted, (5) aralkyl which may be substituted, (6) acyl which may be substituted, (7) aryl which may be substituted, and (8) a heterocyclic group which may be substituted, include halogen (for example, fluorine, chlorine, bromine, iodine, etc.); lower ($C_{1-4}$) alkyl which may be halogenated; lower ($C_{1-4}$) alkyl which may be substituted with a polar group such as hydroxy group, a cyano group, a carboxyl group which may be esterified or amidated, etc. (for example, hydroxy-$C_{1-4}$ alkyl, cyano-$C_{1-4}$ alkyl, carboxyl-$C_{1-4}$ alkyl, $C_{1-4}$ alkoxycarbonyl-$C_{1-4}$ alkyl, carbamoyl-$C_{1-4}$ alkyl, mono-$C_{1-4}$ alkylcarbamoyl-$C_{1-4}$ alkyl, di-$C_{1-4}$ alkylcarbamoyl, di-$C_{1-4}$ alkylcarbamoyl-$C_{1-4}$ alkyl, pyrrolidinocarbonyl-$C_{1-4}$ alkyl, piperidinocarbonyl-$C_{1-4}$ alkyl, morpholinocarbonyl-$C_{1-4}$ alkyl, thiomorpholinocarbonyl-$C_{1-4}$ alkyl, etc.); $C_{1-4}$ alkoxy which may be halogenated (for example, methoxy, ethoxy, propoxy, butoxy, trifluoromethoxy, trifluoroethoxy, etc.); $C_{1-4}$ alkylenedioxy (for example, —O—$CH_2$—O—, —O—$CH_2$—$CH_2$—O—, etc.); formyl; $C_{2-4}$ alkanoyl (for example, acetyl, propionyl, etc.); $C_{1-4}$ alkylsulfonyl (for example, methanesulfonyl, ethanesulfonyl, etc.); phenyl-lower ($C_{1-4}$) alkyl; $C_{3-7}$ cycloalkyl; cyano; nitro; hydroxy group; thiol group which may be substituted (for example, thiol, $C_{1-4}$ alkylthio, etc.); amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc., and the like); carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc.); lower ($C_{1-4}$) alkoxy-carbonyl; lower ($C_{7-10}$) aralkyloxy-carbonyl; oxo group (preferably, halogen, lower ($C_{1-4}$) alkyl which may be halogenated, lower ($C_{1-4}$) alkoxy which may be halogenated, phenyl-lower ($C_{1-4}$) alkyl, $C_{3-7}$ cycloalkyl, cyano, hydroxy group, etc); and the like. The number of the substituents is preferably 1 to 3.

In the above formula (I), the "amino group which may be substituted, in which the nitrogen atom may be converted to a quaternary ammonium or an oxide" represented by $R^2$ is preferably an amino group which may have 1 to 3 substituents selected from:

(1) linear or branched lower ($C_{1-6}$) alkyl which may be substituted with one to three of halogen, cyano, hydroxy group or $C_{3-7}$ cycloalkyl;

(2) $C_{5-8}$ cycloalicyl which may be substituted with one to three of halogen, lower ($C_{1-4}$) alkyl which may be halogenated, or phenyl-lower ($C_{1-4}$) alkyl, which may contain one heteroatom selected from a sulfur atom, an oxygen atom and a nitrogen atom, which may be fused to a benzene ring, and which may be bridged via a straight atomic chain having 1 or 2 carbon atoms (for example, cyclopentyl, cyclohexyl, cycloheptyl, cyclooctyl, tetrahydropyranyl, tetrahydrothiopyranyl, piperidinyl, indanyl, tetrahydronaphthalenyl, bicyclo[2,2,1]heptyl, etc., each of which may be substituted);

(3) phenyl-lower ($C_{1-4}$) alkyl which may have one to three of halogen, lower ($C_{1-4}$) alkyl which may be halogenated, or lower ($C_{1-4}$) alkoxy which may be halogenated;

(4) phenyl which may have one to three of halogen, lower ($C_{1-4}$) alkyl which may be halogenated, or lower ($C_{1-4}$) alkoxy which may be halogenated; and (5) a 5- to 6-membered aromatic heterocyclic group which may have one to three of halogen, lower ($C_{1-4}$) alkyl which may be halogenated, lower ($C_{1-4}$) alkoxy group which may be halogenated, lower ($C_{1-4}$) alkoxy-lower ($C_{1-4}$) alkoxy which may be halogenated, phenyl-lower ($C_{1-4}$) alkyl, cyano, or hydroxy group (for example, a group formed by eliminating one hydrogen atom from furan, thiophene, pyrrole, pyridine, etc.).

In the above formula (I), the "nitrogen-containing heterocyclic ring" of the "nitrogen-containing heterocyclic group which may be substituted and which may contain a sulfur atom or an oxygen atom as the ring-constituting atom, in which the nitrogen atom may be converted to a quaternary ammonium or an oxide" represented by $R^2$, may be exemplified by a 5- to 6-membered aromatic heterocyclic ring containing 1 to 4 heteroatoms of one or two kinds selected from a nitrogen atom, a sulfur atom and an oxygen atom, such as pyrrole, imidazole, pyrazole, thiazole, oxazole, isothiazole, isoxazole, tetrazole, pyridine, pyrazine, pyrimidine, pyridazine, triazole, oxadiazole, thiadiazole, etc. or a fused aromatic heterocyclic ring such as benzofuran, indole, benzothiophene, benzoxazole, benzothiazole, indazole, benzimidazole, quinoline, isoquinoline, quinoxaline, phthalazine, quinazoline, cinnoline, imidazopyridine, etc.; a 5- to 8-membered non-aromatic heterocyclic ring containing a nitrogen atom and additionally 1 to 3 heteroatoms of one or two kinds selected from a nitrogen atom, a sulfur atom and an oxygen atom, such as pyrrolidine, pyrroline, imidazolidine, imidazoline, pyrazolidine, pyrazoline, piperidine, piperazine, oxazine, oxadiazine, thiazine, thiadiazine, morpholine, thiomorpholine, azacycloheptane, azacyclooctane (azocane), etc.; or the like, and these nitrogen-containing heterocyclic rings may be bridged via a straight atomic chain having 1 or 2 carbon atoms, forming a bridged-ring nitrogen-containing heterocyclic ring such as azabicyclo[2.2.1]heptane, azabicyclo[2.2.2]octane (quinuclidine), etc. (preferably, piperidine bridged via a straight atomic chain having 1 or 2 carbon atoms, etc.).

Among specific examples of the above-described nitrogen-containing heterocyclic ring, preferred are pyridine, pyridazine, pyrazole, imidazole, triazole, tetrazole, imidazopyridine, pyrrolidine, piperidine, piperazine, morpholine, thiomorpholine and azabicyclo[2. 2.2]octane (preferably, pyridine, imidazole, triazole, imidazopyridine, pyrrolidine, piperidine and morpholine).

The nitrogen atom of the "nitrogen-containing heterocyclic ring" may be converted to a quaternary ammonium or an oxide. When the nitrogen atom of the "nitrogen-containing heterocyclic ring" is converted to a quaternary ammonium, the counter anion of the "nitrogen-containing heterocyclic group, in which the nitrogen atom is converted to a quaternary ammonium" may be exemplified by, in addition to anions of halogen (for example, Cl⁻, Br⁻, I⁻, etc.), anions derived from inorganic acids such as hydrochloric acid, hydrobromic acid, nitric acid, sulfuric acid, phosphoric acid, etc.; anions derived from organic acids such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.; anions derived from acidic amino acids such as aspartic acid, glutamic acid, etc.; and the like, and among them, Cl⁻, Br⁻, I⁻ and the like are preferred.

The "nitrogen-containing heterocyclic group" may be bonded to a divalent group represented by $Z^2$ via a carbon atom or a nitrogen atom, and may be bonded to a ring-constituting carbon atom as in 2-pyridyl, 3-pyridyl, 2-piperidinyl, etc., or to a ring-constituting nitrogen atom as in the following:

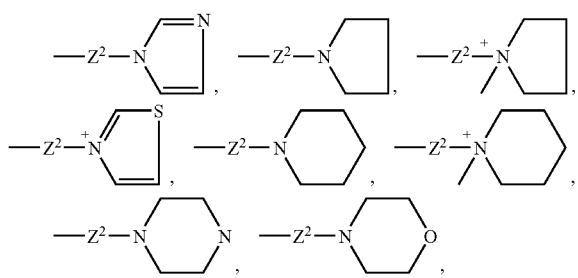

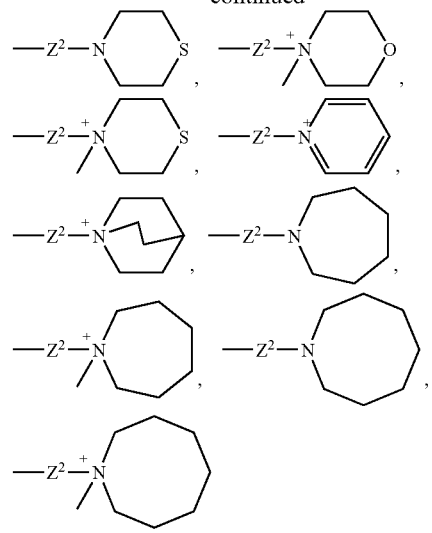

The substituent which may be carried by the "nitrogen-containing heterocyclic ring" may be exemplified by halogen (for example, fluorine, chlorine, bromine, iodine, etc.), lower ($C_{1-4}$) alkyl which may be substituted, lower ($C_{1-4}$) alkoxy which may be substituted, phenyl which may be substituted, monophenyl- or diphenyl-lower ($C_{1-4}$) alkyl which may be substituted, $C_{3-7}$ cycloalkyl which may be substituted, cyano, nitro, hydroxy group, thiol group which may be substituted (for example, thiol, $C_{1-4}$ alkylthio, etc.), amino group which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., and the like); carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc.); lower ($C_{1-4}$) alkoxy-carbonyl; formyl; lower ($C_{2-4}$) alkanoyl; lower ($C_{14}$) alkylsulfonyl; a heterocyclic group which may be substituted (for example, a 5- to 6-membered aromatic heterocyclic ring containing 1 to 4 heteroatoms of one or two kinds selected from a nitrogen atom, a sulfur atom and an oxygen atom such as furan, thiophene, pyrrole, imidazole, pyrazole, thiazole, oxazole, isothiazole, isoxazole, tetrazole, pyridine, pyrazine, pyrimidine, pyridazine, triazole, oxadiazole, thiadiazole, etc.); a group formed by eliminating one hydrogen atom form a fused aromatic heterocyclic ring containing 1 to 4 heteroatoms of one or two kinds selected from a nitrogen atom, a sulfur atom and an oxygen atom, such as benzofuran, indole, benzothiophene, benzoxazole, benzothiazole, indazole, benzimidazole, quinoline, isoquinoline, quinoxaline, phthalazine, quinazoline, cinnoline, imidazopyridine, etc.; a group formed by eliminating one hydrogen atom from a 5- to 6-membered non-aromatic heterocyclic ring containing 1 to 4 heteroatoms of one or two kinds selected from a nitrogen atom, a sulfur atom and an oxygen atom, such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, tetrahydrothiopyran, etc.; and the like, and the number of the substituents is preferably 1 to 3. The nitrogen atom in the "nitrogen-containing heterocyclic ring" may be oxidized.

Examples of the substituent which may be carried by the "lower ($C_{1-4}$) alkyl which may be substituted", the "lower ($C_{1-4}$) alkoxy which may be substituted", the "phenyl which may be substituted", the "monophenyl- or diphenyl-lower ($C_{1-4}$) alkyl which may be substituted", the "$C_{3-7}$ cycloalkyl which may be substituted", and the "heterocyclic group which may be substituted", all of which are the substituents which may be carried by the "nitrogen-containing heterocyclic ring", include halogen (for example, fluorine, chlorine, bromine, iodine, etc.); lower ($C_{1-4}$) alkyl which may be halogenated; lower ($C_{1-4}$) alkyl which may be substituted with a polar group such as hydroxy group, cyano group, carboxyl group which may be esterified or amidated, etc. (for example, hydroxy $C_{1-4}$ alkyl, cyano $C_{1-4}$ alkyl, carboxyl $C_{1-4}$ alkyl, $C_{1-4}$ alkoxycarbonyl $C_{1-4}$ alkyl, carbamoyl $C_{1-4}$ alkyl, mono-$C_{1-4}$ alkylcarbamoyl $C_{1-4}$ alkyl, di-$C_{1-4}$ alkylcarbamoyl $C_{1-4}$ alkyl, pyrrolidinocarbonyl $C_{1-4}$ alkyl, piperidinocarbonyl $C_{1-4}$ alkyl, morpholinocarbonyl $C_{1-4}$ alkyl, thiomorpholinocarbonyl $C_{1-4}$ alkyl, etc.); lower ($C_{3-10}$) cycloalkyl; lower ($C_{3-10}$) cycloalkenyl; $C_{1-4}$ alkoxy which may be halogenated (for example, methoxy, ethoxy, trifluoromethoxy, trifluoroethoxy, etc.); formyl; $C_{2-4}$ alkanoyl (for example, acetyl, propionyl, etc.); $C_{1-4}$ alkylsulfonyl (for example, methanesulfonyl, ethanesulfonyl, etc.); $C_{1-3}$ alkylenedioxy (for example, methylenedioxy, ethylenedioxy, etc.); cyano; nitro; hydroxy group; thiol group which may be substituted (for example, thiol, $C_{1-4}$ alkylthio groups, etc.); amino group which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc., and the like); carboxyl group which may be esterified or amidated (for example, carboxyl, $C_{1-4}$ alkoxy-carbonyl, carbamoyl, mono-$C_{1-4}$ alkylcarbamoyl, di-$C_{1-4}$ alkylcarbamoyl, etc.); lower ($C_{1-4}$) alkoxycarbonyl; and the like, and the number of the substituents is preferably 1 to 3.

In the above formula (I), examples of the substituent which may be carried by the "nitrogen-containing heterocyclic ring" of the "nitrogen-containing heterocyclic ring of the heterocyclic ring which may be substituted and which may contain a sulfur atom or an oxygen atom as a ring-constituting atom, in which the nitrogen atom may be converted to a quaternary ammonium or an oxide" preferably include (1) halogen, (2) cyano, (3) hydroxy group, (4) carboxyl group, (5) carbamoyl group, (6) lower ($C_{1-4}$) alkoxy-carbonyl, (7) lower ($C_{1-4}$) alkylcarbamoyl or 5- or 6-membered cyclic amino (e.g., piperidino, morpholino, etc.)-carbonyl, (8) lower ($C_{1-4}$) alkyl which may be substituted with halogen, hydroxy group, cyano group, lower ($C_{1-4}$) alkoxy, or carboxyl which may be esterified or amidated, (9) lower ($C_{1-4}$) alkoxy which may be substituted by halogen, hydroxy group or lower ($C_{1-4}$) alkoxy, (10) phenyl which may be substituted by halogen, lower ($C_{1-4}$) alkyl, hydroxy group, lower ($C_{1-4}$) alkoxy or $C_{1-3}$ alkylenedioxy, (11) monophenyl- or diphenyl-lower ($C_{1-4}$) alkyl which may be substituted with halogen, lower ($C_{1-4}$) alkyl, hydroxy group, lower ($C_{1-4}$) alkoxy or $C_{1-3}$ alkylenedioxy, (12) a group formed by eliminating one hydrogen atom form a 5- or 6-membered aromatic heterocyclic ring such as furan, thiophene, pyrrole, pyridine, etc., and the like.

In the group represented by the formula (a) of $R^2$ in the above formula (I), examples of the "hydrocarbon group which may be substituted" represented by $R^5$ and $R^6$ include:

(1) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, and the like);

(2) cycloalkyl which may be substituted (for example, $C_{3-7}$ cycloalkyl such as cyclopropyl, cyclobutyl, cyclopentyl, cyclohexyl, cycloheptyl, etc., and the like);

(3) alkenyl which may be substituted (for example, alkenyl having 2 to 10 carbons such as allyl, crotyl, 2-pentenyl, 3-hexenyl, etc., preferably lower ($C_{2-6}$) alkenyl, and the like);

(4) cycloalkenyl which may be substituted (for example, cycloalkenyl having 3 to 7 carbons such as 2-cyclopentenyl, 2-cyclohexenyl, 2-cyclopentenylmethyl, 2-cyclohexenylmethyl, etc., and the like);

(5) alkynyl which may be substituted (for example, alkynyl having 2 to 10 carbons such as ethynyl, 1-propynyl, 2-propynyl, 1-butynyl, 2-pentynyl, 3-hexynyl, etc., preferably lower ($C_{2-6}$) alkynyl, and the like);

(6) aralkyl which may be substituted (for example, phenyl-$C_{1-4}$ alkyl (for example, benzyl, phenethyl, etc.), and the like);

(7) aryl which may be substituted (for example, phenyl, naphthyl, etc.); and the like. Examples of the substituent which may be carried by the above-described (1) alkyl which may be substituted, (2) cycloalkyl which may be substituted, (3) alkenyl which may be substituted, (4) cycloalkenyl which may be substituted, (5) alkynyl which may be substituted, (6) aralkyl which may be substituted, and (7) aryl which may be substituted include halogen (for example, fluorine, chlorine, bromine, iodine, etc.); nitro; cyano; hydroxy group; thiol group which may be substituted (for example, thiol, $C_{1-4}$ alkylthio, etc.); amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc., and the like); carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc,); $C_{1-4}$ alkyl which may be halogenated (for example, trifluoromethyl, methyl, ethyl, etc.); $C_{1-4}$ alkoxy which may be halogenated (for example, methoxy, ethoxy, trifluoromethoxy, trifluoroethoxy, etc.); formyl; $C_{2-4}$ alkanoyl (for example, acetyl, propionyl, etc.); $C_{1-4}$ alkylsulfonyl (for example, methanesulfonyl, ethanesulfonyl, etc.); and the like, and the number of the substituents is preferably 1 to 3.

Examples of the "hydroxy group which may be substituted" represented by $R^5$ and $R^6$ include hydroxy group which may have a substituent selected from:

(1) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, and the like);

(2) cycloalkyl which may be substituted (for example, $C_{3-7}$ cycloalkyl such as cyclopropyl, cyclobutyl, cyclopentyl, cyclohexyl, cycloheptyl, etc., and the like);

(3) alkenyl which may be substituted (for example, alkenyl having 2 to 10 carbons such as allyl, crotyl, 2-pentenyl, 3-hexenyl, etc., preferably lower ($C_{2-6}$) alkenyl, and the like);

(4) cycloalkenyl which may be substituted (for example, cycloalkenyl having 3 to 7 carbons such as 2-cyclopentenyl, 2-cyclohexenyl, 2-cyclopentenylmethyl, 2-cyclohexenylmethyl, etc., and the like);

(5) aralkyl which may be substituted (for example, phenyl-$C_{1-4}$ alkyl (for example, benzyl, phenethyl, etc.) and the like);

(6) formyl or acyl which may be substituted (for example, alkanoyl having 2 to 4 carbons (for example, acetyl, propionyl, butyryl, isobutyryl, etc.), alkylsulfonyl having 1 to 4 carbons (for example, methanesulfonyl, ethanesulfonyl, etc.), and the like);

(7) aryl which may be substituted (for example, phenyl, naphthyl, etc.); and the like.

Examples of the substituent which may be carried by the above-described (1) alkyl which may be substituted, (2) cycloalkyl which may be substituted, (3) alkenyl which may be substituted, (4) cycloalkenyl which may be substituted, (5) aralkyl which may be substituted, (6) acyl which may be substituted, and (7) aryl which may be substituted include halogen (for example, fluorine, chlorine, bromine, iodine, etc.); nitro; cyano; hydroxy group; thiol group which may be substituted (for example, thiol, $C_{1-4}$ alkylthio, etc.); amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc., and the like); carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc,); $C_{1-4}$ alkyl which may be halogenated (for example, trifluoromethyl, methyl, ethyl, etc.); $C_{1-4}$ alkoxy which may be halogenated (for example, methoxy, ethoxy, trifluoromethoxy, trifluoroethoxy, etc.); formyl; $C_{2-4}$ alkanoyl (for example, acetyl, propionyl, etc.); $C_{1-4}$ alkylsulfonyl (for example, methanesulfonyl, ethanesulfonyl, etc.); and the like, and the number of the substituents is preferably 1 to 3.

In the above formula, $R^5$ and $R^6$ may be bonded to each other to form a ring together with the adjacent phosphorus atom (preferably, a 5- to 7-membered ring). Such ring may be substituted and examples of the substituent include halogen (for example, fluorine, chlorine, bromine, iodine, etc.); nitro; cyano; hydroxy group; thiol group which may be substituted (for example, thiol, $C_{1-4}$ alkylthio, etc.); amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc., and the like); carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc,); $C_{1-4}$ alkyl which may be halogenated (for example, trifluoromethyl, methyl, ethyl, etc.); $C_{1-4}$ alkoxy which may be halogenated (for example, methoxy, ethoxy, trifluoromethoxy, trifluoroethoxy, etc.); formyl; $C_{2-4}$ alkanoyl (for example, acetyl, propionyl, etc.); $C_{1-4}$ alkylsulfonyl (for example, methanesulfonyl, ethanesulfonyl, etc.); and the like, and the number of the substituents is preferably 1 to 3.

In the above formula (I), when the phosphorus atom forms a phosphonium salt, examples of the counter anion include, in addition to anions of halogen (for example, Cl$^-$, Br$^-$, I$^-$, etc.), anions derived from inorganic acids such as hydrochloric acid, hydrobromic acid, nitric acid, sulfuric acid, phosphoric acid, etc.; anions derived from organic acids such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.; and anions derived from acidic amino acids such as aspartic acid, glutamic acid, etc., and among them, Cl$^-$, Br$^-$, I$^-$ and the like are preferred.

Examples of amino group which may be substituted represented by $R^5$ and $R^6$ include amino group which may have 1 or 2 substituents selected from:

(1) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, and the like);

(2) cycloalkyl which may be substituted (for example, $C_{3-7}$ cycloalkyl such as cyclopropyl, cyclobutyl, cyclopentyl, cyclohexyl, cycloheptyl, etc., and the like);

(3) alkenyl which may be substituted (for example, alkenyl having 2 to 10 carbons such as allyl, crotyl, 2-pentenyl, 3-hexenyl, etc., preferably lower ($C_{2-6}$) alkenyl and the like);

(4) cycloalkenyl which may be substituted (for example, cycloalkenyl having 3 to 7 carbons such as 2-cyclopentenyl, 2-cyclohexenyl, 2-cyclopentenylmethyl, 2-cyclohexenylmethyl, etc., and the like);

(5) formyl, or acyl which may be substituted (for example, alkanoyl having 2 to 4 carbons (for example, acetyl, propionyl, butyryl, isobutyryl, etc.), and alkylsulfonyl having 1 to 4 carbons (for example, methanesulfonyl, ethanesulfonyl, etc.), and the like);

(6) aryl which may be substituted (for example, phenyl, naphthyl, etc.); and the like.

Examples of the substituent which may be carried by the above-described (1) alkyl which may be substituted, (2) cycloalkyl which may be substituted, (3) alkenyl which may be substituted, (4) cycloalkenyl which may be substituted, (5) acyl which may be substituted, and (6) aryl which may be substituted include halogen (for example, fluorine, chlorine, bromine, iodine, etc.); nitro; cyano; hydroxy group; thiol group which may be substituted (for example, thiol, $C_{1-4}$ alkylthio, etc.); amino group which may be substituted (for example, amino, mono-$C_{1-4}$ alkylamino, di-$C_{1-4}$ alkylamino, 5- or 6-membered cyclic amino such as tetrahydropyrrole, piperazine, piperidine, morpholine, thiomorpholine, pyrrole, imidazole, etc., and the like); carboxyl group which may be esterified or amidated (for example, carboxyl, $C_{1-4}$ alkoxycarbonyl, carbamoyl, mono-$C_{1-4}$ alkylcarbamoyl, di-$C_{1-4}$ alkylcarbamoyl, etc,); $C_{1-4}$ alkyl which may be halogenated (for example, trifluoromethyl, methyl, ethyl, etc.); $C_{1-4}$ alkoxy which may be halogenated (for example, methoxy, ethoxy, trifluoromethoxy, trifluoroethoxy, etc.); formyl; $C_{2-4}$ alkanoyl (for example, acetyl, propionyl, etc.); $C_{1-4}$ alkylsulfonyl (for example, methanesulfonyl, ethanesulfonyl, etc.); and the like, and the number of the substituents is preferably 1 to 3.

The substituent of the "amidino group which may be substituted" and the "guanidino group which may be substituted" represented by $R^2$ may be the same substituent as that of the "amino group which may be substituted, in which the nitrogen atom may be converted to a quaternary ammonium or an oxide" represented by $R^2$ above.

$R^2$ is preferably (1) an amino group which may be substituted, in which the nitrogen atom may be converted to a quaternary ammonium or an oxide; (2) a nitrogen-containing heterocyclic group which may be substituted and may contain a sulfur atom or an oxygen atom as a ring-constituting atom, in which the nitrogen atom may be converted to a quaternary ammonium or an oxide; (3) an amidino group which may be substituted; or (4) a guanidino group which may be substituted; $R^2$ is more preferably the amino group which may be substituted, in which the nitrogen atom may be converted to a quaternary ammonium; and the nitrogen-containing heterocyclic group which may be substituted and which may contain a sulfur atom or an oxygen atom as the ring-constituting atom and which may be an oxide, and particularly preferably the amino group which may be substituted, the nitrogen-containing heterocyclic group which may be substituted and may contain a sulfur atom or an oxygen atom as the ring-constituting atom, etc.

$R^2$ is further more preferably a group of the formula —NRR" or —N⁺RR'R" (wherein, R, R' and R" are each an aliphatic hydrocarbon group (a chained aliphatic hydrocarbon group or a cyclic aliphatic hydrocarbon group) or an alicyclic (non-aromatic) heterocyclic group which may be substituted), or a nitrogen-containing aromatic heterocyclic group which may be substituted, in which the nitrogen atom may be converted to an oxide.

The "aliphatic hydrocarbon group which may be substituted" and "the alicyclic heterocyclic group which may be substituted" represented by R, R' and R" in the above formula may be the same "aliphatic hydrocarbon group which may be substituted (for example, alkyl, cycloalkyl, alkenyl, cycloalkenyl, etc., each of which may be substituted)" and the "alicyclic heterocyclic group which may be substituted (for example, 5- or 6-membered non-aromatic heterocyclic ring which may be substituted, etc.)" as those exemplified with respect to the substituent which may be carried by the "amino group which may be substituted" represented by $R^2$.

Among them, each of R and R' is preferably a chained hydrocarbon group which may be substituted (for example, alkyl, alkenyl, etc., each of which may be substituted), more preferably $C_{1-6}$ alkyl which may be substituted, and particularly preferably methyl which may be substituted.

R" is preferably an alicyclic hydrocarbon group which may be substituted (preferably, $C_{3-8}$ cycloalkyl which may be substituted, and more preferably cyclohexyl which may be substituted), or an alicyclic heterocyclic group which may be substituted (preferably, a saturated alicyclic heterocyclic group (preferably, a 6-membered ring) which may be substituted; more preferably, tetrahydropyranyl which may be substituted, tetrahydrothiopyranyl which may be substituted, or piperidyl which may be substituted; and particularly preferably tetrahydropyranyl which may be substituted).

The "nitrogen-containing aromatic heterocyclic group" of the "nitrogen-containing aromatic heterocyclic group which may be substituted, in which the nitrogen atom may be converted to an oxide" represented by $R^2$ includes preferably pyridine, imidazole, triazole, and imidazopyridine, particularly imidazole and triazole being preferred.

Examples of the "amino group which may be substituted, in which the nitrogen atom may be converted to a quaternary ammonium or an oxide", etc. represented by $R^{2'}$ and $R^{2''}$ include the corresponding same groups as those exemplified with respect to the above $R^2$, respectively.

The following compounds are preferred examples of the compound represented by the formula (I):

3-[4-(2-butoxyethoxy)phenyl]-10-isobutyl-N-[4-[[(1-propyl-1H-imidazol-5-yl)methyl]sulfinyl]phenyl]-7,8,9,10-tetrahydropyrido[2,3-b]azocine-6-carboxamide;

3-[4-(2-butoxyethoxy)phenyl]-10-propyl-N-[4-[[(1-propyl-1H-imidazol-5-yl)methyl]sulfinyl]phenyl]-7,8,9,10-tetrahydropyrido[2,3-b]azocine-6-carboxamide;

3-[4-(2-butoxyethoxy)phenyl]-9-isobutyl-N-[4-[[(1-propyl-1H-imidazol-5-yl)methyl]sulfinyl]phenyl]-7,8-dihydropyrido[2,3-b]azepine-6-carboxamide;

3-[4-(2-butoxyethoxy)phenyl]-9-propyl-N-[4-[[(1-propyl-1H-imidazol-5-yl)methyl]sulfinyl]phenyl]-7,8-dihydropyrido[2,3-b]azepine-6-carboxamide;

(S)-3-[4-(2-butoxyethoxy)phenyl]-10-isobutyl-N-[4-[[(1-propyl-1H-imidazol-5-yl)methyl]sulfinyl]phenyl]-7,8,9,10-tetrahydropyrido[2,3-b]azocine-6-carboxamide;

(S)-3-[4-(2-butoxyethoxy)phenyl]-10-propyl-N-[4-[[(1-propyl-1H-imidazol-5-yl)methyl]sulfinyl]phenyl]-7,8,9,10-tetrahydropyrido[2,3-b]azocine-6-carboxamide;

(S)-3-[4-(2-butoxyethoxy)phenyl]-9-isobutyl-N-[4-[[(1-propyl-1H-imidazol-5-yl)methyl]sulfinyl]phenyl]-7,8-dihydropyrido[2,3-b]azepine-6-carboxamide;

(S)-3-[4-(2-butoxyethoxy)phenyl]-9-propyl-N-[4-[[(1-propyl-1H-imidazol-5-yl)methyl]sulfinyl]phenyl]-7,8-dihydropyrido[2,3-b]azepine-6-carboxamide;

3-[4-(2-butoxyethoxy)phenyl]-1-isobutyl-N-[4-[[N-methyl-N-(tetrahydropyran-4-yl)amino]methyl]phenyl]-7,8,9,10-tetrahydropyrido[2,3-b]azocine-6-carboxamide; and the like.

A salt of the compound represented by the formula (I) of the present invention is preferably a pharmaceutically acceptable salt. Examples of the salt include salts with inorganic bases, salts with organic bases, salts with inorganic acids, salts with organic acids, salts with basic or acidic amino acids; and the like. Suitable examples of the salts with the inorganic bases include alkali metal salts such as a sodium salt, a potassium salt, etc.; alkaline earth metal salts such as a calcium salt, a magnesium salt, etc.; an aluminum salt; an ammonium salt; etc. Suitable examples of the salts with the organic bases include salts with trimethylamine, triethylamine, pyridine, picoline, ethanolamine, diethanolamine, triethanolamine, dicyclohexylamine, N,N'-dibenzylethylenediamine, etc. Suitable examples of the salts with the inorganic acids include salts with hydrochloric acid, hydrobromic acid, nitric acid, sulfuric acid, phosphoric acid, etc. Suitable examples of the salts with the organic acids include salts such as formate, acetate, trifluoroacetate, fumarate, oxalate, tartrate, maleate, citrate, succinate, malate, methanesulfonate, benzenesulfonate, p-toluenesulfonate, etc. Suitable examples of the salts with basic amino acids include salts with arginine, lysine, ornithine, etc. Suitable examples of the salts with acidic amino acids include salts with aspartic acid, glutamic acid, etc. The compound represented by the formula (I) of the present invention may be either a hydrate or a non-hydrate. When the compound represented by the formula (I) of the present invention is present as a mixture of configurational isomers, diastereomers, or conformers, the compound may be isolated by separation and purification methods known in the art, if desired. When the compound represented by the formula (I) is present as a racemate, each of (S) and (R) isomers may be separated by general means for optical resolution. Each of the optical isomers as well as the racemate is included in the scope of the present invention.

The prodrug of the compound represented by formula (I) used in the invention or a salt thereof [hereinafter, may be sometimes referred to as Compound (I)] refers to a compound which is converted to Compound (I) by an in vivo reaction caused by an enzyme, gastric acid or the like under physiological conditions, that is, a compound which is converted to Compound (I) upon occurrence of enzymatic oxidation, reduction, hydrolysis or the like, or a compound which is converted to Compound (I) upon occurrence of hydrolysis or the like by gastric acid or the like. The prodrug of Compound (I) may be exemplified by compounds resulting from acylation, alkylation or phosphorylation of the amino group of Compound (I) (for example, the compounds in which the amino group of Compound (I) is in the form of eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl or the like); compounds resulting from acylation, alkylation, phosphorylation or boration of the hydroxy group of Compound (I) (for example, the compounds in which the hydroxy group of Compound (I) is in the form of acetyl, palmitoyl, propanoyl, pivaloyl, succinyl, fumaryl, alanyl, dimethylaminomethylcarbonyl or the like); compounds resulting from esterification or amidation of the carboxyl group of Compound (I) (for example, the compounds in which the carboxyl group of Compound (I) is in the form of ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide or the like); or the like. These compounds can be prepared from Compound (I) by methods known per se in the art.

Furthermore, the prodrug of Compound (I) may be also a compound which is converted to Compound (I) under physiological conditions, as described in "Development of Pharmaceutical Products", Vol. 7 Design of Molecules, Hirokawa Publisher, pp. 163-198 (1990).

Also, Compound (I) may be labeled with isotopes (for example, $^3$H, $^4$C, $^{35}$S, $^{125}$I, etc.).

Hereinafter, a process for producing the compound represented by the formula (I) or a salt thereof will be explained.

The compound represented by the formula (I) or the salt thereof can be produced by processes known per se. For example, it can be produced by the following processes. Alternatively, the compound represented by the formula (I) or the salt thereof may be produced by the process described in JP-A No. 8-73476 or a similar method thereto.

The compounds which will be used in each of the following processes may form salts similar to the salt of Compound (I), as far as the salts do not interfere with the reactions.

Further, in the following reactions, when the starting compounds have amino, carboxyl or hydroxy groups as substituents, these groups may be protected by protective groups which are commonly used in peptide chemistry, and if necessary, the protective groups can be removed after the reactions to obtain desired compounds.

Examples of the protective group for an amino group include a $C_{1-6}$ alkylcarbonyl which may be substituted (for example, acetyl, propionyl, etc.), formyl, phenylcarbonyl, a $C_{1-6}$ alkyloxycarbonyl (for example, methoxycarbonyl, ethoxycarbonyl, t-butoxycarbonyl, etc.), phenyloxycarbonyl (for example, benzoxycarbonyl, etc.), a $C_{7-10}$ aralkyloxycarbonyl (for example, benzyloxycarbonyl, etc.), trityl, phthaloyl and the like. The substituents of these protective groups include a halogen atom (for example, fluorine, chlorine, bromine, iodine, etc.), a $C_{1-6}$ alkylcarbonyl (for example, acetyl, propionyl, butyryl, etc.), a nitro group and the like, and the number of-the substituents is about 1 to 3.

Examples of the protective group to be used for a carboxyl group include a $C_{1-6}$ alkyl which may be substituted (for example, methyl, ethyl, propyl, isopropyl, butyl, tert-butyl, etc.), phenyl, trityl, silyl and the like. The substituents of these protective groups include a halogen atom (for example fluorine, chlorine, bromine, iodine, etc.), a $C_{1-6}$ alkylcarbonyl (for example, acetyl, propionyl, butyryl, etc.), formyl, a nitro group and the like, and the number of the substituents is about 1 to 3.

Examples of the protective groups to be used for a hydroxy group include a $C_{1-6}$ alkyl which may be substituted (for example, methyl, ethyl, propyl, isopropyl, butyl, tert-butyl, etc.), phenyl, $C_{7-10}$ aralkyl (for example, benzyl, etc.), a $C_{1-6}$ alkylcarbonyl (for example, acetyl, propionyl, etc.), formyl, phenyloxycarbonyl, a $C_{7-10}$ aralkyloxycarbonyl (for example, benzyloxycarbonyl, etc.), pyranyl, furanyl, silyl and the like. The substituents of these protective groups include a halogen atom (for example, fluorine, chlorine, bromine, iodine, etc.), a $C_{1-6}$ alkyl, phenyl, a $C_{7-10}$ aralkyl, a nitro group and the like, and the number of the substituents is about 1 to 4.

Introduction and removal of protective groups are carried out according to methods known per se or similar methods thereto [for example, the method described in "Protective Groups in Organic Chemistry", (J. F. W. McOmie et al., Plenum Press)], and removal is carried out by, for example, a method comprising treating with an acid, a base, reduction, ultraviolet light, hydrazine, phenylhydrazine, sodium N-methydithiocarbamate, tetrabutylammonium fluoride, palladium acetate, or the like.

In the following description, the compounds represented by the formulas (I), (Ia), (Ib), (II) and (III) including their salts may be also simply referred to as Compound (I), Compound (Ia), Compound (Ib), Compound (II) and Compound (III).

[Process A]

Compound (I) can be prepared by reacting Compound (II) with Compound (III) according to the following reaction:

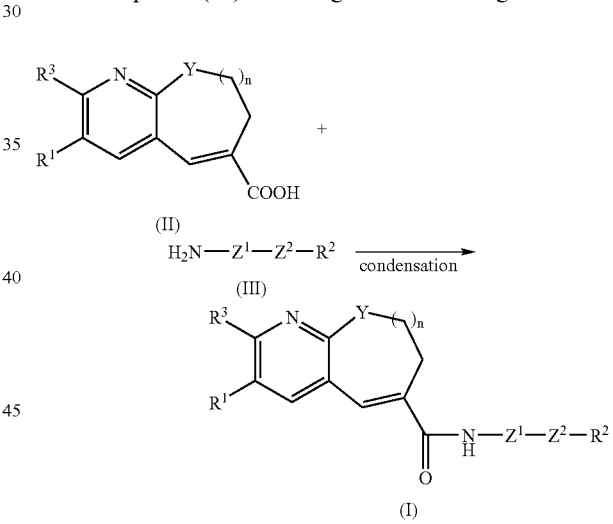

wherein each symbol has the same meaning as defined above.

In this reaction, a carboxylic acid derivative (II) is reacted with an amine derivative (III) to prepare Compound (I).

The condensation reaction of Compound (II) and Compound (III) is conducted by a conventional means for peptide synthesis. The means for peptide synthesis may be carried out according to any method known in the art, for example, the methods described in M. Bodansky and M. A. Ondetti, Peptide Synthesis, Interscience, New York (1966); F. M. Finn and K. Hofmann, The Proteins, Vol. 2; H. Nenrath and R. L. Hill, Ed., Academic Press Inc., New York (1976); and Nobuo Izumiya et al. Foundations and Experiments in Peptide Synthesis, Maruzen Co. (1985) and the like, which include, for example, azide method, chloride method, acid anhydride method, mixed acid anhydride method, DCC method, activated ester method, method using Woodward's reagent K, carbonyldiimidazole method, oxidation/reduction method, DCC/HONB method, as well as WSC method, diethyl cyanophosphate (DEPC) method and the like. In other words, examples of the reactive derivatives that may be used include acid halides (for example, acid chloride, acid bromide, etc.), acid azides, acid anhydrides, mixed acid anhydrides [for example, mixed acid anhydrides of a mono-$C_{1-6}$ alkylcarbonic acid (for example, mixed acid anhydrides of a free acid with monomethylcarbonic acid, monoethylcarbonic acid, monoisopropylcarbonic acid, monoisobutylcarbonic acid, mono-tert-butylcarbonic acid, monobenzylcarbonic acid, mono(p-nitrobenzyl)carbonic acid, or monoallylcarbonic acid, etc.), mixed acid anhydrides of a $C_{1-6}$ aliphatic carboxylic acid (for example, mixed acid anhydrides of a free acid with acetic acid, trichloroacetic acid, cyanoacetic acid, propionic acid, butyric acid, isobutyric acid, valeric acid, isovaleric acid, pivalic acid, trifluoroacetic acid, trichloroacetic acid, acetoacetic acid, etc.), mixed acid anhydrides of a $C_{7-12}$ aromatic carboxylic acid (for example, mixed acid anhydrides of a free acid with benzoic acid, p-toluic acid, p-chlorobenzoic acid, etc.), mixed acid anhydrides of organic sulfonic acid (for example, mixed acid anhydrides of a free acid with methanesulfonic acid, ethanesulfonic acid, benzenesulfonic acid, p-toluenesulfonic acid, etc.) etc.], activated amides, activated esters (for example, diethoxyphosphoric acid ester, diphenoxyphosphoric acid ester, p-nitrophenyl ester, 2,4-dinitrophenyl ester, etc.), activated thioesters (for example, 2-pyridylthiol ester, 2-benzothiazolylthiol ester, etc.) and the like. This condensation reaction can be carried out in a solvent. Examples of the solvent include N,N-dimethylformamide, dimethylsulfoxide, pyridine, chloroform, dichloromethane, tetrahydrofuran, dioxane, acetonitrile, each of which is dehydrated or hydrated, or appropriate mixtures thereof. The reaction temperature is usually about −20° C. to about 50° C., and preferably about −10° C. to about 30° C. The reaction time is about 1 to about 100 hours, and preferably about 2 to about 40 hours. The thus-obtained Compound (I) can be isolated and purified by known separation and purification means such as concentration, vacuum concentration, solvent extraction, crystallization, recrystallization, redissolution, chromatography or the like.

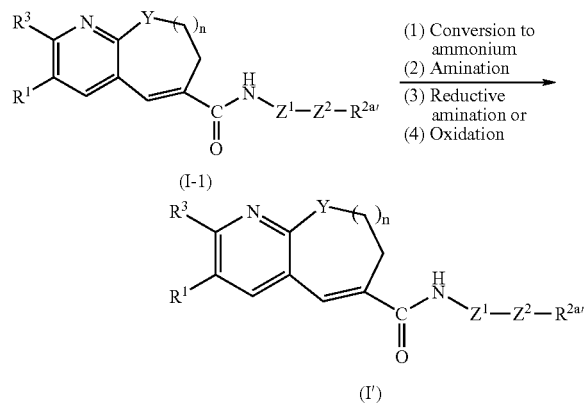

(1) When $R^{2a}$ as represented in Compound (I-1) is, for example, a tertiary amine residue, Compound (I-1) can be reacted with an alkyl halide or an aralkyl halide to prepare a quaternized Compound (I'). Herein, examples of the halogen atom include chlorine, bromine, iodine, etc., and the alkyl halide (for example, lower ($C_{1-6}$) alkyl halide, etc.), or the aralkyl halide (for example, lower ($C_{1-4}$) alkyl-phenyl halide, etc.) is typically used in an amount of about 1 to 5 moles with respect to 1 mole of Compound (I-1). The reaction can be carried out in an inert solvent, for example, toluene, benzene, xylene, dichloromethane, chloroform, 1,2-dichloroethane, dimethylformamide (DMF), dimethylacetamide, etc., or a mixture of the solvents above. The reaction temperature is in a range of about 10° C. to about 160° C., and preferably about 20° C. to about 120° C. The reaction time is about 1 to about 100 hours, and preferably about 2 to about 40 hours. The reaction is preferably carried out under an inert gas atmosphere (for example, nitrogen, argon, etc.).

(2) When $R^{2a}$ as represented in Compound (I-1) is, for example, a secondary amine residue, Compound (I-1) can be reacted with an alkyl halide or an aralkyl halide to prepare a tertiarized Compound (I'). Herein, examples of the halogen atom include chlorine, bromine, iodine, etc., and the alkyl halide or aralkyl halide is typically used in an amount of about 1 to 2 moles with respect to 1 mole of Compound (I-1). The reaction can be facilitated, if necessary, by addition of about an equimolar amount to about three-fold moles of a base such as triethylamine, diisopropylethylamine, pyridine, lithium hydride, sodium hydride, sodium methoxide, sodium ethoxide, sodium carbonate, potassium carbonate, sodium hydrogen carbonate or the like, and by further adding sodium iodide, potassium iodide, or the like.

This reaction of tertiary amination can be carried out in an inert solvent such as methanol, ethanol, propanol, isopropanol, n-butanol, tetrahydrofuran, diethyl ether, dimethoxyethane, 1,4-dioxane, toluene, benzene, xylene, dichloromethane, chloroform, 1,2-dichloroethane, dimethylformamide (DMF), dimethylsulfoxide (DMSO), pyridine, etc., or a mixture of the solvents above. The reaction is carried out at a temperature ranging from about 0° C. to about 180° C. for about 1 to about 40 hours. Also, the reaction is preferably carried out under an inert gas atmosphere (for example, nitrogen, argon, etc.).

(3) When $R^{2a}$ as represented in Compound (I-1) is, for example, a secondary amine residue, Compound (I-1) can be reacted with an aldehyde compound in the presence of a reductive amino reagent such as sodium triacetoxyborohydride, sodium cyanoborohydride, sodium borohydride or the like to prepare a tertiarized Compound (I'). The reaction conditions for this reductive amination reaction are preferably changed depending on the reagent used. For example, when sodium triacetoxyborohydride is used, the reaction can be conducted in an inert solvent, for example, dichloromethane, chloroform, 1,2-dichloroethane, tetrahydrofuran (THF), diethyl ether, dioxane, acetonitrile, dimethylformamide (DMF), etc., or a mixture of the solvents above. The reagent is used in an amount of about 1 to 2 molar equivalents with respect to 1 mole of Compound (I-1). The reaction is usually carried out at a temperature ranging from about 0° C. to about 80° C. for about 1 to about 40 hours. The reaction is preferably carried out under an inert gas atmosphere (for example, nitrogen, argon, etc.).

(4) When $R^{2a'}$ as represented in Compound (I-1) is, for example, a sulfide residue or a tertiary amine residue, or when $Z^2$ is, for example, a sulfide residue, Compound (I-1) can be reacted with an oxidizing agent, for example, m-chloroperbenzoic acid, perbenzoic acid, p-nitroperbenzoic acid, magnesium monoperoxyphthalate, peracetic acid, hydrogen peroxide, sodium periodate, potassium periodate, etc., to prepare Compound (I') having a sulfinyl group, a sulfonyl group or an amine oxide group. The reaction conditions for this oxidation reaction are preferably changed depending on the oxidizing agent used. For example, when m-chloroperbenzoic acid is used, the reaction can be carried out in an inert solvent, for example, dichloromethane, chloroform, 1,2-dichloroethane, diethyl ether, tetrahydrofuran, acetone, ethyl acetate, etc., or a mixture of the solvents above. The oxidizing agent is used in an amount of about 1 to 3 molar equivalents with respect to 1 mole of Compound (I-1). The reaction is usually carried out at a temperature ranging from about −78° C. to about 80° C. (preferably from −50 to 25° C.), for about 1 to about 40 hours.

When $Z^2$ as represented in Compound (I-1) is, for example, a sulfide residue, Compound (I') having an optically active sulfinyl group can be prepared according to the methods known per se, for example, the method described in Ojima, I., Ed., Catalytic Asymmetric Synthesis, 2000, Wiley-VCH (New York), or a similar method thereto.

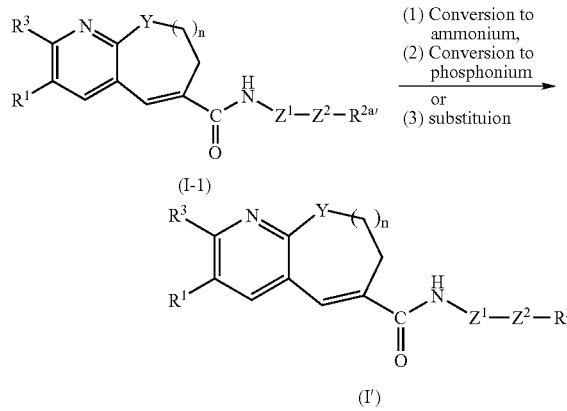

[Process C]

V in Compound (IV) represents a halogen atom (chlorine, bromine, iodine, etc.), or a sulfonyloxy group (a methanesulfonyloxy group, a trifluoromethanesulfonyloxy group, a benzenesulfonyloxy group, a toluenesulfonyloxy group, etc.), and the other symbols have the same meanings as defined above.

(1) Compound (IV) can be reacted with a tertiary amine to prepare quaternized Compound (I'). This reaction can be carried out in an inert solvent, for example, toluene, benzene, xylene, dichloromethane, chloroform, 1,2-dichloroethane, dimethylformamide (DMF), dimethylacetamide, etc., or a mixture of the solvents above. The tertiary amine is used in an amount of about 1 to 3 moles with respect to 1 mole of Compound (IV). This reaction is carried out at a temperature in a range of about 10° C. to about 120° C. for about 1 to about 40 hours. The reaction is preferably carried out under an inert gas (for example, nitrogen, argon, etc.) atmosphere.

(2) Compound (IV) can be reacted with a tertiary phosphine to prepare quaternized Compound (I'). This reaction can be carried out in an inert solvent, for example, toluene, benzene, xylene, dichloromethane, chloroform, 1,2-dichloroethane, acetonitrile, dimethylformamide (DMF), etc., or a mixture of the solvents above. The tertiary phosphine is used in an amount of about 1 to 2 moles with respect to 1 mole of Compound (IV). This reaction is carried out at a temperature in a range of about 20° C. to about 150° C. for about 1 to about 50 hours. This reaction is preferably carried out under an inert gas (for example, nitrogen, argon, etc.) atmosphere.

(3) Compound (IV) can be reacted with a primary or secondary amine compound or a thiol compound to prepare Compound (I') having a secondary or tertiary amino group or a thio group. The primary or secondary amine compound or the thiol compound is usually used in an amount of about 1 to 3 moles with respect to 1 mole of Compound (IV). This reaction can be facilitated, if necessary, by adding about an equivalent to three-fold moles of a base such as triethylamine, diisopropylethylamine, pyridine, lithium hydride, sodium hydride, sodium methoxide, sodium ethoxide, sodium carbonate, potassium carbonate, sodium hydrogen carbonate and the like, and by further adding sodium iodide, potassium iodide and the like. This substitution reaction can be carried out in an inert solvent, for example, methanol, ethanol, propanol, isopropanol, n-butanol, tetrahydrofuran, diethyl ether, dimethoxyethane, 1,4-dioxane, toluene, benzene, xylene, dichloromethane, chloroform, 1,2-dichloroethane, dimethylformamide (DMF), dimethylsulfoxide (DMSO), pyridine, etc., or a mixture of the solvents above. The reaction is carried out at a temperature in a range of about −10° C. to about 180° C. for about 1 to about 40 hours. This reaction is preferably carried out under an inert gas (for example, nitrogen, argon, etc.) atmosphere.

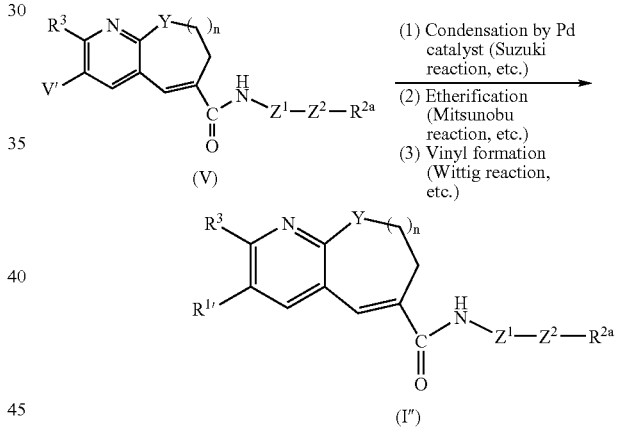

[Process D]

(1) Compound (V) [wherein V' represents a halogen atom (bromine, iodine, etc.) or a sulfonyloxy group (a trifluoromethanesulfonyloxy group, etc.), and the other symbols have the same meanings as defined above] can be subjected to, for example, the Suzuki reaction [a cross-coupling reaction of an arylboric acid and, for example, aryl halide or aryloxy trifluoromethanesulfonate, catalyzed by a palladium catalyst; A. Suzuki et al., Synth. Commun., 11, 513 (1981)], to prepare Compound (I″) in which $R^1$ is a 5- or 6-membered aromatic group. The arylboric acid can be used in an amount of about an equivalent to 1.5-fold moles with respect to 1 mole of Compound (V) to prepare Compound (I″).

Further, Compound (V) can be subjected to, for example, a cross-coupling reaction with an arylacetylene compound in the presence of a palladium catalyst [dichlorobis(triphenylphosphine)palladium, etc.][K. S. Y. Lau et al., J. Org. Chem., 46, 2280 (1981); J. W. Tilley, S. Zawoisky et al., J. Org. Chem., 53, 386 (1988)] to prepare Compound (I″) having an acetylene bohd, in which $X^1$ represents −C≡C—. The arylacetylene compound can be used typically in an amount of about an equivalent to two-fold moles with respect to 1 mole of Compound (V) to prepare Compound (I").

(2) Compound (V) [wherein V' represents a hydroxy group and the other symbols have the same meanings as defined above] can be subjected to, for example, the Mitsunobu reaction [an etherification reaction using, for example, triphenylphosphine and diethyl azodicarboxylate as the condensing agents; O. Mitsunobu et al., Synthesis, 1 (1981)] to prepare Compound (I") having an ether bond. The corresponding alcohol compound or phenol compound can be used in an amount of about an equivalent to three-fold moles with respect to 1 mole of Compound (V) to prepare Compound (I").

Compound (I") having an ether bond can also be prepared by an etherification reaction of Compound (V) with a reactive compound such as a halide (chloride, bromide, iodide, etc.) compound, a tosylate compound, a mesylate compound, etc. The reactive compound is used typically in an amount of about an equivalent to two-fold moles with respect to 1 mole of Compound (V). This reaction can be facilitated, if necessary, by adding about an equivalent to three-fold moles of a base such as triethylamine, diisopropylethylamine, pyridine, lithium hydride, sodium hydride, sodium hydroxide, potassium hydroxide, sodium methoxide, sodium ethoxide, sodium carbonate, potassium carbonate, sodium hydrogen carbonate, etc., and by further adding sodium iodide, potassium iodide, etc. The reaction can be carried out in an inert solvent such as tetrahydrofuran, diethyl ether, dimethoxyethane, 1,4-dioxane, toluene, benzene, xylene, dichloromethane, chloroform, 1,2-dichloroethane, dimethylformamide (DMF), dimethylsulfoxide (DMSO), pyridine, etc., or a mixture of the solvents above. The reaction is carried out at a temperature in a range of about −10° C. to 180° C. for about 1 to about 40 hours. The reaction is preferably carried out under an inert gas (for example, nitrogen, argon, etc.) atmosphere.

(3) Compound (V), wherein V' represents a carbonyl group which may be substituted, a phosphonium salt or a phosphonic acid ester residue, and the other symbols have the same meanings as defined above, can be subjected to, for example, the Wittig reaction [A. Maercker, Org. React., 14, 270 (1965)] or the Wittig-Horner-Emmons reaction [J. Boutagy and R. Thomas, Chem. Rev., 74, 87 (1974)] to prepare Compound (I") having a vinyl bond. The corresponding carbonyl compound, a phosphonium salt or a phosphonic acid ester compound is used in an amount of about an equivalent to 1.5-fold moles with respect to 1 mole of Compound (V).

[Process E]

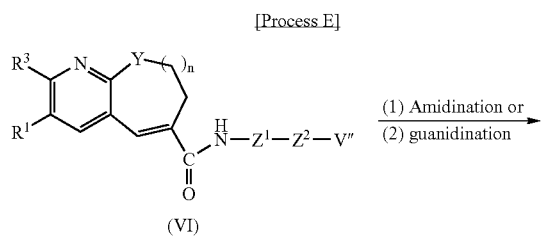

(VI)

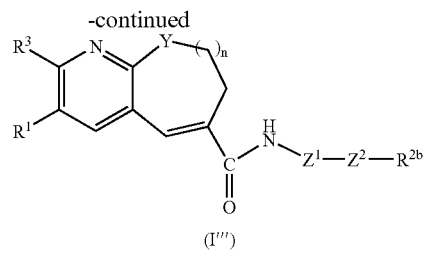

(I''')

(1) First, Compound (VI), wherein V'' represents a cyano group, and the other symbols have the same meanings as defined above, is reacted with a lower alcohol such as methanol, ethanol, propanol, etc. in the presence of an acid such as hydrochloric acid, etc. to give an imidate compound. This reaction is typically carried out using an excess of the alcohol at a temperature in a range of about −10° C. to 50° C. for about 1 hour to about 40 hours. The reaction can be carried out in an inert solvent such as diethyl ether, 1,4-dioxane, toluene, benzene, xylene, dichloromethane, chloroform, 1,2-dichloroethane, etc., or a mixture of the solvents above.

Subsequently, the resulting imidate compound can be subjected to a substitution reaction with a primary or secondary amine compound to prepare an amidine compound [I''']. The primary or secondary amine compound is used typically in an amount of about 1 to 5 moles with respect to 1 mole of the imidate compound. The reaction can be facilitated, if necessary, by adding about an equimolar amount to three-fold moles of a demineralizing agent such as triethylamine, pyridine, sodium hydroxide, potassium hydroxide, sodium methoxide, sodium ethoxide, sodium carbonate, potassium carbonate, etc. This substitution reaction can be carried out in an inert solvent, for example, methanol, ethanol, propanol, isopropanol, n-butanol, tetrahydrofuran, diethyl ether, dimethoxyethane, 1,4-dioxane, toluene, benzene, xylene, dichloromethane, chloroform, 1,2-dichloroethane, dimethylformamide (DMF), dimethylsulfoxide (DMSO), pyridine, etc., or a mixture of the solvents above. The reaction is carried out at a temperature in a range of about 0° C. to 150° C. for about 1 to about 50 hours. The reaction is also preferably carried out under an inert gas (for example, nitrogen, argon, etc.) atmosphere.

(2) Compound (VI), wherein V'' is an amino group, and the other symbols have the same meanings as defined above, can be subjected to a substitution reaction with an S-alkyl (for example, methyl, ethyl, etc.)-isothiourea compound to prepare guanidine Compound (I'''). The S-alkyl-isothiourea compound is typically used in an amount of about an equivalent to two-fold moles with respect to 1 mole of Compound (VI). This reaction can be facilitated, if necessary, by adding about an equimolar amount to three-fold moles of a demineralizing agent such as triethylamine, pyridine, sodium hydroxide, potassium hydroxide, sodium methoxide, sodium ethoxide, sodium carbonate, potassium carbonate, etc. This substitution reaction can be carried out in an inert solvent, for example, methanol, ethanol, propanol, isopropanol, n-butanol, tetrahydrofuran, diethyl ether, dimethoxyethane, 1,4-dioxane, toluene, benzene, xylene, dichloromethane, chloroform, 1,2-dichloroethane, dimethylformamide (DMF), dimethylsulfoxide (DMSO), pyridine, etc., or a mixture of the solvents above. The reaction is carried out at a temperature in a range of about 0° C. to 150° C. for about 1 to about 50 hours. This reaction is preferably carried out under an inert gas (for example, nitrogen, argon, etc.) atmosphere.

The thus-obtained Compound (I) can be isolated and purified by known separation and purification means, for example, concentration, vacuum concentration, solvent extraction, crystallization, recrystallization, redissolution, chromatography and the like.

Compound (II-1) which is used as the starting material can be prepared by any known methods (for example, the methods described in JP-A No. 8-73476; and JP-A No. 2001-058988, etc.) or a modification thereof, for example, the method of the reaction scheme I, the methods in Reference Examples described below and modifications thereof.

Compound (VII) can be subjected to the Dieckmann (type) condensation reaction (J. P. Schaefer and J. J. Bloomfield, Org. Reactions, 15, 1 (1967)) to prepare Compound (VIII) or Compound (IX). Compound (VIII) can be subjected to catalytic hydrogenation or a reductive reaction with sodium borohydride, etc. to prepare Compound (IX). Compound (IX) can be subjected to dehydration by a conventional method to prepare an unsaturated carboxylic ester (X). Compound (X) can be subjected to, for example, the Suzuki reaction and subsequently subjected to ester hydrolysis to prepare unsaturated carboxylic acid Compound (II').

Also, Compound (III-1) can be prepared by any known methods (for example, the methods described in JP-A No. 8-73476, etc.) or similar methods thereto, for example, the method of the reaction scheme III, the methods in Reference Examples described below and modifications thereof.

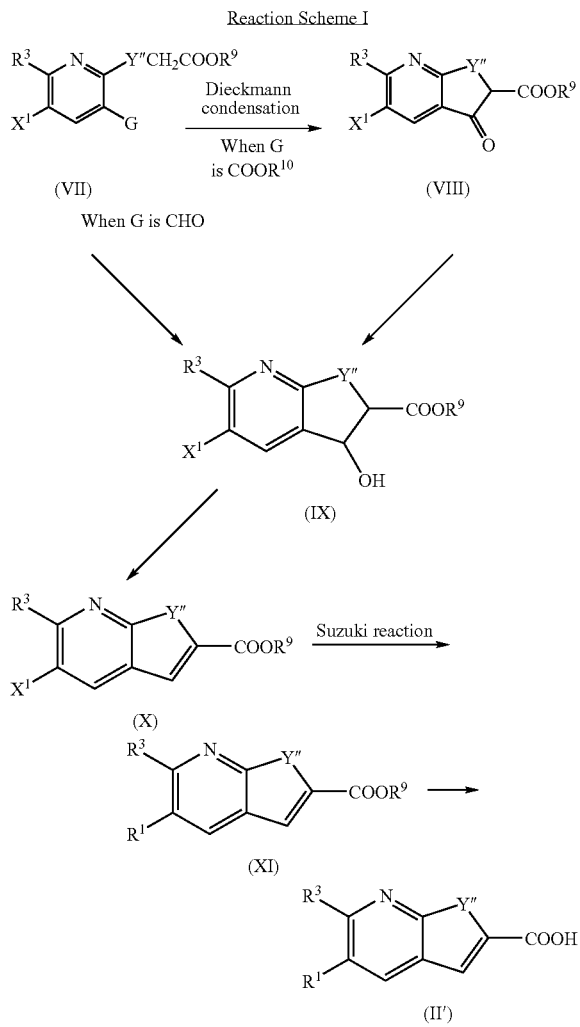

Reaction Scheme I

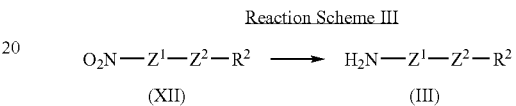

Reaction Scheme III wherein each symbol has the same meaning as defined above.

Reduction of Compound (XII) can be carried out by the methods known per se in the art. For example, reduction by metal, metal hydride or a metal hydrogen complex compound, reduction by diborane and substituted borane, catalytic hydrogenation, or the like is used. That is, this reaction is carried out by treating Compound (XII) with a reducing agent. Examples of the reducing agent include metals such as reduced iron, zinc powder, etc.; metal hydrogen complex compounds such as alkali metal borohydrides (for example, sodium borohydride, lithium borohydride, etc.), aluminum lithium hydride, etc.; metal hydrides such as sodium hydride, etc.; organic tin compounds (triphenyltin hydride, etc.); metals and metal salts such as nickel compounds, zinc compounds, etc.; catalytic reducing agents using hydrogen and transition metal catalysts such as palladium, platinum, rhodium, etc.; diborane; and the like. The catalytic reduction using hydrogen and a transition metal such as palladium, platinum, rhodium, etc., and the reduction by a metal such as reduced iron are advantageously employed. This reaction is carried out in an organic solvent which does not interfere with the reaction. The solvent is appropriately selected for use from, for example, benzene, toluene, xylene, chloroform, carbon tetrachloride, dichloromethane, 1,2-dichloroethane, 1,1,2,2-tetrachloroethane, diethyl ether, tetrahydrofuran, dioxane, methanol, ethanol, propanol, isopropanol, 2-methoxyethanol, N,N-dimethylformamide, acetic acid or a mixture of the solvents above, depending on the kind of the reducing agent. The reaction temperature is about −20° C. to about 150° C., and particularly preferably about 0° C. to about 100° C., and the reaction time is about 1 to about 24 hours.

The thus-obtained Compound (III-1) can be isolated and purified by known separation and purification means such as concentration, vacuum concentration, solvent extraction, crystallization, recrystallization, redissolution, chromatography and the like.

The compound represented by the formula (I) of the present invention or a salt thereof including the above-mentioned Compound (Ia), Compound (I-1), Compound (I'), Compound (I") and Compound (I'") (hereinafter, in the case where it is briefly referred to as "the compound represented wherein $R^9$ and $R^{10}$ each represents a $C_{1-4}$ alkyl group, $X^1$ represents a leaving group [a halogen atom (chlorine, bromine, iodine, etc.), methanesulfonyloxy, trifluoromethanesulfonyl, benzenesulfonyloxy, toluenesulfonyloxy, etc.], Y" represents a divalent group having no unsaturated bond, in which a Y"-containing ring forms a 6- to 10-membered ring, and the other symbols have the same meanings as defined above.

by the formula (I)", it is intended to include the compound represented by the formula (I) and a salt thereof) can be administered orally or parenterally alone or as a pharmaceutical composition comprising the compound mixed with a pharmaceutically acceptable carrier in the form of a solid preparation such as a tablet, a capsule, a granule, powders, etc., or a liquid preparation such as a syrup, an injectable solution, etc.

Examples of the dosage form for parenteral administration include an injectable solution, an infusion, a suppository, a vaginal suppository, etc., and in particular, the vaginal suppository is useful for prevention of HIV infection.

As the pharmaceutically acceptable carrier, a variety of organic or inorganic carriers that are commonly used as materials for pharmaceutical preparation may be used, and they are added as an excipient, a lubricant, a binder or a disintegrant in solid preparations, and as a solvent, a solubilizing agent, a suspending agent, an isotonic agent, a buffer, a soothing agent or the like in liquid preparations. Other additives for preparation such as an antiseptic agent, an antioxidant, a colorant, a sweetener or the like may also be used, if necessary. Preferred examples of the excipient include lactose, sucrose, D-mannitol, starch, crystalline cellulose, light anhydrous silica and the like. Preferred examples of the lubricant include magnesium stearate, calcium stearate, talc, colloidal silica and the like. Preferred examples of the binder include crystalline cellulose, sucrose, D-mannitol, dextrin, hydroxypropylcellulose, hydroxypropylmethylcellulose, polyvinylpyrrolidone and the like. Preferred examples of the disintegrant include starch, carboxymethylcellulose, calcium carboxymethylcellulose, sodium croscarmellose, sodium carboxymethylstarch and the like. Preferred examples of the solvent include water for injection, alcohol, propylene glycol, macrogol, sesame oil, corn oil and the like. Preferred examples of the solubilizing agent include polyethylene glycol, propylene glycol, D-mannitol, benzyl benzoate, ethanol, trisaminomethane, cholesterol, triethanolamine, sodium carbonate, sodium citrate and the like. Preferred examples of the suspending agent include surfactants such as stearyltriethanolamine, sodium laurylsulfate, laurylaminopropionic acid, lecithin, benzalkonium chloride, benzethonium chloride, glycerin monostearate, etc.; hydrophilic polymers such as polyvinyl alcohol, polyvinyl pyrrolidone, sodium carboxymethylcellulose, methylcellulose, hydroxymethylcellulose, hydroxyethylcellulose, hydroxypropylcellulose, etc.; and the like. Preferred examples of the isotonic agent include sodium chloride, glycerin, D-mannitol and the like. Preferred examples of the buffer include buffer solutions of salts such as phosphate, acetate, carbonate, citrate and the like. Preferred examples of the soothing agent include benzyl alcohol and the like. Preferred examples of the antiseptic agent include para-oxybenzoic acid esters, chlorobutanol, benzyl alcohol, phenethyl alcohol, dehydroacetic acid, sorbic acid and the like. Peferred examples of the antioxidant include sulfite salts, ascorbic acid and the like.

The compound represented by the formula (I) of the present invention or a salt thereof has excellent CCR antagonistic action, in particular, CCR5 and/or CCR2 antagonistic action, and especially, strong CCR5 antagonistic action, and therefore it can be used in prevention and treatment of human HIV infection, for example, AIDS, and also in prevention and treatment of other various diseases. Further, the compound represented by the formula (I) of the present invention or a salt thereof has low toxicity and can be used safely.

For example, the pharmaceutical composition containing the compound represented by the formula (I) of the present invention or a salt thereof can be used as a CCR5 antagonist, for example, a prophylactic and/or therapeutic agent for AIDS and a suppressive agent for disease progression of AIDS. Furthermore, the pharmaceutical composition containing the compound represented by the formula (I) of the present invention or a salt thereof may be used as a prophylactic and/or therapeutic agent for a variety of diseases, such as a prophylactic and/or therapeutic agent for graft versus host disease (GVHD) and/or rejection reaction, a prophylactic and/or therapeutic agent for chronic rheumatoid arthritis, autoimmune diseases, allergic diseases, ischemic brain cell disorder, cardiac infarction, chronic nephritis or arteriosclerosis, and the like.

Examples of the diseases for which the prophylactic and/or therapeutic agent of the present invention is used, include graft rejection (post-transplantational rejection, post-transplantational polycythemia, hypertension, organ disorder, vascular hypertrophy, graft versus host disease, etc.); arthritic osteopathic diseases such as periostitis/meningitis, etc. (chronic rheumatoid arthritis, osteoarthritis deformans, rheumatoid myelitis, osteoporosis, abnormal growth of cell, fracture, refracture, osteomalacia, osseous Behcet's disease, ankylosing myelitis, articular tissue destruction by gonarthritis deformans and diseases similar thereto, etc.); autoimmune diseases (collagen disease, SLE (systemic lupus erythematosus), pachyderms, polyarteritis, myasthenia gravis, multiple sclerosis, etc.); allergic diseases (allergic nasal catarrh, conjunctivitis, gastrointestinal allergy, pollinosis, anaphylaxis, atopic dermatitis, bronchial asthma, etc.); inflammatory enteropathic diseases (ulcerative colitis, Crohn's disease, gastritis, gastric ulcer, gastric cancer, post-gastrotomic disorder, dyspepsia, esophageal ulcer, pancreatitis, polyp of the colon, cholelithiasis, hemorrhoids, peptic ulcer, situational ileitis, etc.); inflammatory diseases (retinopathy, post-operative and post-traumatic inflammation, remission of puffiness, pharyngitis, cystitis, meningitis, inflammatory ophthalmic diseases, etc.); respiratory diseases (cold syndrome, pneumonia, asthma, pulmonary hypertension, pulmonary thrombi/pulmonary obliteration, pulmonary sarcoidosis, pulmonary tuberculosis, interstitial pneumonia, silicosis, adult tachypnea syndrome, chronic, obliterative pulmonary diseases, etc.); infectious diseases (viral infection caused by cytomegalovirus, influenza virus, herpes virus or the like, rickettsia infection, bacterial infection, sexually transmitted diseases, carinii pneumonia, helicobacter pylori infection, systemic fungal infection, tuberculosis, invasive staphylococcal infection, acute viral encephalitis, acute bacterial meningitis, AIDS encephalopathy, septicemia, sepsis, sepsis gravis, septic shock, endotoxin shock, toxic shock syndromes, etc.); cancers and accompanying cachexia, cancer metastases (bladder cancer, breast cancer, cervical cancer, ovarian cancer, chronic lymphoblastic leukemia, chronic myeloid leukemia, colon cancer, rectal cancer, colic cancer, multiple myeloma, malignant myeloma, prostatic cancer, lung cancer, gastric cancer, Hodgkin's disease, malignant melanoma, malignant lymphoma, etc.); non-Hodgkin's lymphoma; non-small cell lung cancer; malignant melanoma, neurodegenerative diseases (Alzheimer's disease, Parkinson's disease, amyotrophic lateral sclerosis (ALS), Huntington's chorea, diabetic neural disorder, Creutzfeldt-Jakob disease, etc.); mental diseases (depression, epilepsia, alcoholism etc.); schizophrenia; venous dysfunction; central nerve disorder (disorder of intracerebral bleeding, brain infarction, etc. and aftereffect/complication therefrom, cephalic trauma, spinal damage, brain edema, sensory malfunction, sensory dysfunction, autonomic nervous malfunction, autonomic nervous dysfunction, and the like); central damage (cephalic trauma, spinal damage, whiplash injury, etc.); vascular dementia (multiinfarct dementia, Binswanger's disease, etc.); cerebrovascular accident (asymptomatic cerebrovascular accident, transient cerebral ischemic attack, stroke, cerebrovascular dementia, hypertensive encephalopathy, etc.); recurrence and aftereffect of cerebrovascular accident (neural symptom, mental symptom, subjective symptom, operational disorder in daily life, etc.); cerebral vascular dementia; post-cerebrovascular obliteration central hypofunction; disorder or abnormality of cerebral circulation and autoregulation of renal circulation; blood brain barrier disorder; anxiety symptom; acute coronary artery syndromes including unstable angina, etc.; anxious mental state; amnesia; prosopalgia; otolaryngological disease (Meniere's syndrome, tinnitus, gustation disorder, dizziness, dysequilibrium, dysphagia, etc.); migraine; chronic pain; dermatoses (keloid, angioma, psoriasis, etc.); arteriosclerosis obliterans; thromboangiitis obliterans; peripheral obstruction; postischemic reperfusion injury; Raynaud's disease; Buerger's disease; myocarditis; cardiac ischemia; cardiac infarction; progress of cardiac failure after cardiac infarction; cardiomyopathy; cardiac hypertrophy; acute cardiac failure and chronic (including estatic) cardiac failure; angina pectoris; arrhythmia; tachycardia; circadian rhythm disorder of blood pressure; abnormality in characteristic of blood haemocyte components (enhancement in platelet aggregation, abnormality of erythrocyte deformability, enhancement in leucocyte adhesiveness, increase in blood viscosity, polycythemia, vascular peliosis, autoimmune hemolytic anemia, disseminated intravascular coagulation syndrome, multiple myelopathy, etc.); arteriosclerosis including atherosclerosis (aneurysm, coronary arteriosclerosis, cerebro arteriosclerosis, peripheral arteriosclerosis, etc.); vascular reocclusion and restenosis after bypass operation; vascular hyperplasia or occlusion and organ malfunction after intervention (transdermal coronary arterioplasty, stent detention, coronary autoscope, vascular ultrasound therapy, coronary injection thrombolytic therapy, etc.); production and enhancement of vasoactive materials and thrombi inducing materials (endothelin, thromboxan A2, etc.); arterialization (including abnormal vasculogenesis in abnormal capillary vasoganglion formation in the atherosclerotic outer membrane); thrombosis; fat storage disease acceleration; ophthalmic diseases (glaucoma, ocular hypertension disease, etc.); hypertension; hypertensive tinnitus; dialysis hypotension; endothelial cell and organ disorders; endocrinopathy (Addison's disease, Cushing's syndrome, melanocytoma, primary aldosteronism, etc.); nephritis; renal diseases (nephritis, glomerulonephritis, glomerulosclerosis, renal failure, thrombotic microangiopathy, dialysis complications, organ disorders including nephropathy by radiation, diabetic nephropathy, etc.); diabetic diseases (insulin-dependent diabetes, diabetic complications, diabetic retinopathy, diabetic microangiopathy, diabetic neuropathy, etc.); glucose tolerance abnormality; hepatic diseases (hepatitis (including chronic hepatitis), hepatic cirrhosis, etc.); interstitial hepatic diseases; chronic pancreatitis; portal pressure enhancement; obesity; male sterility; gynecologic diseases (climacteric disorder, gestational toxicosis, endometriosis, hysteromyoma, ovarian disease, mammary disease, etc.); edema; chronic fatigue syndromes; prostatomegaly; Behcet's disease; Hodgkin's disease; lacunar infarction; consciousness disorder; psoriasis; diseases due to environmental or occupational factors (disorder caused by radiation, disorders caused by ultraviolet ray/infrared ray/laser ray, altitude sickness, etc.); intermittent claudication; and the like.

The pharmaceutical composition containing the compound represented by the formula (I) or a salt thereof may vary depending on the kind of disease to be treated and may be used in combination with other drugs. Examples of the other drugs include HDL-increasing drugs [a squalene synthase inhibitor, a CETP inhibitor, a LPL activator, etc.]; a prophylactic and/or therapeutic agent for HIV infection [nucleic acid reverse transcriptase inhibitors such as zidovudine, didanosine, zalcitabine, lamivudine, stavudine, abacavir, adefovir, adefovir dipivoxil, fozivudine tidoxil, etc., non-nucleic acid reverse transcriptase inhibitors such as nevirapine, delavirdine, efavirenz, loviride, immunocal, oltipraz, etc., protease inhibitors such as saquinavir, ritonavir, indinavir, nelfinavir, amprenavir, palinavir, lasinavir, lopinavir, etc.]; HMG-CoA reductase inhibitors [cerivastatin, atorvastatin, pravastatin, simvastatin, itavastatin, lovastatin, fluvastatin, (+)-3R,5S-7-[4-(4-fluorophenyl)-6-isopropyl-2-(N-methyl-N-methanesulfonylamino]pyrimidin-5-yl]-3, 5-dihyclroxy-6(E)-heptenoic acid, etc.]; atopic dermatitis drugs [sodium cromoglycate, etc.]; allergic nasal catarrh drugs [sodium cromoglycate, chlorpheniramine maleate, alimemazine tartrate, clemastine flimarate, homochlorcyclizine hydrochloride, terfenadine, mequitazine, etc.]; imipenem.cilastatin sodium; endotoxin antagonists or antibodies; oxidosqualene-lanosterol cyclase [e.g., decalin derivatives, azadecalin derivatives and indane derivatives]; calcium antagonists (diltiazem, etc.); glycerol; cholinesterase inhibitors (e.g., Aricept (donepezil), etc.); compounds suppressing cholesterol uptake [e.g., sitosterol, neomycin, etc.]; compounds inhibiting cholesterol biosyntheses [e.g., HMG-CoA reductase inhibitors such as lovastatin, simvastatin, pravastatin, etc.];

cyclooxygenase inhibitors [Cox-I, Cox-II inhibitors such as celecoxib, rofecoxib, salicylic acid derivatives such as aspirin and the like, diclofenac, indometacin, loxoprofen, etc.]; signal transduction inhibitors, squalene epoxidase inhibitors [e.g., NB-598 and the analogous compounds, etc.]; steroidal drugs [dexamethasone, hexestrol, methimazole, betamethasone, triamcinolone, triamcinolone acetonide, fluocinonide, fluocinolone acetonide, prednisolone, methylprednisolone, cortisone acetate, hydrocortisone, fluorometholone, beclomethasone propionate, estriol, etc.]; diacerin; nicotinic acid and derivatives and analogues thereof [e.g., acipimox and probucol]; nicergoline, nephrotic syndrome drugs: prednisolone (Predonine), prednisolone sodium succinate (Predonine), methyiprednisolone sodium succinate (Solumedrol), betamethasone (Rinderon), dipyridamole (Persantme), dilazep hydrochloride (Comelian), ticlopidine, clopidogrel, antiplatelet drugs and anticoagulants such as FXa inhibitors, etc.; barbital-based anticonvulsants or anaesthetic drugs (phenobarbital, mephobarbital, metharbital, etc.); Parkinson's disease drugs (e.g., L-DOPA, etc.); histamine receptor blockers (cimetidme, famotidine, etc.); hydantoin-based anticonvulsant drugs (phenytoin, mephenytoin, ethotoin, etc.); piroxicam, fibrates [e.g., clofibrate, benzafibrate, gemfibrozil, etc.]; prostaglandins; megestrol acetate; gastric and intraduodenal ulcer drugs: antacids [e.g., histamine H2 antagonists (cimetidine, etc.), proton pump inhibitors (lansoprazole, etc.), and the like]; inflammatory mediator inhibitors; coronary vasodilators: nifedipine, diltiazem, nicorandil, nitrite drugs, etc.; infectious disease drugs: [e.g., antibiotic formulations (cefotiam hydrochloride, cefozopran hydrochloride, ampicillin, etc.), chemotherapeutic agents (sulfa drugs, synthetic antibacterial agents, antiviral agents, etc.), biologic formulations (vaccines, blood preparations including inimunoglobulins) etc.] etc.; hepatic disease drugs: glycyrrhizin formulations [e.g., Stronger Minophagen, etc.]; liver hydrolysate; SH compounds [e.g., glutathione, etc.]; special amino acid formulations [e.g., aminoleban, etc.]; phospholipids [e.g., polyene-phosphatidylcholine, etc.]; vitamins [e.g., vitamin $B_1$, $B_2$, $B_6$, $B_{12}$, C, etc.]; adrenocortical hormones [e.g., dexamethasone, betamethasone, etc.]; interferons [e.g., interferon α, β, etc.]; hepatic encephalopathy drugs [e.g., lactulose, etc.]; hemostatic agents used in cases of rupture of esophageal and gastric varices [e.g., vasopressin, somatostatin, etc.]etc.; arthritis drugs; muscle relaxants [pridinol, tubocurarine, pancuronium, tolperisone hydrochloride, chlorphenesin carbamate, baclofen, chlormezanone, mephenesin, chlorzoxazone, eperisone, tizanidine, etc.]; vasodilators [oxyfedrine, diltiazem, tolazolme, hexobendine, bamethan, clonidine, methyldopa, guanabenz, etc.]; vasoconstrictors [dopamine, dobutamine, denopamine, etc.]; platelet coagulation inhibitors (ozagrel, etc.); thrombogenesis prophylactic and/or therapeutic drugs: anticoagulant drugs [e.g., heparm sodium, heparin calcium, warfarin calcium (Warfarin), Xa inhibitors]; thrombolytic drugs [e.g., tPA, urokinase]; antiplatelet drugs [e.g., aspirin, sulfinpyrazone (Anturan), dipyridamole (Persantine), ticlopidine (Panaldine), cilostazol (Pletal), GPIIb/IIIa antagonists (ReoPro)]; antidepressants [imipramine, clomipramine, noxiptiline, feneizin, amitriptyline hydrochloride, nortriptyline hydrochloride, amoxapine, mianserm hydrochloride, maprotiline hydrochloride, sulpiride, fluvoxamine maleate, trazodone hydrochloride, etc.]; antiepileptic drugs [gabapentin, phenytoin, ethosuximide, acetazolamide, chlordiazepoxide, trimethadione, carbamazepine, phenobarbital, primidone, sultiame, sodium valproate, clonazepam, diazepam, nitrazepam, etc.]; antiallergic drugs [diphenhydramine, chlorpheniramine, tripelennamine, methdilazine. clemizole, diphenylpyraline, methoxyphenamine, sodium cromoglycate, tranilast, repirinast, amlexanox, ibudilast, ketotifen, terfenadine, mequitazine, azlastine, epinastine, ozagrel hydrochloride, pranlukast hydrate, seratrodast, fexofenadine, ebastine, bucillamine, oxatomide, Stronger Neo-Minophagen C, tranexamic acid, ketotifen fumarate, etc.]; anticholinergic drugs (e.g., ipratropium bromide, flutropium bromide, oxitropium bromide, etc.); anti-Parkinson drugs (dopamine, levodopa, etc.); anti-rheumatic drugs; anti-inflammatory drugs (e.g., aspirin, acetaminophen, diclofenac sodium, ibuprofen, indometacin, loxoprofen sodium, dexamethasone, etc.); anticoagulant and antiplatelet drugs [sodium citrate, activated protein C, tissue factor pathway inhibitors, antithrombin III, dalteparin sodium, argatroban, gabexate, ozagrel sodium, ethyl icosapentate, beraprost sodium, alprostadil, pentoxifylline, tisokinase, streptokinase, heparin. etc.]; anticoagulant therapeutic drugs [dipyridamole (Persantine), dilazep hydrochloride (Comelian), ticlopidme, clopidogrel, Xa inhibitors]; antibacterial drugs [(1) sulfa drugs [sulfamethizole, sulfisoxazole, sulfamonomethoxine, sulfamethizole, salazosulfapyridine, sulfadiazine silver, etc.], (2)quinolone-based antibacterial drugs [nalidixic acid, pipemidic acid trihydrate, enoxacin, norfioxacin, ofloxacin, tosufloxacin tosilate, ciprofloxacin hydrochloride, lomefloxacin hydrochloride, sparfloxacin, fleroxacin, etc.], (3) antituberculous drugs [isoniazid, ethambutol (ethambutol hydrochloride), p-aminosalicylic acid (calcium p-aminosalicylate), pyrazinamide, ethionamide, prothionamide, rifampicin, streptomycin sulfate, kanamycin sulfate, cycloserine, etc.], (4) anti-acid fast bacterial drugs [diaphenylsulfone, rifamnicin, etc.], (5) antiviral drugs [idoxuridine, acyclovir, vidarabine, ganciclovir, etc.], (6) anti-HIV drugs [zidovudine, didanosine, zalcitabine, indinavir sulfate ethanolate, ritonavir, etc.], (7) spirocheticide, (8) antibiotics [tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotiam, cefuroxime, cefotiam, cefotiam hexetil, cefuroxime axetil, cefdinir, cefditoren pivoxil, ceftazidime, celbiramide, cefsulodin, cefmenoxime, cefpodoxime proxetil, cefpirome, cefozopran, cefepime, cefsulodin, cefmetazole, cefrninox, cefoxitin, cefbuperazone; latamoxef, flomoxef, cefazolin, cefotaxime, cefoperazone, ceftizoxime, moxalactam, thienamycin, sulfazecin, aztreonam or salts thereof, griseofulvin, lankacidins [J. Antibiotics, 38, 877-885 (1985)], etc.], cefixime, levofloxacin]; antithrombotic drugs (argatroban, etc.); antiprotozoal drugs [metronidazole, tinidazole, diethylcarbamazine citrate, quinine hydrochloride, quinine sulfate, etc.]; antitumor drugs [6-O—(N-chloroacetylcarbamoyl)fumagillol, bleomycm, methotrexate, actinomycm D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinbiastine sulfate, irinotecan hydrochloride, cyclophosphamide, meiphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuplm acetate, buserelin acetate, etc.]; antifungal drugs [(1) polyethylene-based antibiotics (e.g., amphotericm B, nystatm, trichomycin), (2) griseofulvin, pyrrolnitrin, etc., (3) cytosme metabolism antagonists (e.g., flucytosine), (4) imidazole derivatives (e.g., econazole, clotrimazole, miconazole nitrate, bifonazole and croconazole), (5) triazole derivatives (e.g., fluconazole, itoraconazole, azole compounds [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl-3-(2H,4H)-1,2,4-triazolone], (6) thiocarbamate derivatives [e.g., trinaphthol], (7) echinocandin-based derivatives (e.g., caspofungin, FK-463, V-echinocandm), etc.]; antipsychotic drugs [chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpme, clocapramine hydrochloride, sulpiride, zotepine, etc.]; antiulcer drugs [metoclopramide, histidine hydrochloride, lansoprazole, metoclopramide, pirenzepme, cimetidine, ranitidine, famotidine, urogastron, oxethazaine, proglumide, omeprazole, sucralfate, sulpiride, cetraxate, gefarnate, aldioxa, teprenone, prostaglandins, etc.]; anti-diabetic drugs [e.g., pioglitazone, nateglinide, voglibose, acarbose, etc.]; antiobesity drugs (mazindol, etc.); antirheumatic drugs, etc.; antianxiety drugs [diazepam, lorazepam, oxazepam, chlordiazepoxide, medazepam, oxazolam, cloxazolam, clotiazepam, bromazepam, etizolam, fludiazepam, hydroxyzine, etc.]; antiarrhythmic drugs: disopyramide, lidocaine, quinidine sulfate, flecainide acetate, mexiletine hydrochloride, amiodarone hydrochloride, and β blockers, Ca antagonists, etc.; antiasthmatic drugs [isoprenaline hydrochloride, salbutamol sulfate, procaterol hydrochloride, terbutaline sulfate, trimetoqunol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglycate, tranilast, repirinast, amlexanox, ibudilast, ketotifen, terfenadine, mequitazine, azelastine, epmastine, ozagrel hydrochloride, pranlukast hydrate, seratrodast, dexamethasone, prednisolone, hydrocortisone, beclomethasone propionate, fluticasone propionate, beclomethasone propionate, procaterol, etc.]; anti-hypothyroidism drugs [dried thyroid (Thyreoid), levothyroxine sodium (Thyradm S), liothyronine sodium (thyronine, tyronamine)]; nephrotic syndrome drugs [prednisolone (Predonine), prednisolone sodium succmate (Predonine), methylprednisolone sodium succinate (Solumedrol), betamethasone (Rinderon)]; antihypertensive drugs [(1) sympathetic nerve inhibitors [$\alpha 2$ stimulants (e.g., clonidine, guanabenz, guanfacine, methyldopa, etc.), ganglionic blockers (e.g., hexamethonium, trimethaphan, etc.), presynaptic blockers (e.g., ARSA-Oxylone, dimethylaminoreserpinate, rescinnamine, reserpine, syrosingopine, etc.), neuronal blockers (e.g., betanidine, guanethidine, etc.), $\alpha 1$ blockers (e.g., bunazosin, doxazosin, prazosin, terazosin, urapidil, etc.), $\beta$ blockers (e.g., propranolol, nadolol, timolol, nipradilol, bunitrolol, indenolol, penbutolol, carteolol, carvedilol, pindolol, acebutolol, atenolol, bisoprolol. metoprolol, labetalol, amosulalol, arotinolol, etc.), and the like], (2) vasodilators [calcium channel antagonists (e.g., manidipine, nicardipine, nilvadipine, nisoldipine, nitrendipine, benidipme, amlodipine, aranidipine, etc.), phthalazine derivatives (e.g., budralazine, cadralazine, ecarazine, hydralazine, todralazine, etc.), and the like], (3) ACE inhibitors [alacepril, captopril, cilazapril, delapril, enalapril, lisinopril, temocapril, trandolapril, quinapril, imidapril, benazepril, perindopril, etc.)], (4) All antagonists [losartan, candesartan, valsartan, telmisartan, irbesartan, forasartan, etc.], (5) diuretic drugs (e.g., diuretic drugs described above, etc.); antihypertensive drugs: diuretic drugs [e.g., furosemide (Lasix), bumetanide (Lunetoron), azosemide (DI-ART)], antihypertensive drugs [e.g., ACE inhibitors, (enalapril maleate (RENIVACE), etc.) and Ca antagonists (manidipine, amlodipine, etc.), $\alpha$ or $\beta$ receptor blockers, etc.], antihyperlipemia drugs [HMG-CoA reductase inhibitors (e.g., fluvastatin, cerivastatin, atorvastatin, etc.), fibrates [e.g., simfibrate, aluminum clofibrate, clinofibrate, fenofibrate, etc.], anion exchange resin (e.g., cholestyramine, etc.), nicotinic acid drugs (e.g., nicomol, niceritrol, tocopherol nicotinate, etc.), polyvalent unsaturated fatty acid derivatives (e.g., ethyl icosapentate, polyene phosphatidylcholine, melinamide, etc.), phytosterols (e.g., gamma-oryzanol, soy sterol, etc.), elastase, sodium dextran sulfate, squalene synthase inhibitors, CETP inhibitors, ethyl 2-chloro-3-[4-(2-methyl-2-phenylpropoxy)phenyl]propionate [Chem. Pharm. Bull., 38, 2792-2796 (1990)], etc.]; osseous disease drugs: calcium formulations (e.g., calcium carbonate, etc.), calcitonin formulations, activated vitamin $D_3$ formulations (e.g., alfacalcidol (Alfarol, etc.), calcitriol (Rocaltrol), etc.), sex hormones (e.g., estrogen, estradiol, etc.), hormone formulations [e.g., conjugated estrogen (Premann), etc.], ipriflavone formulations [Osten, etc.], vitamin $K_2$, vitamin $K_2$ formulations [e.g., menatetrenone (Glakay), etc.], bisphosphonate-based formulations (etidronate, etc.), prostaglandin E2, fluorine compounds (e.g., sodium fluoride, etc.), bone morphogenetic protein (BMP), fibroblast growth factor (FGF), platelet derived growth factor (PDGF), transforming growth factor (TGF-$\beta$), insulin-like growth factor-1 and -2 (IGF-1, -2), parathyroid adrenal hormones (PTH), and compounds described in EP-A1-376197, EP-A1-460488, and EP-A 1-719782 (e.g., (2R,4S)-(−)-N-[4-(diethoxyphosphorylmethyl)phenyl]-1,2,4,5-tetrahydro-4-methyl-7,8-methyl-enedioxy-5-oxo-3-benzothiepin-2-carboxamide, etc.), and the like, fat-soluble vitamin drugs [(1) vitamin A family: vitamin $A_1$, vitamin $A_2$, and retinol palmitate, (2) vitamin D family: vitamin $D_1$, $D_2$, $D_3$, $D_4$ and $D_5$, (3) vitamin E family: $\alpha$-tocopherol, $\beta$-tocopherol, $\gamma$-tocopherol, $\delta$-tocopherol, dl-$\alpha$-tocopherol nicotinate, (4) vitamin K family: vitamin $K_1$, $K_2$, $K_3$ and $K_4$, (5) folic acids (vitamin M, etc.); vitamin derivatives [various vitamin derivatives, e.g., vitamin $D_3$ derivatives such as 5,6-trans-cholecalciferol, 2,5-hydroxycholecalciferol, 1-$\alpha$-hydroxycholecalciferol, vitamin $D_2$ derivatives such as 5,6-trans-ergocalciferol, and the like]; disease-modifying antirheumatic and immunosuppressive drugs [e.g., methotrexate, leflunomide, prograf, sulfasalazine, D-penicillamine, oral gold drugs]; hypertensors [dopamine, dobutamine, denopamine, digitoxin, digoxin, methyldigoxin, lanatoside C, G-strophanthin, etc.]; myocardial protective drugs: heart ATP-K opener, Na-H exchange inhibitors, endothelin antagonists, urotensin antagonist, etc., cardiac failure drugs [cardiac stimulants (e.g., digitoxin, digoxin, methyldigoxin, lanatoside C, proscillaridin, etc.), $\alpha$, $\beta$ stimulants (e.g., epinephrine, norepinephrine, isoproterenol, dopamine, docarpamine, dobutamine, denopamine, etc.), phosphodiesterase inhibitors (e.g., anirinone, milrinone, olprinone hydrochloride, etc.), calcium channel sensitivity enhancer (e.g., pimobendan, etc.), nitrate drugs (e.g., nitroglycerin, isosorbide nitrate, etc.), ACE inhibitors (e.g., the ACE inhibitor described above, etc.), diuretic drugs (e.g., diuretic drugs described above, etc.), calperitide, ubidecarenone, vesnarinone, aminophylline, etc.]; neurotrophic factors; renal failure and nephropathy drugs; biological formulations [e.g., monoclonal antibodies (e.g., anti-TNF-$\alpha$ antibodies, anti-IL-12 antibodies, anti-IL-6 antibodies, anti-ICAM-I antibodies, anti-CD4 antibodies, etc.), soluble receptors (e.g., soluble TNF-$\alpha$ receptors, etc.), protein ligands (IL-I receptor antagonist, etc.)]; bile acid binding resins [e.g., cholestyramine, colestipol, etc.]; biliary tract disease drugs: cholepoietic drugs [e.g., dehydrocholic acid, etc.], cholekinetic drugs [e.g., magnesium sulfate, etc.], and the like; central nervous system agonists: antianxiety drugs, hypnotic and sedative drugs, anesthetic drugs, spasmolytic drugs, autonomic drugs, anti-Parkinson drugs and other psychoneuro drugs, etc.; antitussive and expectorants [ephedrine hydrochloride, noscapine hydrochloride, codeine phosphate, dihydrocodeine phosphate, isoproterenol hydrochloride, ephedrine hydrochloride, methylephedrine hydrochloride, alloclamide, clofedanol, picoperidamine, cloperastine, protokylol, isoproterenol, salbutamol, terbutaline, oxymetebanol, morphine hydrochloride, dextromethorphan hydrobromide, oxycodone hydrochloride, dimemorfan phosphate, tipepidine hibenzate, pentoxyverme citrate, clofedanol hydrochloride, benzonatate, guaifenesin, bromhexine hydrochloride, ambroxol hydrochloride, acetylcysteine, ethylcysteine hydrochloride, carbocisteine, etc.], sedative drugs [chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovaleryl urea, chloral hydrate, triclofos sodium, etc.], analgesic and antiphlogistic drugs [e.g., central analgesic drugs (e.g., morphine, codeine, pentazocine, etc.), steroidal drugs (e.g., prednisolone, dexamethasone, betamethasone, etc.), antiphlogistic enzymatic drugs (e.g., bromelain, lysozyrnes, proctase, etc.)], diabetic drugs [sulfonylurea drugs (e.g., tolbutamide, chlorpropamide, glyclopyramide, acetohexamide, tolazamide, glibenclamide, glibuzole, etc.), biguanide drugs (e.g., metformin hydrochloride, buformin hydrochloride, etc.), α-glucosidase inhibitors (e.g., voglibose, acarbose, etc.), insulin resistance improvers (e.g., pioglitazone, troglitazone, etc.), insulin, glucagon, diabetic complication drugs (e.g., epairestat, thioctic acid, etc.), actos, rosiglitazone, kinedak, penfill, humulin, euglucon, glimicron, daonil, novolin, monotard, insulin family, glucobay, dimelin, rastinone, bacilcon, deamelin S, Iszilin. etc.]; brain function activating agents (e.g., idebenone, vinpocetine, etc.); urinary and male genital disease drugs [e.g., prostatomegaly drugs (tamsulosin hydrochloride, prazosin hydrochloride, chlormadinone acetate, etc.), prostate cancer drugs (leuprorelin acetate, gosereim acetate, chlormadinone acetate, etc.)], etc; nonsteroidal antiinflan-imatory drugs [acetaminophen, phenacetin, ethenzamide, sulpyrine, antipyrine, migrenin, aspirin, mefenamic acid, fulfenamic acid, diclofenac sodium, loxoprofen sodium, phenylbutazone, indometacin, ibuprofen, ketoprofen, naproxen, oxaprozin, flurbiprofen, fenbufen, pranoprofen, floctafenine, epirizole, tiaramide hydrochloride, zaltoprofen, gabexate mesilate, camostat mesilate, urinastatin, coichicine, probenecid, sulfmpyrazone, benzbromarone, allopurinol, sodium aurothiomalate, sodium hyaluronate, sodium salicylate, morphine hydrochloride, salicylic acid, atropine, scopolamine, morphine, pethidine, levorphanol, ketoprofen, naproxen, oxymorphone or salts thereof, etc.]; frequent urination and incontinence drugs [flavoxate hydrochloride, etc.]; unstable plaque stabilizers [MMP inhibitors, chymase inhibitors, etc.]; arrhythmic drugs [sodium channel blockers (e.g., quinidine, procainamide, disopyramide, ajmaline, cibenzoline, lidocaine, diphenylhydantoin, mexiletine, propafenone, flecainide, pilsicainide, phenytoin, etc.), βblockers (e.g., propranolol, aiprenolol, bufetolol, oxprenolol, atenolol, acebutolol, metoprolol, bisoprolol, pindolol, carteolol, arotinolol, etc.), potassium channel blockers (e.g., amiodarone, etc.), calcium channel blockers (e.g., verapamil, diltiazem, etc.), and the like]; gynecologic disease drugs [e.g., climacteric disorder drugs (conjugated estrogen, estradiol, testosterone enanthate, estradiol valerate, etc.), breast cancer drugs (tamoxifen citrate, etc.), endometriosis and hysteromyoma drugs (leuprorelin acetate, danazol, etc.)], etc.; anesthetic drugs [a. local anaesthetic drugs [cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine], etc.]; b. systemic anesthetic drugs [(1) inhalation anesthetic drugs (e.g., ether, halothane, nitrous oxide, influrane, enflurane), (2) intravenous anesthetic drugs (e.g., ketamine hydrochloride, droperidol, thiopental sodium, thiamylal sodium, pentobarbital), etc.]]; anesthetic antagonists [levallorphan, nalorphine, naloxone, or salts thereof, etc.]; chronic cardiac failure drugs: cardiac stimulants [e.g., cardiac glycoside (digoxin), etc., β receptor stimulants (catecholamine preparations such as denopamine, dobutamine), PDE inhibitors, etc.]; diuretic drugs [e.g., furosemide (Lasix), spironolactone (Aldactone), bumetanide (Lunetoron), azosemide (Diart), etc.]; ACE inhibitors [e.g., enalapril maleate (Renivace), etc.]; Ca antagonists [e.g., amlodipine, manidipme, etc.]and β receptor blockers, etc.; inimunomodulators [cyclosporin, tacrolimus, gusperimus, azathioprine, antilymphocyte sera, dried sulfonated immunoglobulins, erythropoietins, growth promoting glycoproteins, interleukins, interferons, etc.]; diuretic drugs [thiazide-based diuretic drugs (benzylhydrochlorothiazide, cyclopenthiazide, ethiazide, hydrochlorothiazide, hydroflumethiazide, methyclothiazide, penfluthiazide, polythiazide, trichlormethiazide, etc.), loop diuretic drugs (chlortalidone, clofenamide, indapamide, mefruside, meticrane, tripamide, quinethazone, metolazone, furosemide, mefruside, etc.), potassium-sparing diuretic drugs (spironolactone, triamterene, etc.)]; erectile dysfunction drugs (Viagra, apomorphine, etc.); and the like.

cyclooxygenase inhibitors [Cox-I, Cox-II inhibitors such as celecoxib, rofecoxib, salicylic acid derivatives such as aspirin and the like, diclofenac, indometacin, loxoprofen, etc.]; signal transduction inhibitors, squalene epoxidase inhibitors [e.g., NB-598 and the analogous compounds, etc.]; steroidal drugs [dexamethasone, hexestrol, methimazole, betamethasone, triamcinolone, triamcinolone acetonide, fluocinonide, fluocinolone acetonide, prednisolone, methylprednisolone, cortisone acetate, hydrocortisone, fluorometholone, beclomethasone propionate, estriol, etc.]; diacerin; nicotinic acid and derivatives and analogues thereof [e.g., acipimox and probucol]; nicergoline, nephrotic syndrome drugs: prednisolone (Predonine), prednisolone sodium succinate (Predonine), methylprednisolone sodium succinate (Solumedrol), betamethasone (Rinderon), dipyridamole (Persantine), dilazep hydrochloride (Comelian), ticlopidine, clopidogrel, antiplatelet drugs and anticoagulants such as FXa inhibitors, etc.; barpital-based anticonvulsants or anaesthetic drugs (phenobarbital, mephobarbital, metharbital, etc.); Parkinson's disease drugs (e.g., L-DOPA, etc.); histamine receptor blockers (cimetidine, famotidine, etc.); hydantoin-based anticonvulsant drugs (phenytoin, mephenytoin, ethotoin, etc.); piroxicam, fibrates [e.g., clofibrate, benzafibrate, gemfibrozil, etc.]; prostaglandins; megestrol acetate; gastric and intraduodenal ulcer drugs: antacids [e.g., histamine H2 antagonists (cimetidine, etc.), proton pump inhibitors (lansoprazole, etc.), and the like]; inflammatory mediator inhibitors; coronary vasodilators: nifedipine, diltiazem, nicoradil, nitrite drugs, etc.; infectious disease drugs: [e.g., antibiotic formulations (cefotiam hydrochloride, cefozopran hydrochloride, ampicillin, etc.), chemotherapeutic agents (sulfa drugs, synthetic antibacterial agents, antiviral agents, etc.), biologic formulations (vaccines, blood preparations including immunoglobulins) etc.] etc.; hepatic disease drugs: glycyrrhizin formulations [e.g., Stronger Minophagen, etc.]; liver hydrolysate; SH compounds [e.g., glutathione, etc.]; special amino acid formulations [e.g., aminoleban, etc.]; phospholipids [e.g., polyenephosphatidylcholine, etc.]; vitamins [e.g., vitamin $B_1$, $B_2$, $B_6$, $B_{12}$, C, etc.]; adrenocortical hormones [e.g., dexamethasone, betamethasone, etc.]; interferons [e.g., interferon α, β, etc.]; hepatic encephalopathy drugs [e.g., lactulose, etc.]; hemostatic agents used in cases of rupture of esophageal and gastric varices [e.g., vasopressin, somatostatin, etc.] etc.; arthritis drugs; muscle relaxants [pridinol, tubocurarine, pancuronium, tolperisone hydrochloride, chlorphenesin carbamate, baclofen, chlormezanone, mephenesin, chlorzoxazone, eperisone, tizanidine, etc.]; vasodilators [oxyfedrine, diltiazem, tolazoline, hexobendine, bamethan, clonidine, methyldopa, guanabenz, etc.]; vasoconstrictors [dopamine, dobutamine, denopamine, etc.]; platelet coagulation inhibitors (ozagrel, etc.); thrombogenesis prophylactic and/or therapeutic drugs: anticoagulant drugs [e.g., heparin sodium, heparin calcium, warfarin calcium (Warfarin), Xa inhibitors]; thrombolytic drugs [e.g., tPA, urokinase]; antiplatelet drugs [e.g., aspirin, sulfinpyrazone (Anturan), dipyridamole (Persantine), ticlopidine (Panaldine), cilostazol (Pletal), GPIIb/IIIa antagonists (ReoPro)]; antidepressants [imipramine, clomipramine, noxiptiline, fenelzin, amitriptyline hydrochloride, nortriptyline hydrochloride, amoxapine, mianserin hydrochloride, maprotiline hydrochloride, sulpiride, fluvoxamine maleate, trazodone hydrochloride, etc.]; antiepileptic drugs [gabapentin, phenytoin, ethosuximide, acetazolamide, chlordiazepoxide, trimethadione, carbamazepine, phenobarbital, primidone, sultiame, sodium valproate, clonazepam, diazepam, nitrazepam, etc.]; anti-allergic drugs [diphenhydramine, chlorpheniramine, tripelennamine, methodilamine, clemizole, diphenylpyraline, methoxyphenamine, sodium cromoglycate, tranilast, repirinast, amlexanox, ibudilast, ketotifen, terfenadine, mequitazine, azlastine, epinastine, ozagrel hydrochloride, pranlukast hydrate, seratrodast, fexofenadine, ebastine, bucillamine, oxatomide, Stronger Neo-Minophagen C, tranexamic acid, ketotifen fumarate, etc.]; anticholinergic drugs (e.g., ipratropium bromide, flutropium bromide, oxitropium bromide, etc.); anti-Parkinson drugs (dopamine, levodopa, etc.); anti-rheumatic drugs; anti-inflammatory drugs (e.g., aspirin, acetaminophen, diclofenac sodium, ibuprofen, indometacin, loxoprofen sodium, dexamethasone, etc.); anticoagulant and antiplatelet drugs [sodium citrate, activated protein C, tissue factor pathway inhibitors, antithrombin III, dalteparin sodium, argatroban, gabexate, ozagrel sodium, ethyl icosapentate, beraprost sodium, alprostadil, pentoxifylline, tisokinase, streptokinase, hebarin, etc.]; anticoagulant therapeutic drugs [dipyridamole (Bersantine), dilazep hydrochloride (Comelian), ticlopidine, clopidogrel, Xa inhibitors]; antibacterial drugs [(1) sulfa drugs [sulfamethizole, sulfisoxazole, sulfamonomethoxine, sulfamethizole, salazosulfapyridine, sulfadiazine silver, etc.], (2)quinoline-based antibacterial drugs [nalidixic acid, pipemidic acid trihydrate, enoxacin, norfloxacin, ofloxacin, tosufloxacin tosilate, ciprofloxacin hydrochloride, lomefloxacin hydrochloride, sparfloxacin, fleroxacin, etc.], (3) antituberculous drugs [isoniazid, ethambutol (ethambutol hydrochloride), p-aminosalicylic acid (calcium p-aminosalicylate), pyrazinamide, ethionamide, prothionamide, rifampicin, streptomycin sulfate, kanamycin sulfate, cycloserine, etc.], (4) anti-acid fast bacterial drugs [diaphenylsulfone, rifampicilin, etc.], (5) antiviral drugs [idoxuridine, acyclovir, vidarabine, ganciclovir, etc.], (6) anti-HIV drugs [zidovudine, didanosine, zalcitabine, indinavir sulfate ethanolate, ritonavir, etc.], (7) spirocheticide, (8) antibiotics [tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotiam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or salts thereof, griseofulvin, lankacidins [J. Antibiotics, 38, 877-885 (1985)], etc.], cefixime, levofloxacin]; antithrombotic drugs (argatroban, etc.); antiprotozoal drugs [metronidazole, tinidazole, diethylcarbamazine citrate, quinine hydrochloride, quinine sulfate, etc.]; antitumor drugs [6-O—(N-chloroacetylcarbamoyl) fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuplin acetate, buserelin acetate, etc.]; antifungal drugs [(1) polyethylene-based antibiotics (e.g., amphotericin B, nystatin, trichomycin), (2) griseofulvin, pyrrolnitrin, etc., (3) cytosine metabolism antagonists (e.g., flucytosine), (4) imidazole derivatives (e.g., econazole, clotrimazole, miconazole nitrate, bifonazole and croconazole), (5) triazole derivatives (e.g., fluconazole, itoraconazole, azole compounds [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl-3-(2H,4H)-1,2,4-triazolone], (6) thiocarbamate derivatives (e.g., trinaphthol], (7) echinocandin-based derivatives (e.g., caspofungin, FK-463, V-echinocandin), etc.]; antipsychotic drugs [chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine, etc.]; antiulcer drugs [metoclopramide, histidine hydrochloride, lansoprazole, metoclopramide, pirenzepine, cimetidine, ranitidine, famotidine, urogastron, oxethazaine, proglumide, omeprazole, sucralfate, sulpiride, cetraxate, gefarnate, aldioxa, teprenone, prostaglandins, etc.]; anti-diabetic drugs [e.g., pioglitazone, nateglinide, voglibose, acarbose, etc.]; antiobesity drugs (mazindol, etc.); antirheumatic drugs, etc.; antianxiety drugs [diazepam, lorazepam, oxazepam, chlordiazepoxide, medazepam, oxazolam, cloxazolam, clotiazepam, bromazepam, etizolam, fludiazepam, hydroxyzine, etc.]; antiarrhythmic drugs: disopyramide, lidocaine, quinidine sulfate, flecainide acetate, mexiletine hydrochloride, amiodarone hydrochloride, and β blockers, Ca antagonists, etc.; antiasthmatic drugs [isoprenaline hydrochloride, salbutamol sulfate, procaterol hydrochloride, terbutaline sulfate, trimetoxynol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglycate, tranilast, repirinast, amlexanox, ibudilast, ketotifen, terfenadine, mequitazine, azelastine, epinastine, ozagrel hydrochloride, pranlukast hydrate, seratrodast, dexamethasone, prednisolone, hydrocortisone, beclomethasone propionate, fluticasone propionate, beclomethasone propionate, procaterol, etc.]; anti-hypothyroidism drugs [dried thyroid (Thyreoid), levothyroxine sodium (Thyradin S), liothyronine sodium (thyronine, tyronamine)]; nephrotic syndrome drugs [prednisolone (Predonine), prednisolone sodium succinate (Predonine), methylprednisolone sodium succinate (Solumedrol), betamethasone (Rinderon)]; antihypertensive drugs [(1) sympathetic nerve inhibitors [α2 stimulants (e.g., clonidine, guanabenz, guanfacine, methyldopa, etc.), ganglionic blockers (e.g., hexamethonium, trimethaphan, etc.), presynaptic blockers (e.g., ARSA-Oxylone, dimethylaminoreserpinate, rescinnamine, reserpine, syrosingopine, etc.), neuronal blockers (e.g., betanidine, guanethidine, etc.), α1 blockers (e.g., bunazosin, doxazosin, prazosin, terazosin, urapidil, etc.), β blockers (e.g., propranolol, nadolol, timolol, nipradilol, bunitrolol, indenolol, penbutolol, carteolol, carvedilol, pindolol, acebutolol, atenolol, pisoprolol, metoprolol, labetalol, amosulalol, arotinolol, etc.), and the like], (2) vasodilators [calcium channel antagonists (e.g., manidipine, nicardipine, nilvadipine, nisoldipine, nitrendipine, benidipine, amlodipine, aranidipine, etc.), phthalazine derivatives (e.g., budralazine, cadralazine, ecarazine, hydralazine, todralazine, etc.), and the like], (3) ACE inhibitors [alacepril, captopril, cilazapril, delapril, enalapril, lisinopril, temocapril, trandolapril, quinapril, imidapril, benazepril, perindopril, etc.)], (4) AII antagonists [losartan, candesartan, valsartan, telmisartan, irbesartan, forasartan, etc.], (5) diuretic drugs (e.g., diuretic drugs described above, etc.); antihypertensive drugs: diuretic drugs [e.g., furosemide (Lasix), bumetanide (Lunetoron), azosemide (DIART)], antihypertensive drugs [e.g., ACE inhibitors, (enalapril maleate (RENIVACE), etc.) and Ca antagonists (manidipine, amlodipine, etc.), α or β receptor blockers, etc.], antihyperlipemia drugs [HMG-CoA reductase inhibitors (e.g., fluvastatin, cerivastatin, atorvastatin, etc.), fibrates [e.g., simfibrate, aluminum clofibrate, clinofibrate, fenofibrate, etc.], anion exchange resin (e.g., cholestyramine, etc.), nicotinic acid drugs (e.g., nicomol, niceritrol, tocopherol nicotinate, etc.), polyvalent unsaturated fatty acid derivatives (e.g., ethyl icosapentate, polyene phosphatidylcholine, melinamide, etc.), phytosterols (e.g., gamma-oryzanol, soy sterol, etc.), elastase, sodium dextran sulfate, squalene synthase inhibitors, CETP inhibitors, ethyl 2-chloro-3[4-(2-methyl-2-phenylpropoxy)phenyl]propionate [Chem. Pharm. Bull., 38, 2792-2796 (1990)], etc.]; osseous disease drugs: calcium formulations (e.g., calcium carbonate, etc.), calcitonin formulations, activated vitamin $D_3$ formulations (e.g., alfacalcidol (Alfarol, etc.), calcitriol (Rocaltrol), etc.), sex hormones (e.g., estrogen, estrandiol, etc.), hormone formulations [e.g., conjugated estrogen (Premarin), etc.], ibriflavone formulations [Osten, etc.], vitamin $K_2$, vitamin $K_2$ formulations [e.g., menatetrenone (Glakay), etc.], bisphosphonate-based formulations (etidronate, etc.), prostaglandin E2, fluorine compounds (e.g., sodium fluoride, etc.), bone morphogenetic protein (BMP), fibroblast growth factor (FGF), platelet derived growth factor (PDGF), transforming growth factor (TGF-β), insulin-like growth factor-1 and -2 (IGF-1, -2), parathyroid adrenal hormones (PTH), and compounds described in EP-A1-376197, EP-A1-460488, and EP-A1-719782 (e.g., (2R,4S)-(−)-N-[4-(diethoxyphosphorylmethyl)phenyl]-1,2,4,5-tetrahydro-4-methyl-7,8-methylenedioxy-5-oxo-3-benzothiepin-2-carboxamide, etc.), and the like, fat-soluble vitamin drugs [(1) vitamin A family: vitamin $A_1$, vitamin $A_2$, and retinol palmitate, (2) vitamin D family: vitamin $D_1$, $D_2$, $D_3$, $D_4$ and $D_5$, (3) vitamin E family: α-tocopherol, β-tocopherol, γ-tocopherol, δ-tocopherol, dl-α-tocopherol nicotinate, (4) vitamin K family: vitamin $K_1$, $K_2$, $K_3$ and $K_4$, (5) folic acids (vitamin M, etc.); vitamin derivatives [various vitamin derivatives, e.g., vitamin $D_3$ derivatives such as 5,6-trans-cholecalciferol, 2,5-hydroxycholecalciferol, 1-α-hydroxycholecalciferol, vitamin $D_2$ derivatives such as 5,6-trans-ergocalciferol, and the like]; disease-modifying antirheumatic and immunosuppressive drugs [e.g., methotrexate, leflunomide, prograf, sulfasalazine, D-penicillamine, oral gold drugs]; hypertensors [dopamine, dobutamine, denopamine, digitoxin, digoxin, methyldigoxin, lanatoside C, G-strophanthin, etc.]; myocardial protective drugs: heart ATP—K opener, Na—H exchange inhibitors, endothelin antagonists, urotensin antagonist, etc., cardiac failure drugs [cardiac stimulants (e.g., digitoxin, digoxin, methyldigoxin, lanatoside C, proscillaridin, etc.), α, β stimulants (e.g., epinephrine, norepinephrine, isoproterenol, dopamine, docarpamine, dobutamine, denopamine, etc.), phosphodiesterase inhibitors (e.g., amrinone, milrinone, olprinone hydrochloride, etc.), calcium channel sensitivity enhancer (e.g., pimobentan, etc.), nitrate drugs (e.g., nitroglycerin, isosorbide nitrate, etc.), ACE inhibitors (e.g., the ACE inhibitor described above, etc.), diuretic drugs (e.g., diuretic drugs described above, etc.), calperitide, ubidecarenone, vesnarinone, aminophylline, etc.]; neurotrophic factors; renal failure and nephropathy drugs; biological formulations [e.g., monoclonal antibodies (e.g., anti-TNF-α antibodies, anti-IL-12 antibodies, anti-IL-6 antibodies, anti-ICAM—I antibodies, anti-CD4 antibodies, etc.), soluble receptors (e.g., soluble TNF-α receptors, etc.), protein ligands (IL-I receptor antagonist, etc.)]; bile acid binding resins [e.g., cholestyramine, colestipol, etc.]; biliary tract disease drugs: cholepoietic drugs [e.g., dehydrocholic acid, etc.], cholekinetic drugs [e.g., magnesium sulfate, etc.], and the like; central nervous system agonists: antianxiety drugs, hypnotic and sedative drugs, anesthetic drugs, spasmolytic drugs, autonomic drugs, anti-Parkinson drugs and other psychoneuro drugs, etc.; antitussive and expectorants [ephedrine hydrochloride, noscapine hydrochloride, codeine phosphate, dihydrocodeine phosphate, isoproterenol hydrochloride, ephedrine hydrochloride, methylephedrine hydrochloride, alloclamide, clofedanol, picoperidamine, cloperastine, protokylol, isoproterenol, salbutamol, terbutaline, oxymetebanol, morphine hydrochloride, dextromethorphan hydrobromide, oxycodone hydrochloride, dimemorfan phosphate, tipepidine hibenzate, pentoxyverine citrate, clofedanol hydrochloride, benzonatate, guaifenesin, bromhexine hydrochloride, ambroxol hydrochloride, acetylcysteine, ethylcysteine hydrochloride, carbocisteine, etc.], sedative drugs [chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovaleryl urea, chloral hydrate, triclofos sodium, etc.], analgesic and antiphlogistic drugs [e.g., central analgesic drugs (e.g., morphine, codeine, pentazocine, etc.), steroidal drugs (e.g., prednisolone, dexamethasone, betamethasone, etc.), antiphlogistic enzymatic drugs (e.g., bromelain, lysozymes, proctase, etc.)], diabetic drugs [sulfonylurea drugs (e.g., tolbutamide, chlorpropamide, glyclopyramide, acetohexamide, tolazamide, glibenclamide, glibuzole, etc.), biguanide drugs (e.g., metformin hydrochloride, buformin hydrochloride, etc.)

α-glucosidase inhibitors (e.g., voglibose, acarbose, etc.), insulin resistance improvers (e.g., pioglitazone, troglitazone, etc.), insulin, glucagon, diabetic complication drugs (e.g., epalrestat, thioctic acid, etc.), actos, rosiglitazone, kinedak, penfill, humulin, euglucon, glimicron, daonil, novolin, monotard, insulin family, glucobay, dimelin, rastinone, bacilcon, deamelin S, Iszilinacid, etc.]; brain function activating agents (e.g., idebenone, vinpocetine, etc.); urinary and male genital disease drugs [e.g., prostatomegaly drugs (tamsulosin hydrochloride, prazosin hydrochloride, chlormadinone acetate, etc.), prostate cancer drugs (leuprorelin acetate, goserelin acetate, chlormadinone acetate, etc.)], etc; nonsteroidal antiinflammatory drugs [acetaminophen, phenacetin, ethenzamide, sulpyrine, antipyrine, migrenin, aspirin, mefenamic acid, fulfenamic acid, diclofenac sodium, loxoprofen sodium, phenylbutazone, indometacin, ibuprofen, ketoprofen, naproxen, oxaprozin, flurbiprofen, fenbufen, pranoprofen, floctafenine, epirizole, tiaramide hydrochloride, zaltoprofen, gabexate mesilate, camostat mesilate, urinastatin, colchicine, probenecid, sulfinpyrazone, benzbromarone, allopurinol, sodium aurothiomalate, sodium hyaluronate, sodium salicylate, morphine hydrochloride, salicylic acid, atropine, scopolamine, morphine, pethidine, levorphanol, ketoprofen, naproxen, oxymorphone or salts thereof, etc.]; frequent urination and incontinence drugs [flavoxate hydrochloride, etc.]; unstable plaque stabilizers [MMP inhibitors, chymase inhibitors, etc.]; arrhythmic drugs [sodium channel blockers (e.g., quinidine, procainamide, disopyramide, ajmaline, cibenzoline, lidocaine, diphenylhydantoin, mexiletine, propafenone, flecainide, pilsicainide, phenytoin, etc.), β blockers (e.g., propranolol, alprenolol, bufetolol, oxprenolol, atenolol, acebutolol, metoprolol, pisoprolol, pindolol, carteolol, arotinolol, etc.), potassium channel blockers (e.g., amiodarone, etc.), calcium channel blockers (e.g., verapamil, diltiazem, etc.), and the like]; gynecologic disease drugs [e.g., climacteric disorder drugs (conjugated estrogen, estradiol, testosterone enanthate, estradiol valerate, etc.), breast cancer drugs (tamoxifen citrate, etc.), endometriosis and hysteromyoma drugs (leuprorelin acetate, danazol, etc.)], etc.; anesthetic drugs [a. local anaesthetic drugs [cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine], etc.]; b. systemic anesthetic drugs [(1) inhalation anesthetic drugs (e.g., ether, halothane, nitrous oxide, influrane, enflurane), (2) intravenous anesthetic drugs (e.g., ketamine hydrochloride, droperidol, thiopental sodium, thiamylal sodium, pentobarbital), etc.]]; anesthetic antagonists [levallorphan, nalorphine, naloxone, or salts thereof, etc.]; chronic cardiac failure drugs: cardiac stimulants [e.g., cardiac glycoside (digoxin), etc., β receptor stimulants (catecholamine preparations such as denopamine, dobutamine), PDE inhibitors, etc.]; diuretic drugs [e.g., furosemide (Lasix), spironolactone (Aldactone), bumetanide (Lunetoron), azosemide (Diart), etc.]; ACE inhibitors [e.g., enalapril maleate (Renivace), etc.]; Ca antagonists [e.g., amlodipine, manidipine, etc.] and β receptor blockers, etc.; immunomodulators [cyclosporin, tacrolimus, gusperimus, azathioprine, antilymphocyte sera, dried sulfonated immunoglobulins, erythropoietins, growth promoting glycoproteins, interleukins, interferons, etc.]; diuretic drugs [thiazide-based diuretic drugs (benzylhydrochlorothiazide, cyclopenthiazide, ethiazide, hydrochlorothiazide, hydroflumethiazide, methyclothiazide, penfluthiazide, polythiazide, trichlormethiazide, etc.), loop diuretic drugs (chlortalidone, clofenamide, indapamide, mefruside, meticrane, sotrazone, tribamide, quinethazone, metolazone, furosemide, mefruside, etc.), potassium-sparing diuretic drugs (spironolactone, triamterene, etc.)]; erectile dysfunction drugs (Viagra, apomorphine, etc.); and the like.

These drugs may be formulated, separately or simultaneously, by mixing with pharmaceutically acceptable carriers, excipients, binders, diluents or the like, and can be administered either orally or parenterally. When the drugs are formulated separately, the separately prepared formulations may be mixed using a diluent or the like at the time of use and then administered, or each of the separately prepared formulations may be administered, simultaneously or separately with a time interval, to the same subject. Kit products that are to be used for mixing the separately prepared formulations using a diluent or the like at the time of use and administering (for example, an injection kit including ampoules for containing individual powdery drug, and a diluent for mixing and dissolving two or more drugs at the time of use, and the like), kit products that are to be used for administering each of the separately prepared formulations, simultaneously or separately with a time interval, to the same subject (for example, a tablet kit for administering two or more tablets, simultaneously or separately with a time interval, each tablet containing each of the drugs and placed in the same or separate bags, with space for memorandum provided, if necessary, on the bags for indication of the drug administration time, or the like), and the like are also included to the pharmaceutical composition of the present invention.

Dosage of the pharmaceutical composition of the present invention can be appropriately selected by taking into consideration of the subject to be administered, age and body weight of the subject, symptoms, administration time, administration route, dosage form and the like.

The dosage of a particular subject can be determined according to the subject's age, body weight, general health condition, gender, meal, administration time, administration route, excretion rate and the extent of disease condition of the patient at the time of treatment, by taking into consideration of these and other factors.

When the pharmaceutical composition described above is used as a prophylactic and therapeutic agent for AIDS and as a suppressive agent for disease progression of AIDS, the dosage may vary depending on the patient's condition, body weight or the method of administration. However, in the case of oral administration, the daily dosage is in a range of about 5 to 1000 mg, preferably about 10 to 600 mg, more preferably about 10 to 300 mg, and particularly preferably about 15 to 150 mg, as the active ingredient [i.e. as the compound of the formula (I)], for an adult having a body weight of 50 kg, and the composition is administered once, or in 2 or 3 divided doses a day.

When the pharmaceutical composition described above is used as a prophylactic and therapeutic agent for graft versus host disease and/or rejection associated with transplantation of organ such as heart, kidney, liver, bone marrow or the like, administration of the composition starts three days before the transplantation and is continued even after the transplantation. The daily dosage of the pharmaceutical composition of the present invention may vary depending on the patient's condition, body weight or method of administration, but in the case of oral administration, it is about 5 to 1000 mg, preferably about 10 to 600 mg, more preferably about 10 to 300 mg, and particularly preferably about 15 to 150 mg, as the active ingredient [i.e., as the compound represented by the formula (I)], for an adult having a body weight of 50 kg, and the composition is administered once, or in 2 or 3 divided doses a day. In this case, the composition may also be used in combination with other suppressive agents for graft versus host disease and/or rejection associated with organ transplantation. Specific examples of the suppressive agent for graft versus host disease and/or rejection associated with organ transplantation, which are used in combination with the compound represented by the above formula (I) or a salt thereof, include cyclosporin, tacrolimus, rapamycin, steroids, azathioprine, mycophenolate mofetil, mizoribine, etc. In the case of using these drugs in combination, if one of the drugs interferes with metabolism of other drugs, the dosage of each drug is to be appropriately adjusted, but in general, the dosage for administration of a single drug is employed for each of the drugs.

When the compound represented by the formula (I) described above or a salt thereof is used for diseases other than the suppressive agents for graft versus host disease and/or rejection associated with organ transplantation, the daily dosage thereof may vary depending on the kind of the disease to be treated, the patient's condition, body weight, or method of administration. But, in the case of oral administration, the dosage is about 5 to 1000 mg, preferably about 10 to 600 mg, more preferably about 10 to 300 mg, and particularly preferably about 15 to 150 mg, as the active ingredient [i.e., as the compound represented by the formula (I)], for an adult having a body weight of 50 kg, and the composition is administered once, or in 2 or 3 divided doses a day. When the compound is used in combination with other drugs, the dosage of the other drugs is appropriately selected in a range of, for example, about 1/200 to 1/2 or more and about 2 to 3 times or less of a general dosage. Further, in the case of using the compound in combination with two or more drugs, if one of the drugs interferes with metabolism of the other drugs, the dosage of each drug is to be appropriately adjusted, but in general, the dosage for administration of a single drug is employed for each of the drugs.

Furthermore, the compound represented by the formula (I) or a salt thereof can be also included in or used in combination with blood for transfusion or blood derivatives. Blood for transfusion or blood derivatives are usually produced by mixing blood obtained from a plurality of persons, and in some cases, cells infected by HIV virus may be co-present with HIV-uninfected cells. In such a case, there is fear for infection of the uninfected cells. Thus, when the compound represented by the formula (I) of the present invention is added to blood for transfusion or a blood derivative, it is possible to prevent or control infection and proliferation of the virus. Especially, upon storage of blood derivatives, addition of the compound represented by the formula (I) of the present invention is effective for prevention or control of infection and proliferation of the virus. In addition, when blood for transfusion or a blood derivative contaminated with HIV virus is administered to a person, infection and proliferation of the HIV virus in the body of the person administered with blood for transfusion or a blood derivative can be prevented by the compound represented by the formula (I) that has been added to the blood for transfusion or blood derivative. For example, in the case of orally administering the compound to an adult (body weight of about 60 kg) for preventing HIV infection upon blood transfusion and use of blood derivatives, the dosage for a single administration is usually in a range of about 0.02 to 50 mg/kg, preferably 0.05 to 30 mg/kg, and more preferably 0.1 to 10 mg/kg, as the CCR antagonist, and the compound is preferably administered in about 1 to about 3 doses a day. As a matter of fact, the range of dosage can be adjusted on the basis of the unit dosage necessary for dividing the daily dosage; however, as described above, the dosage can be determined by taking into consideration of the nature and severity of the disease, the patient's age, the body weight, the general health condition, the gender, the meal, the administration time, the method of administration, the excretion rate and other factors. In this case, the method of administration can be also appropriately selected, and the above-described prophylactic agent for HIV infection of the present invention may be added directly to the blood or blood derivative to be transfused, prior to blood transfusion or use of blood derivative. In such a case, the addition of the compound is preferably carried out immediately before to 24 hours before, preferably immediately before to 12 hours before, and more preferably immediately before to 6 hours before, the transfusion or use of blood derivative.

When the prophylactic agent for HIV infection of the present invention is further administered in addition to the blood or blood derivative to be transfused, at the time of blood transfusion or use of blood derivative, the agent is preferably administered from 1 hour before to simultaneously with transfusion or use of blood derivative, and more preferably, the agent is administered 1 to 3 times per day, continuously for 4 weeks.

Moreover, when the compound represented by the formula (I) or a salt thereof is used in combination with a reverse transcriptase inhibitor and/or a protease inhibitor, the dosage of the reverse transcriptase inhibitor or the protease inhibitor is properly selected in a range of about 1/200 to 1/2 or more, to about 2 to 3 times or less of the usual dosage.

The usual dosages of the representative reverse transcriptase inhibitors and protease inhibitors are as follows:

zidovudine: 100 mg didanosine: 125 to 200 mg zalcitabine: 0.75 mg lamivudine: 150 mg stavudine: 30 to 40 mg saquinavir: 600 mg ritonavir: 600 mg indinavir: 800 mg nelfinavir: 750 mg A typical embodiment of combined use of the compound of the formula (I) or a salt thereof, and a reverse transcriptase and/or a protease inhibitor will be described below.

(1) About 10 to 300 mg of the compound of the formula (I) or the salt thereof and about 50 to 200 mg of zidovudine, per an adult of body weight of 50 kg, are administered in combination to the same object. Each medicine may be administered simultaneously or separately in a time interval of less than 12 hours.

(2) About 10 to 300 mg of the compound of the formula (I) or the salt thereof and about 300 to 1200 mg of saquinavir, per an adult of body weight of 50 kg, are administered in combination to the same object. Each medicine may be administered simultaneously or separately in a time interval of less than 12 hours.

The following Examples, Reference Examples, Experimental Example and Formulation Examples further illustrate the present invention in detail but are not to be construed to limit the scope thereof.

EXAMPLE 1

Preparation of Compound 1

(S)-4-(((1-propylimidazol-5-yl)methyl)sulfinyl)aniline di-p-toluoyl-D-tartrate monohydrate (479 mg) was dissolved in ethyl acetate (5 ml) and 1 N hydrochloric acid (2.44 ml), followed by separation. To the aqueous layer was added an aqueous 25% potassium carbonate solution (2.44 ml), followed by extraction with 2-propanol-ethyl acetate (1:4) twice. The organic layers were combined, washed with saturated brine and dried over magnesium sulfate, and then the solvent was distilled off under reduced pressure. To the resulting residue was added tetrahydrofuran, and then the solvent was again distilled off under reduced pressure-to give (S)-(4-(((1-propylimidazol-5-yl)methyl)sulfinyl) aniline. Then, to a solution of 3-[4-(2-butoxyethoxy)phenyl]-10-isobutyl-7,8,9,10-tetrahydropyrido[2,3-b]azocine-6-carboxylic acid (250 mg) in dichloromethane (10 ml) were added a drop of DMF, and then oxalyl chloride (0.063 ml) at 0° C. The mixture was returned to room temperature and stirred for 30 minutes under a nitrogen atmosphere, and then the resulting solution was added dropwise to a solution of (S)-4-(((1-propylimidazol-5-yl)methyl)sulfinyl)aniline and pyridine (1.16 ml) in tetrahydrofuran (10 ml) at 0° C. under a nitrogen atmosphere. The mixture was returned to room temperature and stirred overnight. Then, water was added and the mixture was extracted with ethyl acetate. The organic layer was washed with water twice and saturated brine once, and then dried over magnesium sulfate. The solvent was distilled off under reduced pressure, and then the residue was separated and purified by basic silica gel column chromatography (ethyl acetate→methanol:ethyl acetate=3: 100) to give (S)-3-[4-(2-butoxyethoxy)phenyl]-10-isobutyl-N-[4-[[(1-propyl-1H-imidazol-5-yl)methyl]sulfinyl]phenyl]-7,8,9,10-tetrahydropyrido[2,3-b]azocine-6-carboxamide (294 mg) (Compound 1) as a yellow amorphous material.

$^1$H-NMR (300 MHz, CDCl$_3$) δ 0.90-0.96 (12H, m), 1.33-1.46 (2H, m), 1.50-1.76 (6H, m), 2.20-2.35 (1H, m), 2.58-2.67 (2H, m), 3.30-3.50 (2H, m), 3.55 (2H, t, J=6.9 Hz), 3.58-3.63 (2H, m), 3.76-3.82 (4H, m), 4.00 (1H, d, J=11.7 Hz), 4.09-4.17 (3H, m), 6.54 (1H, s), 6.97 (2H, d, J=9.0 Hz), 7.34 (2H, d, J=8.4 Hz), 7.40 (2H, d, J=9.0 Hz), 7.42-7.44 (2H, m), 7.55 (1H, s), 7.75 (2H, d, J=8.4 Hz), 8.15 (1H, s), 8.30 (1H, d, J=2.7 Hz).

Elementary analysis: C$_{40}$H$_{51}$N$_5$O$_4$S.0.5H$_2$O, Calcd. C, 67.96; H, 7.41; N, 9.91; Found. C, 68.08; H, 7.29; N, 9.72.

[α]$_D$=−131.7° (C=0.381% in ethanol)

EXAMPLE 2

Preparation of Compound 2

(S)-4-(((1-propylimidazol-5-yl)methyl)sulfinyl)aniline di-p-toluoyl-D-tartrate monohydrate (495 mg) was dissolved in ethyl acetate (5 ml) and 1 N hydrochloric acid (2.52 ml), followed by separation. To the aqueous layer was added an aqueous 25% potassium carbonate solution (2.52 ml), followed by extraction with 2-propanol-ethyl acetate (1:4) twice. The organic layers were combined, washed with saturated brine and dried over magnesium sulfate, and then the solvent was distilled off under reduced pressure. To the resulting residue was added tetrahydrofuran, and then the solvent was again distilled off under reduced pressure to give (S)-(4-(((1-propylimidazol-5-yl)methyl)sulfinyl)aniline. Then, to a solution of 3-[4-(2-butoxyethoxy)phenyl]-10-propyl-7,8,9,10-tetrahydropyrido[2,3-b]azocine-6-carboxylic acid (250 mg) in dichloromethane (10 ml) were added a drop of DMF, and then oxalyl chloride (0.065 ml) at 0° C. The mixture was returned to room temperature and stirred for 30 minutes under a nitrogen atmosphere, and then the resulting solution was added dropwise to a solution of (S)-4-(((1-propylimidazol-5-yl)methyl)sulfinyl)aniline and pyridine (1.2 ml) in tetrahydrofuran (10 ml) at 0° C. under a nitrogen atmosphere. The mixture was returned to room temperature and stirred overnight. Then, water was added and the mixture was extracted with ethyl acetate. The organic layer was washed with water twice and saturated brine once, and then dried over magnesium sulfate. The solvent was distilled off under reduced pressure, and then the residue was separated and purified by basic silica gel column chromatography (ethyl acetate→methanol:ethyl acetate=3: 100) to give (S)-3-[4-(2-butoxyethoxy)phenyl]-10-propyl-N-[4-[[(1-propyl-1H-imidazol-5-yl)methyl]sulfinyl]phenyl]-7,8,9,10-tetrahydropyrido[2,3-b]azocine-6-carboxamide (310 mg) (Compound 2) as a yellow amorphous material.

$^1$H-NMR (300 MHz, CDCl$_3$) δ 0.87-0.99 (9H, m), 1.33-1.46 (2H, m), 1.56-1.75 (8H, m), 2.60-2.70 (2H, m), 3.35-3.70 (6H, m), 3.76-3.82 (4H, m), 4.01 (1H, d, J=14.1 Hz), 4.09-4.17 (3H, m), 6.53 (1H, s), 6.97 (2H, d, J=9.0 Hz), 7.35-7.52 (7H, m), 7.75 (2H, d, J=9.0 Hz), 8.24 (1H, s), 8.32 (1H, d, J=2.4 Hz).

Elementary analysis: C$_{39}$H$_{49}$N$_5$O$_4$S.0.5H$_2$O, Calcd. C, 67.60; H, 7.27; N, 10.11; Found. C, 67.67; H, 7.22; N, 9.92.

[α]$_D$=−133.4° (C=0.321% in ethanol).

EXAMPLE 3

Preparation of Compound 3

(S)-4-[[(1-propyl-1H-imidazol-5-yl)methyl]sulfinyl] aniline di-p-toluoyl-D-tartrate monohydrate (494 mg) was dissolved in ethyl acetate (5 ml) and 1 N hydrochloric acid (2.52 ml), followed by separation. To the aqueous layer was added an aqueous 25% potassium carbonate solution (2.52 ml), followed by extraction with 2-propanol-ethyl acetate (1:4) twice. The organic layers were combined, washed with saturated brine and dried over magnesium sulfate, and then the solvent was distilled off under reduced pressure. To the resulting residue was added tetrahydrofuran, and then the solvent was again distilled off under reduced pressure to give (S)-(4-[[(1-propyl-1H-imidazol-5-yl)methyl]sulfinyl] aniline. Then, to a solution of 3-[4-(2-butoxyethoxy)phenyl]-9-isobutyl-8,9-dihydro-7H-pyrido[2,3-b]azepine-6-carboxylic acid (250 mg) in dichloromethane (10 ml) were added a drop of DMF, and then oxalyl chloride (0.065 ml) was added at 0° C. The mixture was returned to room temperature and stirred for 30 minutes under a nitrogen atmosphere, and then the resulting solution was added dropwise to a solution of (S)-(4-[[(1-propyl-1H-imidazol-5-yl)methyl]sulfinyl]aniline and pyridine (1.2 ml) in tetrahydrofuran (10 ml) at 0° C. under a nitrogen atmosphere. The mixture was returned to room temperature and stirred overnight. Then, water was added and the mixture was extracted with ethyl acetate. The organic layer was washed with water twice and saturated brine once, and then dried over magnesium sulfate. The solvent was distilled off under reduced pressure, and then the resultant was separated and purified by basic silica gel column chromatography (ethyl acetate→methanol:ethyl acetate=1:20) to give (S)-3-[4-(2-butoxyethoxy)phenyl]-9-isobutyl-N-[4-[[(1-propyl-1H-imidazol-5-yl)methyl]sulfinyl]aniline]-8,9-dihydro-7H-pyrido[2,3-b]azepine-6-carboxamide (199 mg) (Compound 3) as a yellow amorphous material.

$^1$H-NMR (300 MHz, CDCl$_3$) δ 0.88-0.97 (12H, m), 1.33-1.46 (2H, m), 1.56-1.76 (4H, m), 2.10-2.20 (1H, m), 2.90-3.00 (2H, m), 3.49-3.58 (4H, m), 3.62 (2H, d, J=7.5 Hz), 3.77-3.83 (4H, m), 4.01 (1H, d, J=14.1 Hz), 4.08-4.18 (3H, m), 6.54 (1H, s) 7.00 (2H, d, J=8.7 Hz), 7.30-7.36 (3H, m), 7.43-7.46 (3H, m) 7.69 (1H, d, J=2.4 Hz), 7.74 (2H, d, J=8.7 Hz), 7.91 (1H, s) 8.34 (1H, d, J=2.4 Hz).

Elementary analysis: C$_{39}$H$_{49}$N$_5$O$_4$S.0.5H$_2$O, Calcd. C, 67.60; H, 7.27; N, 10.10; Found. C, 67.50; H, 7.22; N, 9.97.

[α]$_D$=−133.1° (C=0.251% in ethanol)

EXAMPLE 4

Preparation of Compound 4

To a solution of 3-[4-(2-butoxyethoxy)phenyl]-9-isobutyl-8,9-dihydro-7H-pyrido[2,3-b]azepine-6-carboxylic acid (130 mg) in dichloromethane (10 ml) were added a drop of DMF. Then, oxalyl chloride (0.034 ml) was added thereto, and the mixture was stirred for 1 hour under a nitrogen atmosphere. The resulting solution was added dropwise to a solution of 4-[[N-methyl-N-(tetrahydropyran-4-yl)amino] methyl]aniline (85 mg) in pyridine (10 ml) at 0° C. under a nitrogen atmosphere. The resulting mixture was stirred at room temperature under a nitrogen atmosphere overnight. Then, water was added and the mixture was extracted with ethyl acetate. The organic layer was washed with water and saturated brine, and dried over magnesium sulfate. The solvent was distilled off under reduced pressure, and then the resulting residue was purified by basic silica gel column chromatography (methanol:ethyl acetate=1:8) to give 3-[4-(2-butoxyethoxy)phenyl]-9-isobutyl-N-[4-[[methyl(tetrahydro-2H-pyran-4-yl)amino]methyl]phenyl]-8,9-dihydro-7H-pyrido[2,3-b]azepine-6-carboxamide (167 mg) (Compound 4) as a yellow amorphous material.

$^1$H-NMR (200 MHz, CDCl$_3$) δ 0.91-0.97 (9H, m), 1.33-1.50 (2H, m), 1.55-1.80 (6H, m), 2.05-2.25 (4H, m), 2.60-2.70 (1H, m), 2.90-3.00 (2H, m), 3.33-3.45 (2H, m), 3.49-3.63 (8H, m), 3.81 (2H, t, J=5.1 Hz), 4.00-4.10 (2H, m), 4.16 (2H, t, 5.1 Hz), 7.00 (2H, d, 8.4 Hz), 7.26-7.32 (3H, m), 7.43-7.54 (5H, m), 7.69 (1H, d, 2.1 Hz), 8.33 (1H, d, J=2.1 Hz).

Elementary analysis: C$_{39}$H$_{52}$N$_4$O$_4$·0.25H$_2$O, Calcd. C, 72.58; H, 8.20; N, 8.68; Found. C, 72.48; H, 8.47; N, 8.44.

REFERENCE EXAMPLE 1

To N-isobutyl-2-piperidone (1.13 g) was added an aqueous methanesulfonic acid solution (2.8 g/3.8 ml), and the mixture was refluxed at 120° C. for 2 days. The mixture was returned to room temperature, and sodium carbonate (1.55 g) was slowly added thereto. Then, the resulting solution was added dropwise to a suspension of 5-bromo-2-chloronicotinaldehyde (1.0 g) and sodium carbonate (1.25 g) in DMSO (10 ml) at 90° C. After stirring as it is for 2 hours, the mixture was cooled to 0° C. and water was added thereto. Then, 1 N hydrochloric acid (20 ml) was added and the mixture was extracted with ethyl acetate. The organic layer was washed with saturated brine, and dried over magnesium sulfate. The solvent was distilled off under reduced pressure and the residue as it is was dissolved in DMF (20 ml). Then, potassium carbonate (1.25 g) and iodomethane (0.57 ml) were added thereto, and the mixture was stirred at room temperature under a nitrogen atmosphere for 2 hours. Water was added thereto and the mixture was extracted with ethyl acetate. The organic layer was washed with saturated brine, and dried over magnesium sulfate. The solvent was distilled off under reduced pressure, and then the resulting residue was purified by silica gel column chromatography (hexane:ethyl acetate=10:1→hexane:ethyl acetate=4:1) to give methyl 5-[(5-bromo-3-formylpyridin-2-yl)(isobutyl)amino]pentanoate (867 mg) as a yellow oily material.

$^1$H-NMR (300 MHz, CDCl$_3$) δ 0.82 (6H, d, J=6.6 Hz), 1.50-1.70 (4H, m), 1.92-2.05 (1H, m), 2.29 (2H, t, J=6.9 Hz), 3.28 (2H, d, J=7.5 Hz), 3.46 (2H, t, J=7.2 Hz), 3.65 (3H, s), 8.00 (1H, d, J=2.7 Hz), 8.30 (1H, d, J=2.7 Hz), 9.88 (1H, s).

REFERENCE EXAMPLE 2

To a solution of methyl 5-[(5-bromo-3-formylpyridin-2-yl)(isobutyl)amino]pentanoate (840 mg) in dimethyl carbonate (20 ml) was added a 28% sodium methoxide solution in methanol (874 mg), and the mixture was heated at 65° C. for 3 hours under a nitrogen atmosphere. The mixture was returned to room temperature, water was added, and then the resulting mixture was extracted with ethyl acetate. The organic layer was washed with saturated brine, and dried over magnesium sulfate. The solvent was distilled off under reduced pressure and the resulting residue was purified by silica gel column chromatography (hexane:ethyl acetate=9:1) to obtain the residue, and then the obtained residue was washed with hexane-ethyl acetate to give methyl 3-bromo-10-isobutyl-7,8,9,10-tetrahydropyrido[2,3-b]azocine-6-carboxylate (741 mg) as yellow crystals.

m.p. 79.5-80.5° C.

$^1$H-NMR (300 MHz, CDCl$_3$) δ 0.90 (6H, d, J=6.9 Hz), 1.30-1.50 (2H, m), 2.16-2.25 (1H, m), 2.45-2.65 (2H, m), 3.20-3.55 (4H, m), 3.78 (3H, s), 7.38 (1H, d, J=2.4 Hz), 7.62 (1H, s), 8.02 (1H, d, J=2.4 Hz).

Elementary analysis: C$_{16}$H$_{21}$N$_2$O$_2$Br, Calcd. C, 54.40; H, 5.99; N, 7.93; Found. C, 54.30; H, 6.00; N, 7.73.

REFERENCE EXAMPLE 3

A suspension of methyl 3-bromo-10-isobutyl-7,8,9,10-tetrahydropyrido[2,3-b]azocine-6-carboxylate (690 mg), 4-(2-butoxyethoxy)phenylboric acid (605 mg) and potassium carbonate (702 mg) in toluene (15 ml), ethanol (1.5 ml) and water (1.5 ml) was stirred under an argon atmosphere for 30 minutes. Tetrakis(triphenylphosphine)palladium (113 mg) was added thereto, and the mixture was heated at 115° C. for 5 hours under an argon atmosphere. The solution was allowed to cool. Water was added and the mixture was extracted with ethyl acetate. The organic layer was washed with saturated brine, and dried over magnesium sulfate. The solvent was distilled off under reduced pressure and the resulting residue was purified by silica gel column chromatography (hexane:ethyl acetate=19:1→hexane:ethyl acetate=4:1) to give methyl 3-[4-(2-butoxyethoxy)phenyl]-10-isobutyl-7,8,9,10-tetrahydropyrido[2,3-b]azocine-6-carboxylate (723 mg) as a yellow oily material.

$^1$H-NMR (300 MHz, CDCl$_3$) δ 0.91-0.95 (9H, m), 1.33-1.66 (6H, m), 2.23-2.32 (1H, m), 2.50-2.65 (2H, m), 3.35-3.45 (2H, m), 3.50-3.57 (4H, m), 3.78-3.81 (5H, m), 4.15 (2H, t, J=4.8 Hz), 6.97 (2H, d, J=8.7 Hz), 7.41 (2H, d, J=8.7 Hz), 7.50 (1H, d, J=2.4 Hz), 7.82 (1H, s), 8.29 (1H, d, J=2.4 Hz).

REFERENCE EXAMPLE 4

To a solution of methyl 3-[4-(2-butoxyethoxy)phenyl]-10-isobutyl-7,8,9,10-tetrahydropyrido[2,3-b]azocine-6-carboxylate (700 mg) in THF (24 ml) and methanol (24 ml) was added a 1 N aqueous sodium hydroxide solution (6 ml), and the mixture was heated at 90° C. for 3 hours. After cooling to 0° C., water was added thereto, and the mixture was neutralized with 1 N hydrochloric acid and extracted with ethyl acetate. The organic layer was washed with saturated brine, and dried over magnesium sulfate. The solvent was distilled off under reduced pressure and the resulting residue was washed with hexane to give 3-[4-(2-butoxyethoxy)phenyl]-10-isobutyl-7,8,9,10-tetrahydropyrido[2,3-b]azocine-6-carboxylate (634 mg) as yellow crystals.

m.p. 135.0-136.0° C.

$^1$H-NMR (300 MHz, CDCl$_3$) δ 0.88-0.95 (9H, m), 1.33-1.66 (6H, m), 2.20-2.38 (1H, m), 2.55-2.65 (2H, m), 3.30-3.45 (6H, m), 3.80 (2H, t, J=4.8 Hz), 4.15 (2H, t, J=4.8 Hz), 6.98 (2H, d, J=8.7 Hz), 7.42 (2H, d, J=8.7 Hz), 7.52 (1H, d, J=2.4 Hz), 7.94 (1H, s), 8.31 (1H, d, J=2.4 Hz).

Elementary analysis: C$_{27}$H$_{36}$N$_2$O$_4$, Calcd. C, 71.65; H, 8.02; N, 6.19; Found. C, 71.87; H, 8.17; N, 6.13.

REFERENCE EXAMPLE 5

To N-propyl-2-piperidone (1.92 g) was added a 4 N aqueous sodium hydroxide solution (6.8 ml), and the mixture was refluxed at 115° C. for 5 hours. Thereto was added concentrated hydrochloric acid (2.27 ml) at 0° C. to neutralize the resulting mixture. Then, sodium carbonate (2.88 g), water (11.5 ml) and DMSO (18.2 ml) were added thereto. After the mixture was heated to 90° C., a solution of 5-bromo-2-chloronicotinaldehyde (1.5 g) in DMSO (23 ml)

was added dropwise thereto and the mixture was stirred as it is for 2 hours. After cooling to 0° C., water was added thereto. 6 N Hydrochloric acid (9 ml) was then added and the mixture was extracted with ethyl acetate. The organic layer was washed with saturated brine, and dried over magnesium sulfate. The solvent was distilled off under reduced pressure and the residue as it is was dissolved in DMF (50 ml), and then potassium carbonate (2.31 g) and iodomethane (1.04 ml) were added thereto. The mixture was stirred at room temperature under a nitrogen atmosphere for 2 hours. Water was added thereto and the mixture was then extracted with ethyl acetate. The organic layer was washed with saturated brine, and dried over magnesium sulfate. The solvent was distilled off under reduced pressure and the resulting residue was purified by silica gel column chromatography (hexane:ethyl acetate=10:1→hexane:ethyl acetate=4:1) to give methyl 5-[(5-bromo-3-formylpyridin-2-yl)(propyl)amino]pentanoate (909 mg) as a yellow oily material.

$^1$H-NMR (300 MHz, CDCl$_3$) δ 0.86 (3H, t, J=7.2 Hz), 1.60-1.69 (6H, m), 2.32 (2H, t, J=6.9 Hz), 3.34-3.39 (2H, m), 3.46 (2H, t, J=6.9 Hz), 3.66 (3H, s), 8.03 (1H, d, J=2.7 Hz), 8.31 (1H, d, J=2.7 Hz), 9.88 (1H, s).

REFERENCE EXAMPLE 6

To a solution of methyl 5-[(5-bromo-3-formylpyridin-2-yl)(propyl)amino]pentanoate (880 mg) in dimethyl carbonate (20 ml) was added a 28% sodium methoxide solution in methanol (951 mg), and the mixture was heated at 65° C. for 6 hours under a nitrogen atmosphere. The mixture was returned to room temperature, water was added thereto, and then the mixture was extracted with ethyl acetate. The organic layer was washed with saturated brine, and dried over magnesium sulfate. The solvent was distilled off under reduced pressure and the resulting residue was purified by silica gel column chromatography (hexane:ethyl acetate=9:1) to give methyl 3-bromo-10-propyl-7,8,9,10-tetrahydropyrido[2,3-b]azocine-6-carboxylate (835 mg) as a yellow oily material.

$^1$H-NMR (300 MHz, CDCl$_3$) δ 0.92 (3H, t, J=7.5 Hz), 1.40-1.70 (4H, m), 2.40-2.65 (2H, m), 3.30-3.60 (4H, m), 3.78 (3H, s), 7.40 (1H, d, J=2.7 Hz), 7.61 (1H, s), 8.06 (1H, d, J=2.7 Hz).

REFERENCE EXAMPLE 7

A suspension of methyl 3-bromo-10-propyl-7,8,9,10-tetrahydropyrido[2,3-b]azocine-6-carboxylate (820 mg), 4-(2-butoxyethoxy)phenylboric acid (748 mg) and potassium carbonate (868 mg) in toluene (15 ml), ethanol (1.5 ml) and water (1.5 ml) was stirred under an argon atmosphere for 30 minutes. Tetrakis(triphenylphosphine)palladium (140 mg) was added thereto, and the mixture was heated at 115° C. for 6 hours under an argon atmosphere, which was allowed to cool. Water was added and the mixture was extracted with ethyl acetate. The organic layer was washed with saturated brine, and dried over magnesium sulfate. The solvent was distilled off under reduced pressure and the resulting residue was purified by silica gel column chromatography (hexane:ethyl acetate=19:1→hexane:ethyl acetate=4:1) to give methyl 3-[4-(2-butoxyethoxy)phenyl]-10-propyl-7,8,9,10-tetrahydropyrido[2,3-b]azocine-6-carboxylate (870 mg) as a yellow oily material.

$^1$H-NMR (300 MHz, CDCl$_3$) δ 0.91-0.98 (6H, m), 1.33-1.73 (8H, m), 2.50-2.70 (2H, m), 3.35-3.60 (6H, m), 3.78-3.82 (5H, m), 4.15 (2H, t, J=4.8 Hz), 6.97 (2H, d, J=8.7 Hz), 7.41 (2H, d, J=8.7 Hz), 7.51 (1H, d, J=2.7 Hz), 7.79 (1H, s), 8.31 (1H, d, J=2.7 Hz).

REFERENCE EXAMPLE 8

To a solution of methyl 3-[4-(2-butoxyethoxy)phenyl]-10-propyl-7,8,9,10-tetrahydropyrido[2,3-b]azocine-6-carboxylate (850 mg) in THF (30 ml) and methanol (30 ml) was added a 1 N aqueous sodium hydroxide solution (7.5 ml), and the mixture was heated at 90° C. for 3 hours. After cooling to 0° C., water was added thereto, and the mixture was neutralized with 1 N hydrochloric acid and extracted with ethyl acetate. The organic layer was washed with saturated brine, and dried over magnesium sulfate. The solvent was distilled off under reduced pressure and the resulting residue was washed with hexane to give 3-[4-(2-butoxyethoxy)phenyl]-10-propyl-7,8,9,10-tetrahydropyrido[2,3-b]azocine-6-carboxylic acid (739 mg) as yellow crystals.

m.p. 123.0-125.0° C.

$^1$H-NMR (300 MHz, CDCl$_3$) δ 0.90-0.99 (6H, m), 1.33-1.73 (8H, m), 2.55-2.65 (2H, m), 3.35-3.60 (6H, m), 3.80 (2H, t, J=5.1 Hz), 4.15 (2H, t, J=5.1 Hz), 6.98 (2H, d, J=8.7 Hz), 7.41 (2H, d, J=8.7 Hz), 7.52 (1H, d, J=2.4 Hz), 7.91 (1H, s), 8.33 (1H, d, J=2.4 Hz).

Elementary analysis: $C_{26}H_{34}N_2O_4$, Calcd. C, 71.21; H, 7.81; N, 6.39; Found. C, 71.17; H, 7.90; N, 6.10.

REFERENCE EXAMPLE 9

A mixture of potassium thiocyanate (119.2 g), dihydroxyacetone dimer (73.9 g) and propylamine hydrochloride (100 g) was portionwise added to a mixed solution of acetic acid (89 ml) and 1-butanol (590 ml). The mixture was stirred at room temperature for 1 day, and then water (118 ml) was added thereto, followed by stirring for 30 minutes. The precipitated solid was collected by filtration, and further washed with water (180 ml) twice and hexane once. The resulting solid was dried under reduced pressure to give 5-hydroxymethyl-2-mercapto-1-propylimidazole (71.2 g) as colorless crystals.

$^1$H-NMR (200 MHz, CDCl$_3$) δ 0.87 (3H, t, J=7.4 Hz), 1.61-1.79 (2H, m), 3.91 (2H, t, J=7.4 Hz), 4.32 (2H, s), 5.26 (1H, br), 6.79 (1H, s), 11.95 (1H, s).

Elementary analysis: $C_7H_{12}N_2OS.0.25H_2O$, Calcd. C, 47.57; H, 7.13; N, 15.85; Found. C, 47.22; H, 6.94; N, 15.99.

REFERENCE EXAMPLE 10

To 5.0 M nitric acid (370 ml) was added sodium nitrite (1.14 g), and then 5-hydroxymethyl-2-mercapto-1-propylimidazole (71.0 g) was portionwise added at 0° C. The mixture was returned to room temperature and stirred for 2 hours, followed by adding water (200 ml). Thereto was added potassium carbonate at 0° C. to neutralize the mixture. Then, the solvent was distilled off under reduced pressure. Ethanol was added thereto, insolubles were filtered off, and the solvent was then distilled off under reduced pressure. To the resulting residue was added methanol-ethyl acetate, and then basic silica gel was added thereto. The resulting mixture was purified by basic silica gel column chromatography (methanol-ethyl acetate=1:8). The resulting solid was recrystallized from diisopropyl ether-ethyl acetate to give 5-hydroxymethyl-1-propylimidazole (33.6 g) as brown crystals.

$^1$H-NMR (200 MHz, CDCl$_3$) δ 0.96 (3H, t, J=7.4 Hz), 1.76-1.94 (2H, m), 3.97 (2H, t, J=7.2 Hz), 4.63 (2H, s), 6.97 (1H, s), 7.48 (1H, s).

REFERENCE EXAMPLE 11

To 5-hydroxymethyl-1-propylimidazole (33.0 g) was portionwise added thionyl chloride (80 ml) at 0C, and the mixture was heated at 90° C. for 30 minutes under a nitrogen atmosphere. The mixture was returned to room temperature, and then the solvent was distilled off under reduced pressure. The resulting residue was dissolved in methanol, and the solvent was again distilled off under reduced pressure. The resulting solid was recrystallized from ethyl acetate to give 5-chloromethyl-1-propylimidazole hydrochloride (43.8 g) as colorless crystals.

$^1$H-NMR (200 MHz, DMSO-$d_6$) δ 0.92 (3H, t, J=7.4 Hz), 1.84-1.95 (2H, m), 4.18 (2H, t, J=7.2 Hz), 5.04 (2H, s), 7.82 (1H, s), 9.24 (1H, s).

REFERENCE EXAMPLE 12

4-Aminothiophenol (2.5 g) was dissolved in water (2.5 ml) and isopropanol (10 ml). Triethylamine (5.5 ml) was added thereto, and then the mixture was cooled to −15 to −10° C. A solution of 5-(chloromethyl)-1-propyl-1H-imidazole hydrochloride (3.9 g) in water (2.5 ml) was added dropwise thereto at −15 to −10° C., and the mixture was stirred at the same temperature for 1 hour. After isopropanol was distilled off under reduced pressure, methyl isobutyl ketone (25 ml) was then added, and the organic layer was washed with water. To the organic layer was added activated carbon (0.1 g), and the mixture was stirred at room temperature for 10 minutes. The organic layer was concentrated and dissolved in methyl isobutyl ketone (30 ml). Separately, di-p-toluoyl-(D)-tartaric acid (7.7 g) was dissolved in a mixed solution of toluene (90 ml) and methyl isobutyl ketone (60 ml), and to the solution was added water (3.6 ml). Then, the above methyl isobutyl ketone solution was slowly added dropwise over 2 hours. After stirring the resulting mixture for 1 hour, 30% hydrogen peroxide solution (6.8 g) was added thereto, and the mixture was stirred at room temperature for 24 hours. Methanol (30 ml) was added thereto and the mixture was stirred at 50° C. for 8 hours. Water (30 ml) was added thereto, and the mixture was stirred at room temperature for 5 hours. The precipitated crystals were collected by filtration and washed with water (30 ml) to give (−)-4-{[(1-propyl-1H-imidazol-5-yl)methyl]sulfinyl}phenylamine di-p-toluoyl-D-tartrate monohydrate (7.1 g).

m.p. 134-136° C.

REFERENCE EXAMPLE 13

To N-isobutyl-2-pyrrolidone (1.28 g) was added an aqueous methanesulfonic acid solution (3.5 g/4.7 ml), and the mixture was refluxed at 130° C. for 3 days. The mixture was returned to room temperature, and sodium carbonate (1.92 g) was slowly added thereto. The resulting solution was added dropwise at 90° C. to a suspension of 5-bromo-2-chloronicotinaldehyde (1.0 g) and sodium carbonate (1.56 g) in DMSO (13 ml), and the mixture as it is was stirred for 4 hours, followed by cooling to 0° C. Water was added thereto, 6 N hydrochloric acid (5 ml) was then added, and the mixture was extracted with ethyl acetate. The organic layer was washed with water and saturated brine, and dried over magnesium sulfate. The solvent was distilled off under reduced pressure and the residue as it is was dissolved in DMF (20 ml). Potassium carbonate (1.25 g) and iodomethane (0.57 ml) were added thereto, and the mixture was stirred at room temperature under a nitrogen atmosphere for 2 hours. Water was added thereto and the mixture was extracted with ethyl acetate. The organic layer was washed with saturated brine, and dried over magnesium sulfate. The solvent was distilled off under reduced pressure and the resulting residue was purified by silica gel column chromatography (hexane:ethyl acetate=12:1→hexane:ethyl acetate=4:1) to give methyl 4-[(5-bromo-3-formylpyridin-2-yl)(isobutyl)amino]butanote (763 mg) as a yellow oily material.

$^1$H-NMR (300 MHz, CDCl$_3$) δ 0.82 (6H, d, J=6.6 Hz), 1.88-2.04 (3H, m), 2.27 (2H, t, J=7.2 Hz), 3.28 (2H, d, J=7.5 Hz), 3.51 (2H, t, J=7.5 Hz), 3.64 (3H, s), 8.02 (1H, d, J=2.7 Hz), 8.32 (1H, d, J=2.7 Hz), 9.89 (1H, s).

REFERENCE EXAMPLE 14

To a solution of methyl 4-[(5-bromo-3-formylpyridin-2-yl)(isobutyl)amino]butanoate (750 mg) in dimethyl carbonate (20 ml) was added a 28% sodium methoxide solution in methanol (810 mg), and the mixture was heated at 50° C. for 2 hours under a nitrogen atmosphere. The mixture was returned to room temperature, water was added thereto and then extracted with ethyl acetate. The organic layer was washed with saturated brine, and dried over magnesium sulfate. The solvent was distilled off under reduced pressure and the resulting residue was purified by silica gel column chromatography (hexane:ethyl acetate=19:1→hexane:ethyl acetate=6:1) to give methyl 3-bromo-9-isobutyl-8,9-dihydro-7H-pyrido[2,3-b]azepine-6-carboxylate (654 mg) as a yellow oily material.

$^1$H-NMR (300 MHz, CDCl$_3$) δ 0.90 (6H, d, J=6.6 Hz), 2.01-2.13 (1H, m), 2.83 (2H, t, J=3.9 Hz), 3.38 (2H, t, J=4.5 Hz), 3.52 (2H, d, J=7.5 Hz), 3.80 (3H, s), 7.46 (1H, s), 7.61 (1H, d, J=2.4 Hz), 8.08 (1H, d, J=2.4 Hz).

REFERENCE EXAMPLE 15

A suspension of methyl 3-bromo-9-isobutyl-8,9-dihydro-7H-pyrido[2,3-b]azepine-6-carboxylate (640 mg), 4-(2-butoxyethoxy)phenylboric acid (583 mg) and potassium carbonate (678 mg) in toluene (15 ml), ethanol (1.5 ml) and water (1.5 ml) was stirred for 30 minutes under an argon atmosphere. Tetrakis(triphenylphosphine)palladium (110 mg) was added thereto, and the mixture was heated at 115° C. for 6 hours under an argon atmosphere, which was allowed to cool. Water was added thereto and the mixture was extracted with ethyl acetate. The organic layer was washed with saturated brine, and dried over magnesium sulfate. The solvent was distilled off under reduced pressure and the resulting residue was purified by silica gel column chromatography (hexane:ethyl acetate=19:1→hexane:ethyl acetate=4:1) to give methyl 3-[4-(2-butoxyethoxy)phenyl]-9-isobutyl-8,9-dihydro-7H-pyrido[2,3-b]azepine-6-carboxylate (740 mg) as a yellow oily material.

$^1$H-NMR (300 MHz, CDCl$_3$) δ 0.91-0.96 (9H, m), 1.30-1.45 (2H, m), 1.55-1.70 (2H, m), 2.05-2.20 (1H, m), 2.86 (2H, t, J=4.5 Hz), 3.44 (2H, t, J=5.1 Hz), 3.55 (2H, t, J=6.3 Hz), 3.60 (2H, d, J=7.2 Hz), 3.79-3.82 (5H, m), 4.16 (2H, t, J=4.8 Hz), 6.99 (2H, d, J=9.0 Hz), 7.44 (2H, d, J=9.0 Hz), 7.65 (1H, s), 7.70 (1H, d, J=2.4 Hz), 8.32 (1H, d, J=2.4 Hz).

REFERENCE EXAMPLE 16

To a solution of methyl 3-[4-(2-butoxyethoxy)phenyl]-9-isobutyl-8,9-dihydro-7H-pyrido[2,3-b]azepine-6-carboxylate (720 mg) in THF (25 ml) and methanol (25 ml) was added a 1 N aqueous sodium hydroxide solution (6.4 ml), and the mixture was heated at 90° C. for 3 hours. After cooling to 0° C., water was added thereto, and the mixture was neutralized with 1 N hydrochloric acid and extracted with ethyl acetate. The organic layer was washed with saturated brine, and dried over magnesium sulfate. The solvent was distilled off under reduced pressure and the resulting residue was washed with hexane to give 3-[4-(2-butoxyethoxy)phenyl]-9-isobutyl-8,9-dihydro-7H-pyrido[2,3-b]azepine-6-carboxylic acid (654 mg) as yellow crystals. m.p. 114.0-116.0° C.

$^1$H-NMR (300 MHz, CDCl$_3$) δ 0.86-0.96 (9H, m), 1.34-1.46 (2H, m), 1.57-1.66 (2H, m), 2.05-2.20 (1H, m), 2.83-2.93 (2H, m), 3.45-3.48 (2H, m), 3.55 (2H, t, J=6.6 Hz), 3.62 (2H, d, J=7.5 Hz), 3.81 (2H, t, J=5.1 Hz), 4.16 (2H, t, J=5.1 Hz), 7.00 (2H, d, J=9.0 Hz), 7.44 (2H, d, J=9.0 Hz), 7.71 (1H, d, J=2.4 Hz), 7.75 (1H, s), 8.35 (1H, d, J=2.4 Hz).

Elementary analysis: $C_{26}H_{34}N_2O_4$, Calcd. C, 71.21; H, 7.81; N, 6.39; Found. C, 70.91; H, 7.87; N, 6.07.

EXPERIMENTAL EXAMPLE (1) Cloning of Human CCR5 Chemokine Receptor

Cloning of a CCR5 gene was conducted from human spleen cDNA by a PCR method. Using 0.5 ng of spleen cDNA (Toyobo Co., Ltd., QUICK-Clone cDNA) as a template, the PCR reaction was carried out in a DNA Thermal Cycler 480 (Perkin Elmer) using a TaKaRa EX Taq (Takara Shuzo Co., Ltd.) (reaction conditions: 30 cycles of treatments at 95° C. for 1 minute, at 60° C. for 1 minute, and at 75° C. for 5 minutes) by adding 25 pmol of primers, SEQ ID NO. 1 (sequence length: 34; sequence type: nucleic acid; number of chains: a single chain; topology: linear; sequence kind: other nucleic acid, synthetic DNA) described in Experimental Example (1) of WO 99/32100, and SEQ ID NO. 2 (sequence length: 34; sequence type: nucleic acid; number of chains: a single chain; topology: linear; sequence kind: other nucleic acid, synthetic DNA) described in Experimental Example (1) of WO 99/32100, respectively, which were prepared by referring to the base sequence of the CCR5 gene described by Samson et al. (Biochemistry 35 (11), 3362-3367 (1996)). The PCR products were subjected to agarose gel electrophoresis to collect DNA fragments of about 1.0 kb. Then, the CCR5 gene was cloned using an Original TA Cloning Kit (Funakoshi Co., Ltd.).

(2) Preparation of Plasmid for Expression of Human CCR5

The plasmids obtained above were digested with restriction enzymes XbaI (Takara Shuzo Co., Ltd.) and BamHI (Takara Shuzo Co., Ltd.), and subjected to agarose gel electrophoresis to collect DNA fragments of about 1.0 kb. The DNA fragments and a plasmid pcDNA3.1 (Funakoshi Co., Ltd.) for expression in animal cells, which was previously digested with XbaI and BamHI, were mixed and ligated by DNA Ligation Kit Ver.2 (Takara Shuzo Co., Ltd.). Transformation of E. coli JM109 competent cells (Takara Shuzo Co., Ltd.) gave plasmid pCKR5.

(3) Introduction of the Plasmid for Expression of Human CCR5 into CHO—K1 Cells and Expression Thereof CHO—K1 cells grown in a 750 ml tissue culture flask (Becton Dickinson) using Ham's F12 medium (Nihon Pharmaceutical Co., Ltd.) containing 10% fetal bovine serum (Lifetech Oriental) were collected from the flask by using 0.5 g/L trypsin-0.2 g/L EDTA (Lifetech Oriental). The cells were then washed with PBS (Lifetech Oriental), centrifuged (1000 rpm, 5 minutes), and suspended in PBS. Next, DNA was introduced into the cells using Gene Pulser (Bio-Rad Laboratories Inc.) under the following conditions. Namely, 8×10$^6$ cells and 10 µg of plasmid pCKR5 for expression of human CCR5 were added into a cuvette of a 0.4 cm-gap, and electroporation was carried out at an electric voltage of 0.25 kV and a capacitance of 960 µF. Subsequently, the cells were transferred into Ham's F12 medium containing 10% fetal bovine serum, and incubated for 24 hours. The cells were again collected, centrifuged, and then suspended in Ham's F12 medium containing 10% fetal bovine serum and Geneticin (Lifetech Oriental) at a concentration of 500 µg/ml. The suspension of cells was diluted to a concentration of 10$^4$ cells/ml, and inoculated on a 96-well plate (Becton Dickinson) to give Geneticin-resistant strains.

Subsequently, the Geneticin-resistant strains were cultured in the 96-well plate (Becton Dickinson), and then CCR5-expressing cells were selected from the resistant strains. Namely, an assay buffer (Ham's F12 medium containing 0.5% BSA, and 20 mM HEPES (Wako Pure Chemical Industries, Ltd., pH 7.2)) containing 200 pM [$^{125}$I]-RANTES (Amersham) as a ligand was added to each well and the binding reaction was carried out at room temperature for 40 minutes. Each well plate containing the cells was washed with ice-cooled PBS, and then to each well was added 1 M NaOH in an amount of 50 µl/well, which was stirred. The cells to which the ligand bound specifically, i.e., CCR5/CHO strains, were selected by measurement of radioactivity by γ-counter.

(4) Evaluation of Compound Based on CCR5 Antagonist Activity

The CCR5/CHO strains were inoculated on a 96-well microplate at a concentration of 5×10$^4$ cells/well, respectively and were cultured for 24 hours. After the medium was removed by suction, to each well was added an assay buffer containing a test compound (1 µM), and [$^{125}$I]-RANTES (Amersham) used as a ligand at a concentration of 100 pM. The reaction was carried out at room temperature for 40 minutes. After the assay buffer was removed by suction, each well plate containing the cells were washed with ice-cooled PBS twice. Then, to each well was added 200 µl of MicroScint-20 (Packard Industry Company, Inc.), and the radioactivity was measured with TopCount (Packard Industry Company, Inc.).

According to the method above, inhibitory ratios to CCR5 binding of the test compounds were determined. The results are shown in Table 1.

TABLE 1

| Compound No. | Binding Inhibitory Ratio (%) |
|---|---|
| 1 | 94 |
| 2 | 93 |
| 3 | 100 |
| 4 | 100 |

FORMULATION EXAMPLE 1

Capsules

| | |
|---|---|
| (1) (S)-3-[4-(2-butoxyethoxy)phenyl]-10-isobutyl-N-[4-[[(1-propyl-1H-imidazol-5-yl)methyl]sulfinyl]phenyl]-7,8,9,10-tetrahydropyrido[2,3-b]azocine-6-carboxamide | 40 mg |
| (2) lactose | 61 mg |
| (3) microcrystalline cellulose | 18 mg |
| (4) magnesium stearate | 1 mg |
| contents of 1 capsule | 120 mg |

After mixing (1), (2), (3) and (4), the mixture is filled in gelatin capsules.

FORMULATION EXAMPLE 2

Capsules

| | |
|---|---|
| (1) (S)-3-[4-(2-butoxyethoxy)phenyl]-10-propyl-N-[4-[[(1-propyl-1H-imidazol-5-yl)methyl]sulfinyl]phenyl]-7,8,9,10-tetrahydropyrido[2,3-b]azocine-6-carboxamide | 40 mg |
| (2) lactose | 61 mg |
| (3) microcrystalline cellulose | 18 mg |
| (4) magnesium stearate | 1 mg |
| contents of 1 capsule | 120 mg |

After mixing (1), (2), (3) and (4), the mixture is filled in gelatin capsules.

FORMULATION EXAMPLE 3

Tablets

| | |
|---|---|
| (1) (S)-3-[4-(2-butoxyethoxy)phenyl]-10-isobutyl-N-[4-[[(1-propyl-1H-imidazol-5-yl)methyl]sulfinyl]phenyl]-7,8,9,10-tetrahydropyrido[2,3-b]azocine-6-carboxamide | 40 mg |
| (2) mannitol | 51.2 mg |
| (3) microcrystalline cellulose | 18 mg |
| (4) hydroxypropyl cellulose | 3.6 mg |
| (5) croscarmellose sodium | 6 mg |
| (6) magnesium stearate | 1.2 mg |
| contents of 1 tablet | 120 mg |

(1), (2), (3) and (4) are mixed and granulated. To the granules are added (5) and (6), and the mixture is compressed into tablets.

FORMULATION EXAMPLE 4

Tablets

| | |
|---|---|
| (1) (S)-3-[4-(2-butoxyethoxy)phenyl]-10-propyl-N-[4-[[(1-propyl-1H-imidazol-5-yl)methyl]sulfinyl]phenyl]-7,8,9,10-tetrahydropyrido[2,3-b]azocine-6-carboxamide | 40 mg |
| (2) mannitol | 51.2 mg |
| (3) microcrystalline cellulose | 18 mg |
| (4) hydroxypropyl cellulose | 3.6 mg |
| (5) croscarmellose sodium | 6 mg |
| (6) magnesium stearate | 1.2 mg |
| contents of 1 tablet | 120 mg |

(1), (2), (3) and (4) are mixed and granulated. To the granules are added (5) and (6), and the mixture is compressed into tablets.

INDUSTRIAL APPLICABILITY

The compound represented by the formula (I) or a salt thereof of the present invention has strong CCR5 antagonist activity and improved solubility in water, and thus can be advantageously used for prevention and treatment of a variety of human HIV infection, for example AIDS.

The invention claimed is:

1. A compound represented by the formula:

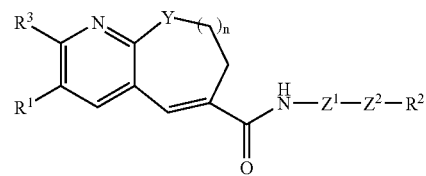

wherein $R^1$ is a 5- or 6-membered ring which may be substituted;

$R^3$ is a hydrogen atom, a lower alkyl group which may be substituted or a lower alkoxy group which may be substituted;

$Z^1$ is a 5- or 6-membered aromatic ring which may be further substituted;

$Z^2$ is a group represented by $-Z^{2a}-W^1-Z^{2b}-$ wherein $Z^{2a}$ and $Z^{2b}$ are each O, $S(O)_m$ (wherein m is 0, 1 or 2), a substituted imino group, or a bond; and $W^1$ is an alkylene chain which may be substituted, an alkenylene chain which may be substituted, or a bond;

n is 2;

Y is or $NR^4$ (wherein $R^4$ is a hydrogen atom, a hydrocarbon group which may be substituted, a heterocyclic group which may be substituted, or an acyl group which may be substituted); and $R^2$ is (1) a substituted amino group, in which the nitrogen atom may be converted to a quaternary ammonium or an oxide, (2) a nitrogen-containing heterocyclic group which may be substituted and may contain a sulfur atom or an oxygen atom as a ring-constituting atom, in which the nitrogen atom may be converted to a quaternary ammonium or an oxide, (3) a group represented by the formula:

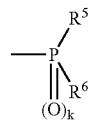

wherein k is 0 or 1; when k is 0, the phosphorus atom may form a phosphonium salt; $R^5$ and $R^6$ are each a hydrocarbon group which may be substituted, a substituted hydroxy group or an amino group which may be substituted; or $R^5$ and $R^6$ may be bonded to each other to form a ring with the adjacent phosphorus atom, or a salt thereof.

2. The compound according to claim 1, wherein $R^1$ is a benzene, a furan, a thiophene, a pyridine, a cyclopentane, cyclohexane, a pyrrolidine, a piperidine, a piperazine, a morpholine, a thiomorpholine or a tetrahydropyran, each of which may be substituted.

3. The compound according to claim 1, wherein $R^1$ is a benzene which may be substituted.

4. The compound according to claim 1, wherein $Z^1$ is a benzene which may be substituted with a substituent selected from (1) a halogen atom, (2) a $C_{1-4}$ alkyl group which may be substituted with a halogen atom, and (3) a $C_{1-4}$ alkoxy group which may be substituted with a halogen atom.

5. The compound according to claim 1, wherein $Z^1$ is a benzene which may be substituted with a methyl group or a trifluoromethyl group.

6. The compound according to claim 1, wherein $Z^2$ is a group represented by -$Z^{2a}$-$W^2$-$Z^{2b}$- wherein $Z^{2a}$ and $Z^{2b}$ are each O, $S(O)_m$ (wherein m is 0, 1 or 2), a substituted imino group, or a bond; and $W^2$ is an alkylene chain which may be substituted.

7. The compound according to claim 1, wherein $Z^2$ is —$CH_2$—, —CH(OH)—, or —$S(O)_m$—$CH_2$— (wherein m is 0, 1 or 2).

8. The compound according to claim 1, wherein $Z^2$ is a group represented by —$S(O)_m$—$CH_2$— (wherein m is 0, 1 or 2).

9. The compound according to claim 1, wherein $R^2$ is represented by the formula —NRR' (wherein R and R' are each an aliphatic hydrocarbon group which may be substituted, or an alicyclic heterocyclic group which may be substituted).

10. The compound according to claim 1, wherein $R^2$ is a nitrogen-containing aromatic heterocyclic group which may be substituted.

11. The compound according to claim 1, wherein $R^2$ is an imidazolyl group which may be substituted or a triazolyl group which may be substituted.

12. The compound according to claim 1, wherein $R^1$ is a benzene, a furan, a thiophene, a pyridine, a cyclopentane, a cyclohexane, a pyrrolidine, a piperidine, a piperazine, a morpholine, a thiomorpholine or a tetrahydropyran, each of which may be substituted with a halogen, a nitro, a cyano, a $C_{1-6}$ alkyl, a $C_{1-6}$ alkoxy, a $C_{1-6}$ alkoxy-$C_{1-6}$ alkyl or a $C_{1-6}$ alkoxy-$C_{1-6}$ alkoxy, a Y-containing ring is an 8-membered ring which contains a nitrogen atom, as a ring-constituting atom, and may have, as a substituent, an alkyl which may be substituted, an alkenyl which may be substituted, an aryl which may be substituted, a heterocyclic group which may be substituted or formyl, $Z^1$ is a benzene which may be substituted with substituent(s) selected from (1) a halogen atom, (2) a $C_{1-4}$ alkyl group which may be substituted with halogen atom(s) and (3) a $C_{1-4}$ alkoxy group which may be substituted with halogen atom(s), $Z^2$ is $Z^{2a}$-$W$-$Z^{2b}$- wherein $Z^{2a}$ and $Z^{2b}$ are each O, $S(O)_m$ (wherein m is 0, 1 or 2), an imino group substituted with a $C_{1-4}$ alkyl group, or a bond, and $W^1$ is a bond, or a $C_{1-4}$ alkylene chain or a $C_{2-4}$ alkenylene chain, each of which may have, as a substituent, a $C_{1-6}$ alkyl, a hydroxy group, a hydroxyimino or a $C_{1-6}$ alkoxyimino, and $R^2$ is an amino group substituted with a $C_{1-4}$ alkyl group, or a nitrogen-containing heterocyclic group which may contain a sulfur atom or an oxygen atom as a ring-constituting atom and may be substituted with a $C_{1-4}$ alkyl group.

13. A compound represented by the formula:

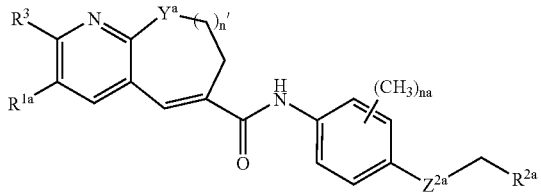

wherein $R^{1a}$ is a ($C_{1-6}$ alkoxy-$C_{1-6}$alkoxy)phenyl;

$R^{2a}$ is (1) an N—$C_{1-6}$ alkyl-N-tetrahydropyranylamino, (2) an imidazolyl which may be substituted with a $C_{1-6}$ alkyl which may be substituted, or (3) a triazolyl which may be substituted with a $C_{1-6}$ alkyl which may be substituted;

$R^3$ is a hydrogen atom, a lower alkyl group which may be substituted or a lower alkoxy group which may be substituted;

$Y^a$ is an imino group which may have, as a substituent, a formyl, a $C_{1-6}$ alkyl which may be substituted, a $C_{2-6}$ alkenyl which may be substituted, an aryl which may be substituted, a heterocyclic group which may be substituted, an arylmethyl which may be substituted or a heterocyclic methyl which may be substituted;

n'is;

na is 0 or 1; and $Z^{2a}$ is a bond, S, SO or $SO_2$, or a salt thereof.

14. The compound according to claim 13, wherein $Z^{2a}$ is SO.

15. The compound according to claim 13, wherein $Z^{2a}$ is SO having a configuration of (S).

16. The compound according to claim 13, wherein $Y^a$ is an imino group which may have, as a substituent, a formyl, a $C_{1-6}$ alkyl which may be substituted, a $C_{2-6}$ alkenyl which may be substituted, an aryl which may be substituted, a heterocyclic group which may be substituted, an arylmethyl which may be substituted or a heterocyclic methyl which may be substituted.

17. (S)-3-[4-(2-butoxyethoxy)phenyl]-10-isobutyl-N-[4-[[(1-propyl-1H-imidazol-5-yl)methyl]sulfinyl]phenyl]-7,8,9,10-tetrahydropyrido[2,3-b]azocine-6-carboxamide.

18. (S)-3-[4-(2-butoxyethoxy)phenyl]-10-propyl-N-[4-[[(1-propyl-1H-imidazol-5-yl)methyl]sulfinyl]phenyl]-7,8,9,10-tetrahydropyrido[2,3-b]azocine-6-carboxamide.

19. A process for producing a compound represented by the formula:

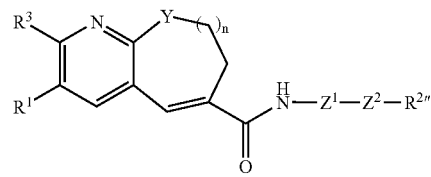

wherein $R^{2''}$ is (1) a substituted amino group, in which the nitrogen atom may be converted to a quaternary ammonium, (2) a nitrogen-containing heterocyclic group which may be substituted and may contain a sulfur atom or an oxygen atom as a ring-constituting atom, in which the nitrogen atom may be converted to a quaternary ammonium, or (3) a group represented by the formula:

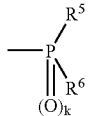

wherein k is 0 or 1; when k is 0, the phosphorus atom may form a phosphonium salt; $R^5$ and $R^6$ are each a hydrocarbon group which may be substituted, a substituted hydroxy group or an amino group which may be substituted; and $R^5$ and $R^6$ may be bonded to each other to form a ring with the adjacent phosphorus atom; and the other symbols have the same meanings as defined in claim 1, or a salt thereof, which comprises subjecting a compound represented by the formula:

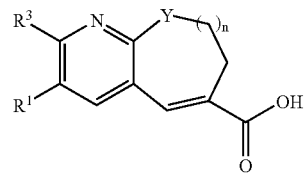

wherein each symbol has the same meaning as defined in claim 1, or a salt thereof or a reactive derivative thereof, and a compound represented by the formula:

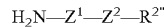

wherein $Z^1$ and $Z^2$ have the same meaning as defined in claim 1 are and $R^{2''}$ has the same meaning as defined above, or salt thereof, to a condensation reaction, and then optionally to a deprotection reaction, an oxidation/reduction reaction and/or a quaternization reaction.

* * * * *